(12) United States Patent
Choi et al.

(10) Patent No.: US 11,147,816 B2
(45) Date of Patent: Oct. 19, 2021

(54) COMPOSITION FOR INDUCING DIFFERENTIATION AND PROTECTION OF NEURAL STEM CELLS AND METHOD FOR INDUCING NEURO-REGENERATION USING THE SAME COMPOSITION

(71) Applicant: GENUV Inc., Seoul (KR)

(72) Inventors: Kang-Yell Choi, Seoul (KR); Mi-Yeon Kim, Seoul (KR); Sungho Han, Seoul (KR)

(73) Assignee: GENUV Inc., Seoul (KR)

( * ) Notice: Subject to any disclaimer, the term of this patent is extended or adjusted under 35 U.S.C. 154(b) by 0 days.

(21) Appl. No.: 16/545,438

(22) Filed: Aug. 20, 2019

(65) Prior Publication Data

US 2020/0046706 A1    Feb. 13, 2020

Related U.S. Application Data

(60) Division of application No. 15/897,138, filed on Feb. 14, 2018, now Pat. No. 10,485,802, which is a
(Continued)

(30) Foreign Application Priority Data

Nov. 25, 2016 (KR) .................. 10-2016-0158739
Mar. 22, 2017 (KR) .................. 10-2017-0036268

(51) Int. Cl.
*A61K 31/519* (2006.01)
*A61P 25/16* (2006.01)
*A61P 25/28* (2006.01)

(52) U.S. Cl.
CPC ............ *A61K 31/519* (2013.01); *A61P 25/16* (2018.01); *A61P 25/28* (2018.01)

(58) Field of Classification Search
CPC .......... A61K 31/519; A61P 25/16; A61P 25/28
See application file for complete search history.

(56) References Cited

U.S. PATENT DOCUMENTS 6,310,060 B1    10/2001 Barrett et al.
2009/0093462 A1    4/2009 Abel et al.
(Continued)

FOREIGN PATENT DOCUMENTS

CN      105796544       7/2016
CN      105816461       8/2016
(Continued)

OTHER PUBLICATIONS

Liu et al., Protein & Cell, 2016;7:638-650 (Year: 2016) (Year: 2016).*
(Continued)

*Primary Examiner* — San Ming R Hui
(74) *Attorney, Agent, or Firm* — Fenwick & West LLP

(57) ABSTRACT

The present invention relates to a method of inducing neuro-regeneration comprising administering a MEK 1/2 inhibitor to a patient in need thereof. In the present invention, the MEK1/2 inhibitor induces neuro-regeneration by differentiating neural stem cells into neurons, by protecting neural stem cells and neurons against cytotoxicity of amyloid-betas, or by both of the above. Also, the present invention relates to a method of protecting neurons against neuronal loss or damage comprising administering a MEK1/2 inhibitor. In addition, this invention relates to a method of preventing or treating neurodegenerative disease due to neuronal loss or damage for patients in need thereof comprising administering a MEK 1/2 inhibitor.

9 Claims, 32 Drawing Sheets

Specification includes a Sequence Listing.

Related U.S. Application Data continuation of application No. PCT/KR2017/013444, filed on Nov. 23, 2017.

(56) References Cited

U.S. PATENT DOCUMENTS

| | | | |
|---|---|---|---|
| 2012/0122728 | A1 | 5/2012 | Hickman et al. |
| 2015/0238562 | A1 | 8/2015 | Su et al. |
| 2016/0177260 | A1 | 6/2016 | Shoji |
| 2016/0346329 | A1 | 12/2016 | Choi et al. |
| 2017/0209451 | A1 | 7/2017 | Choi et al. |

FOREIGN PATENT DOCUMENTS

| | | | |
|---|---|---|---|
| KR | 10-2004-0016785 A | | 9/2005 |
| KR | 20090046576 | | 5/2009 |
| KR | 20090047532 | | 5/2009 |
| KR | 101211610 B1 | | 12/2012 |
| KR | 20160040286 A | | 4/2016 |
| KR | 20160048807 A | | 5/2016 |
| WO | WO 2013/093137 A1 | | 6/2013 |
| WO | WO 2013/178320 A1 | | 12/2013 |
| WO | WO 2015/020234 A1 | | 2/2015 |

OTHER PUBLICATIONS

Arendt, T., et al., "Increased expression and subcellular translocation of the mitogen activated protein kinase and mitogen-activated protein kinase in Alzheimer's disease," Neuroscience, 1995, vol. 68, No. 1, pp. 5-18.

Arora, K. et al., "Nicotinic Acetylcholine Receptors Sensitize a MAPK-linked Toxicity Pathway on Prolonged Exposure to β-amyloid," The Journal of Biological Chemistry, Aug. 28, 2015, vol. 290, No. 35, pp. 21409-21420.

Branchu, J. et al., "Shift from Extracellular Signal-Regulated Kinase to AKT/cAMP Response Element-Binding Protein Pathway Increases Survival-Motor-Neuron Expression in Spinal-Muscular-Atrophy-Like Mice and Patient Cells," The Journal of Neuroscience, Mar. 6, 2013, vol. 33, No. 10, pp. 4280-4294.

Chaput, D., et al., "SILAC-based proteomic analysis to investigate theimpact of amyloid precursor protein expression in neuronal-like B103 cells," Electrophoresis, 2012, vol. 33, No. 24, pp. 3728-3737.

Davies, S., et al., "Stemistry: The Control of Stem Cells in Situ Using Chemistry". J. Med. Chem., 2015, vol. 58, pp. 2863-2894.

Fernandez, M.L. et al., "Differences in MEK inhibitor efficacy in molecularly characterized low-grade serous ovarian cancer cell lines," American Journal of Cancer Research, 2016, vol. 6, No. 10, pp. 2235-2251.

Gartner, U., et al., "Elevated expression of p21ras is an early event in Alzheimer's disease and precedes neurofibrillary degeneration," Neuroscience, 1999, vol. 91, No. 1, pp. 1-5.

Guerra, B., et al., "Plasma membrane oestrogen receptor mediates neuroprotection against b-amyloid toxicity through activation of Raf-1/MEK/ERK cascade in septal-derived cholinergic SN56 cells," J. Neurochem., 2004, vol. 91, pp. 99-109.

Jana, M., et al. Membrane-bound tetramer and trimer Aβ oligomeric species correlate with toxicity towards cultured neurons. J Neurochem., 2016, vol. 136, No. 3, pp. 594-608.

Kim, Y.M., "The MEK1/2 inhibitor AS703026 induces dopaminergic neuron differentiation of neural stem/progenitor cells in vitro and in vivo (Masters dissertation)," Yeonsei University, Seoul, Korea, Aug. 2014, 40 Pages.

Kong, L., et al., "The Coumarin Derivative Osthole Stimulates Adult Neural Stem Cells, Promotes Neurogenesis in the Hippocampus, and Ameliorates Cognitive Impairment in APP/PS1 Transgenic Mice," Biol. Pharm. Bull., 2015, pp. 1290-1301, vol. 38-, No. 9.

Martinelli, E. et al., "Antitumor activity of pimasertib, a selective MEK 1/2 inhibitor, in combination with PI3K/mTOR inhibitors or with multi-targeted kinase inhibitors in pimasertib-resistant human lung and colorectal cancer cells", International Journal of Cancer, 2013, vol. 133, No. 9, pp. 2089-2101.

Mills, J., et al., "Regulation of amyloid precursor protein catabolism involves the mitogen-activated protein kinase signal transduction pathway," J. Neurosci., 1997, vol. 17, pp. 9415-9422.

Murakami, K., Conformation-specific antibodies to target amyloid β oligomers and their application to immunotherapy for Alzheimer's disease. Biosci. Biotechnol. Biochem., 2014, vol. 78, No. 8, pp. 1293-1305.

PCT International Search Report and Written Opinion for PCT/KR2017/013444, dated Feb. 19, 2018, 10 Pages, (With Concise Explanation of Relevance).

Pei, J-J., et al., "Up-regulation of mitogen-activated protein kinases ERK1/2 and MEK1/2 is associated with the progression of neurofibrillary degeneration in Alzheimer's disease," Brain Res Mol Brain Res., 2002, vol. 109, (1-2), pp. 45-55.

Subramaniam, S. et al., "ERK activation promotes neuronal degeneration predominantly through plasma membrane damage and independently of caspase-3," The Journal of Cell Biology, May 10, 2004, vol. 165, No. 3, pp. 357-369.

Tamagno, E., et al., "JNK and ERK1/2 pathways have a dual opposite effect on the expression of BACE1," Neurobiology of Aging, 2009, vol. 30, pp. 1563-1573.

Watson, K., et al., "Macrophage Inflammatory Protein 2 Inhibits β-Amyloid Peptide (1-42)-Mediated Hippocampal Neuronal Apoptosis through Activation of Mitogen-Activated Protein Kinase and Phosphatidylinositol 3-Kinase Signaling Pathways," Molecular Pharmacology, 2005, vol. 67, No. 3, pp. 757-765.

Yahata, N., et al., "Anti-Aβ Drug Screening Platform Using Human iPS Cell-Derived Neurons for the Treatment of Alzheimer's Disease," PLOS One, Sep. 2011, 12 Pages, vol. 6, Isssue 9, e25788.

Zhao, C., et al., "Mechanisms and Functional Implications of Adult Neurogenesis," Cell, 2008, vol. 132, pp. 645-660.

U.S. Office Action, U.S. Appl. No. 15/897,138, dated Sep. 7, 2018, 7 pages.

\* cited by examiner

FIG. 5a
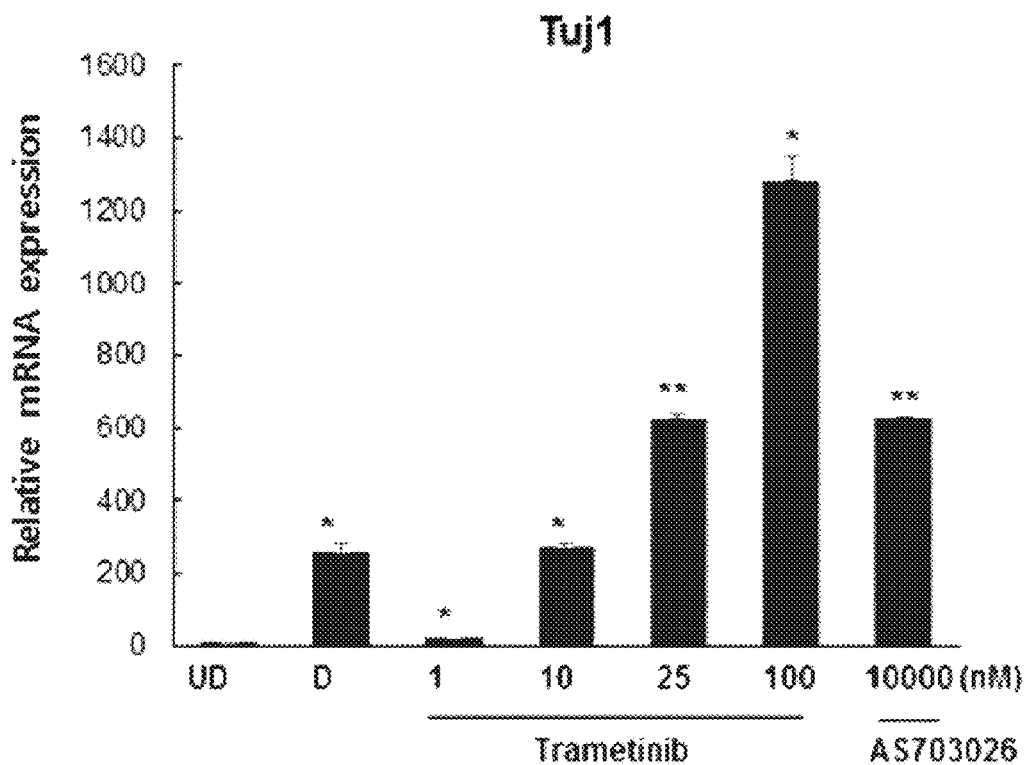
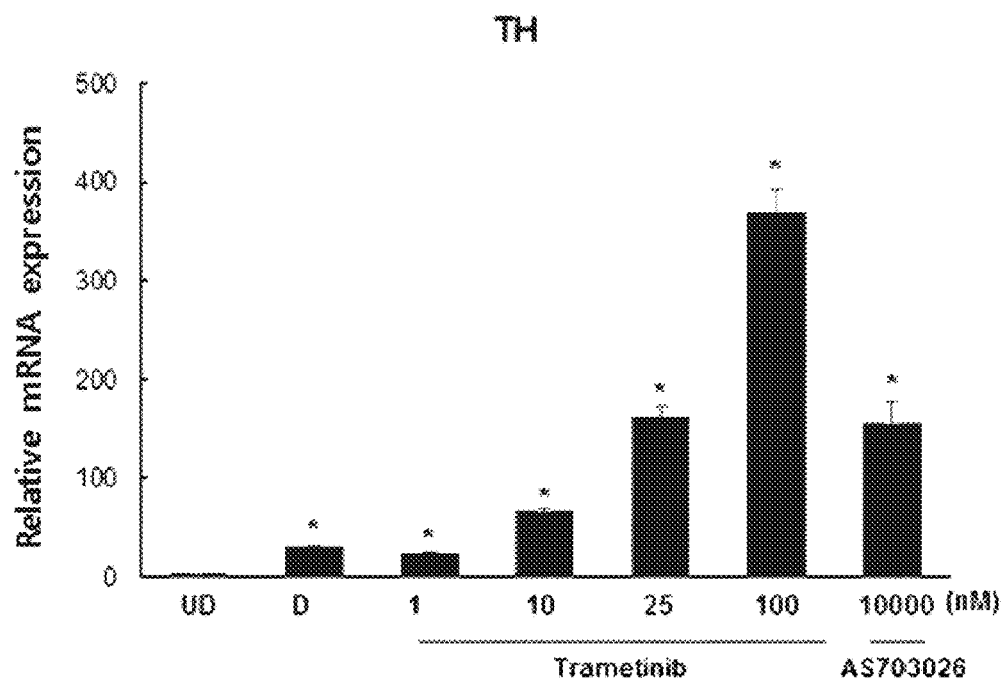
FIG. 5b

FIG. 6a
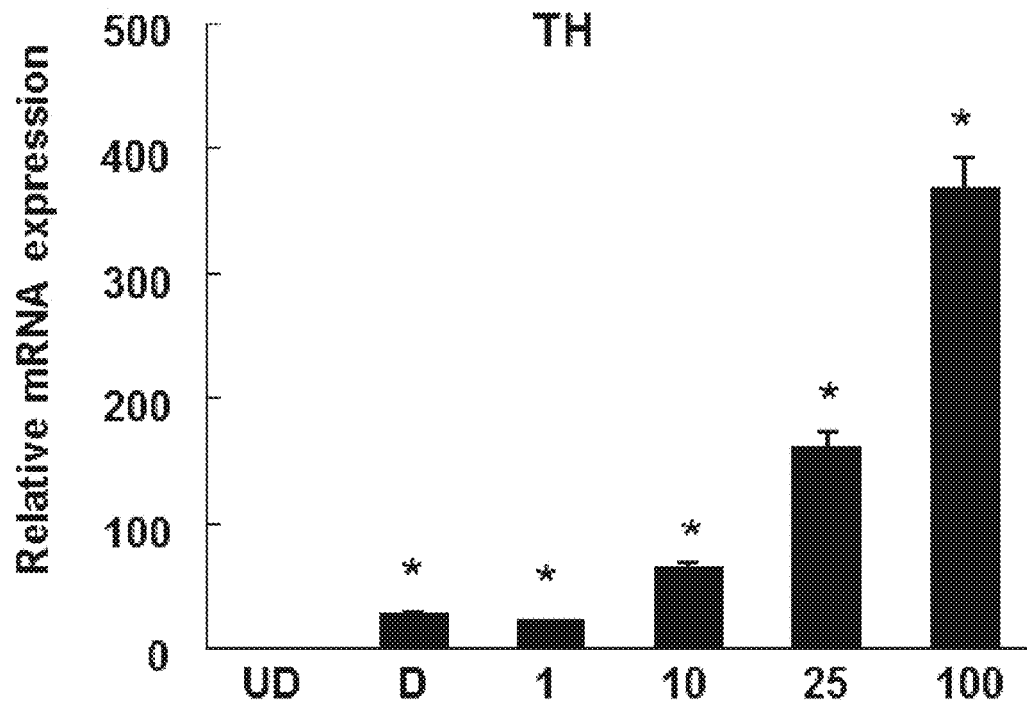
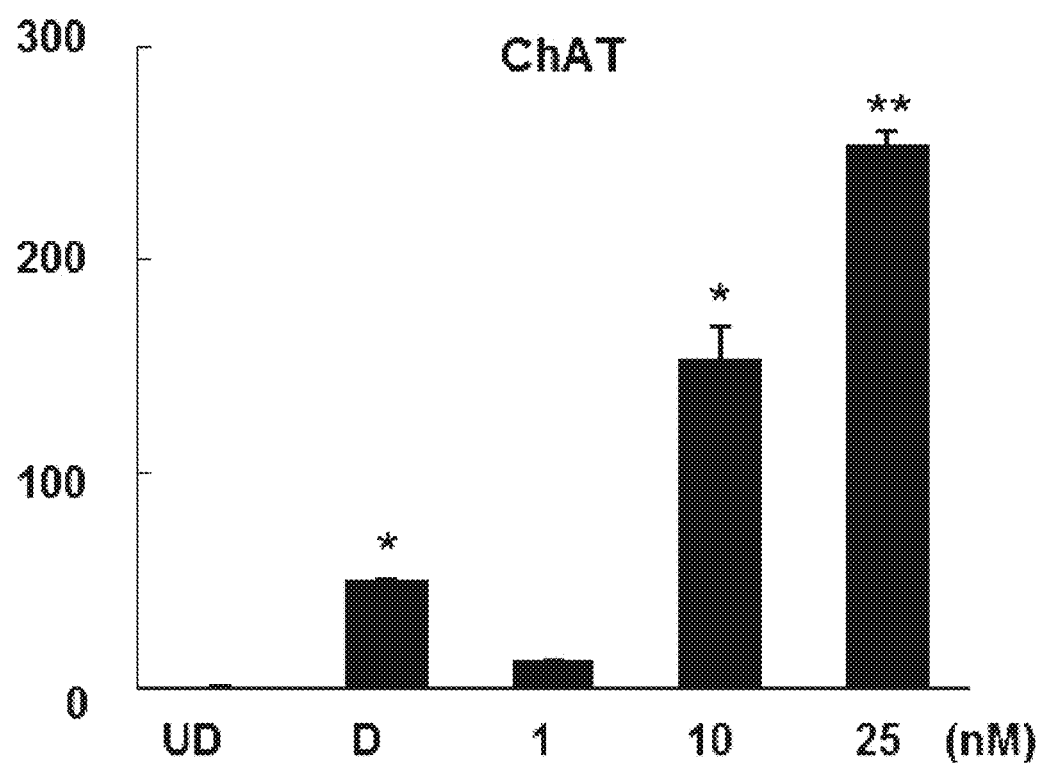
FIG. 6b

FIG. 6c
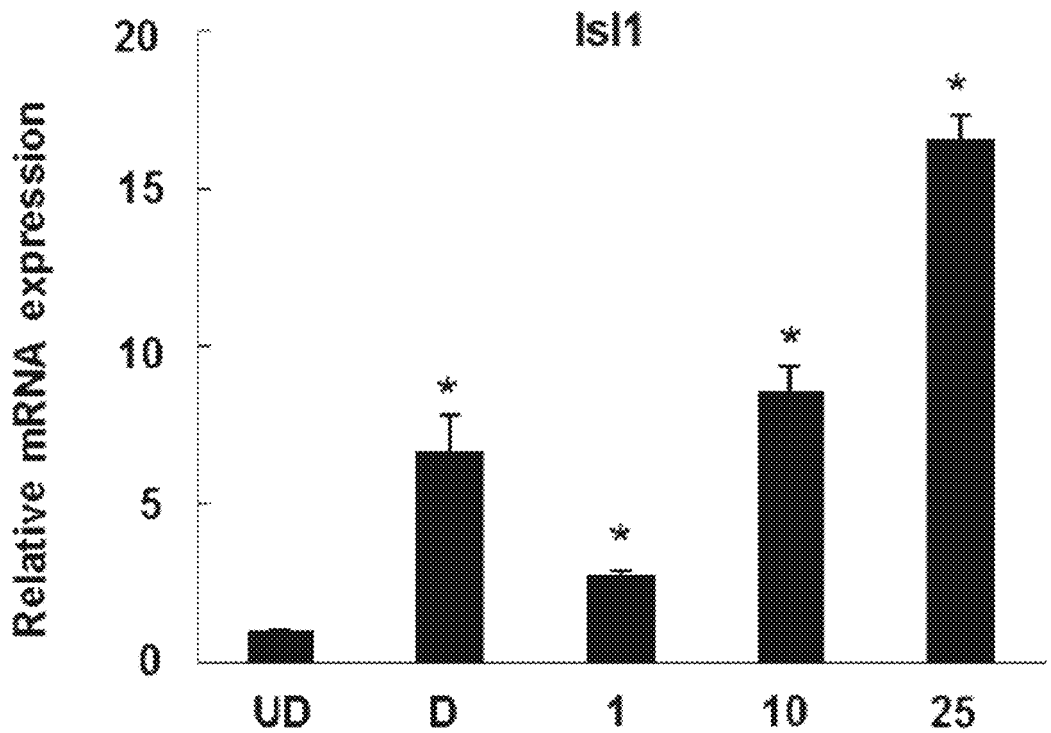
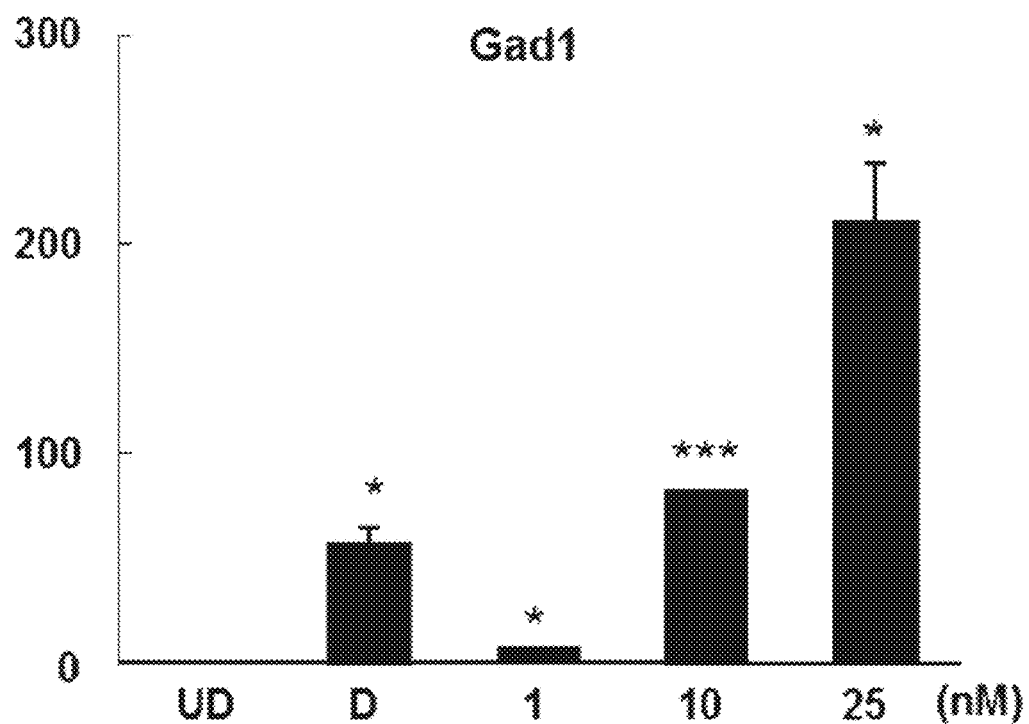
FIG. 6d

FIG. 7c
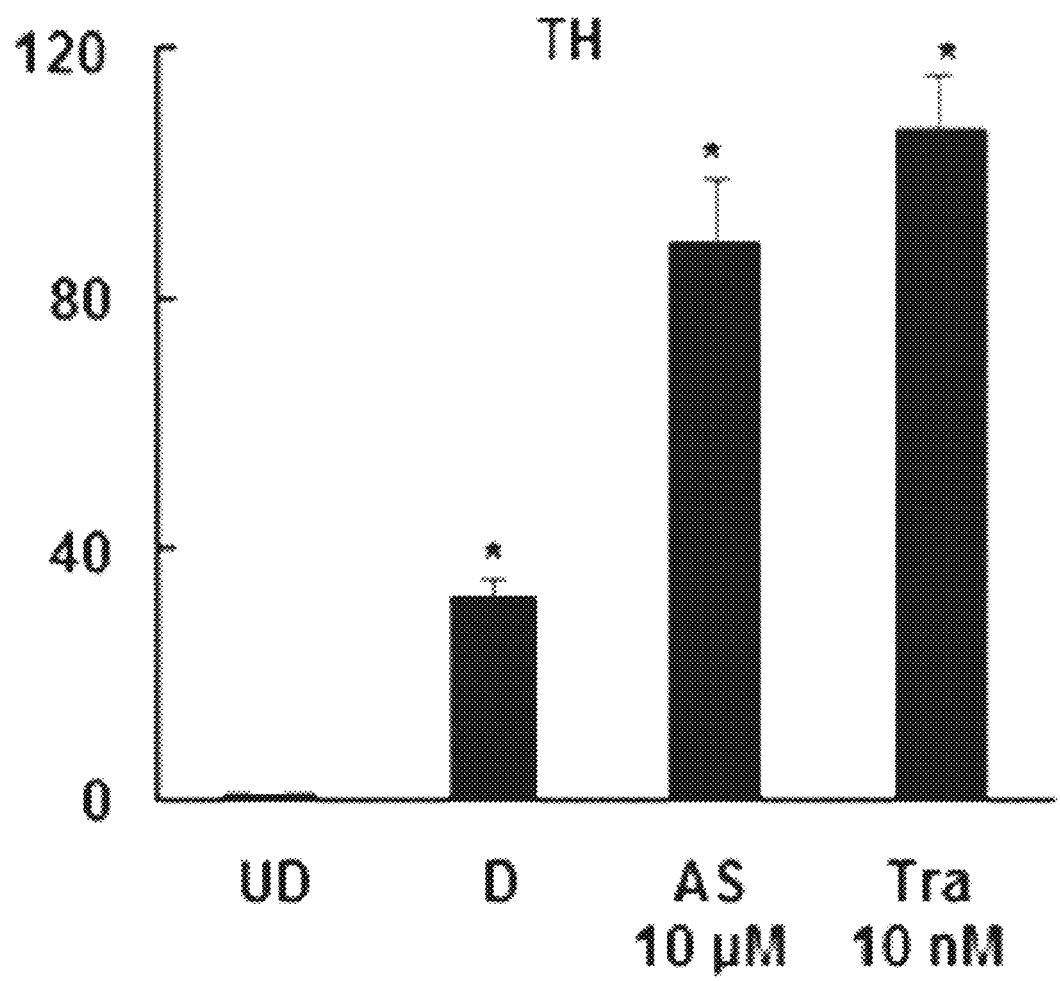
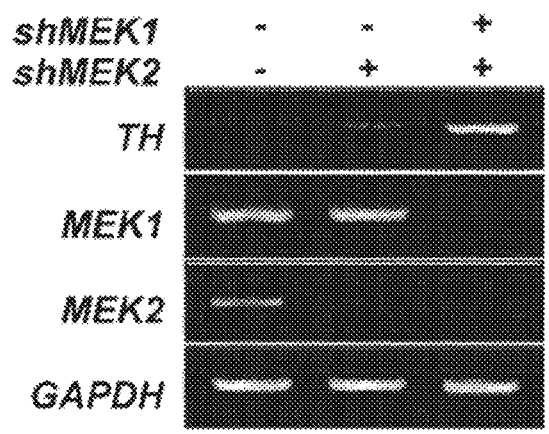
FIG. 8a

SEQUENCE LISTING

```
<160> NUMBER OF SEQ ID NOS: 18

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
```
cgtgccgcct ggagaaacc                                          19

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtctggcgc ctttgga                                            17

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aggtatacgc cacgctgaag                                         20

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tggaagagtg ggagttgctg ttg                                     23

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caccactctg accaaagata aagttg                                  26

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctcgggtgag tgcataggtg                                         20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
cctgccagtc aactctagcc                                                 20

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcatgttatg gaaatcttgc ttcag                                           25

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cggagagaca tgatggtggt                                                 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tacagagagg ctgccctgag                                                 20

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgagtcacag agattggtca tatactact                                       29

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggctgatcta tgtcgctttg c                                               21

<210> SEQ ID NO 13
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ccgggccatc caacattcta gtgaactcga gttcactaga atgttggatg gctttt         57
```

```
<210> SEQ ID NO 14
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ccggcctccg agagaagcac cagatctcga gatctggtgc ttctctcgga ggtttttg      58

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cggcggttaa cgggacca                                                  18

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cctggatgag cagcaaagga                                                20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggattgcggg tttgatctcc a                                              21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cagtgagcca ccatccatgt                                                20
```

COMPOSITION FOR INDUCING DIFFERENTIATION AND PROTECTION OF NEURAL STEM CELLS AND METHOD FOR INDUCING NEURO-REGENERATION USING THE SAME COMPOSITION

CROSS REFERENCE TO RELATED APPLICATIONS

This application is a divisional of U.S. application Ser. No. 15/897,138, filed Feb. 14, 2018, which is a continuation of International Application No. PCT/KR2017/013444, filed Nov. 23, 2017, which claims the right of priority based on Republic of Korea patent application no. 10-2017-0036268, filed Mar. 22, 2017, and Republic of Korea patent application no. 10-2016-0158739, filed Nov. 25, 2016 each of which is hereby incorporated by reference in its entirety.

SEQUENCE LISTING

[0001.1] The instant application contains a Sequence Listing which has been filed electronically in ASCII format and is hereby incorporated by reference in its entirety. Said ASCII copy, created on Oct. 31, 2019, is named 43721US_CRF_sequencelisting.txt and is 4,582 bytes in size.

TECHNICAL FIELD

The present invention relates to a method of inducing neuro-regeneration comprising administering a MEK 1/2 inhibitor to a patient in need thereof and to a composition comprising a MEK1/2 inhibitor for use in the above method. In the present invention, the MEK1/2 inhibitor induces neuro-regeneration by differentiating neural stem cells into neurons, by protecting neural stem cells and neurons against cytotoxicity of amyloid-betas, or by both of the above. Also, the present invention relates to a method of protecting neurons against neuronal loss or damage comprising administering a MEK1/2 inhibitor and to a composition comprising a MEK1/2 inhibitor for use in the above method. In addition, this invention relates to a method of preventing or treating neurodegenerative disease due to neuronal loss or damage for patients in need thereof comprising administering a MEK 1/2 inhibitor and to the composition comprising the MEK1/2 inhibitor for use in the above method.

BACKGROUND ART

Neurodegenerative disease such as Alzheimer's disease (AD) and Parkinson's disease (PD) are prevalent in the elderly population and the number of patients is increasing exponentially with the aging of society. Moreover, reports of early-onset types of neurodegenerative disease in the young are not uncommon. Thus, there is great interest in developing treatments that help stop the progress of the disease or recover damaged brain tissues.

The exact causes of such neurodegenerative disease have not been established yet. According to what is known so far, neuronal cells in specific locations in the brain (e.g. the hippocampus or substantia nigra) are damaged leading to a defective neural network among the reduced number of neuronal cells, which results in various symptoms of the neurodegenerative disease.

Research is being carried out in various fields to look for treatments. To date, drugs related to the relief of symptoms include memantine (NMDA receptor antagonist), L-DOPA (dopamine mimic drug), etc. Other drugs are also limited to a short-term effect or have been found to have side effects with continual use, making it difficult to expect them to provide for treatment beyond the temporary relief of symptoms. Therefore, a fundamental treatment for the cause of neurodegenerative disease is in great need.

Neural stem cells (NSC) and neural progenitor cells (NPC), cells that are capable of differentiating into neural cells, are present in the adult brain. Neural stem cells are present in the subventricular zone of the lateral ventricle and dentate gyrus of the hippocampus, and it is in this region that neurogenesis occurs throughout the entire animal's life through differentiation and proliferation of neural stem cells (Zhao et al. (2008) Mechanisms and Functional Implications of Adult Neurogenesis. Cell 132:645-660).

Since brain neuronal cell damage and loss occur in neurodegenerative disease, replacement of damaged or lost neurons with normal functioning neurons through the stimulation of NSCs and NPCs could be a fundamental treatment for neurodegenerative disease. This method of treatment includes the method of stem cell treatment, where NSCs and NPCs are isolated from the patient's body, stimulated in vitro to differentiate into neurons, and then transplanted back into the patients. However, there is difficulty in isolating NSCs and NPCs from patients and then transplanting them back into patients. Also, the transplanted NSCs and NPCs quickly lose their activity in the brain, requiring repeated transplantations. As an alternative, instead of transplanting neural stem cells into patients, a method of generating neurons in the patient's brain by stimulating NSCs and NPCs to differentiate with the use of drugs has recently been proposed (Davies et al. (2015) Stemistry: The Control of Stem Cells in Situ Using Chemistry. J. Med. Chem. 58:2863-2894).

Amyloid-beta (Aβ) is a peptide of 36-43 amino acids, which is produced by the cleavage of the amyloid precursor protein (APP), a type 1 integral membrane protein, by β-secretase and γ-secretase. Amyloid-beta (Aβ) aggregates as soluble amyloid-beta (Aβ) oligomers and then, via protofibrils, forms insoluble Aβ fibrils to eventually accumulate as amyloid plaques in the brain. The deposition of Aβ in the brain is associated with synapse damage, neuronal damage, and brain atrophy and ultimately results in damage in memory and cognitive functions, two very typical symptoms of Alzheimer's disease (AD). Among the various forms of Aβ, soluble Aβ oligomers, especially trimers and tetramers, are thought to be the most toxic forms of Aβ that are associated with neuronal dysfunction and synaptic damage (Murakami, (2014) Conformation-specific antibodies to target amyloid β oligomers and their application to immunotherapy for Alzheimer's disease. Biosci. Biotechnol. Biochem. 78(8):1293-1305; Jana et al. (2016) Membrane-bound tetramer and trimer Aβ oligomeric species correlate with toxicity towards cultured neurons. J Neurochem. 136 (3):594-608).

Therefore, protecting neurons from Aβ, especially the oligomeric forms of Aβ, is considered the potential target for AD treatment. However, AD patients have already undergone significant neuronal damage, so in addition to neuro-protection, neuro-regeneration through the differentiation of endogenous neural stem cells is required for the fundamental treatment of AD.

MEK (mitogen-activated protein kinase kinase; also known as MAP2K or MAPKK) is a member of the MAP kinase (mitogen-activated protein kinase; MAPK) signal transduction pathway (written herein as 'MAPK/ERK pathway') that follows in the sequence of Ras-Raf-MEK-ERK.

When various signaling molecules such as growth factors, hormones, cytokines, etc., bind to cell membrane receptors and activate receptor tyrosine kinase, the protein Ras GTPase is activated, which results in the recruitment of cytoplasmic Raf to the cell membrane. Activated Raf phosphorylates and activates MEK and ERK, sequentially, and activated ERK in turn translocates into the nucleus to activate various transcription factors. These transcription factors then bind to the promoters of various genes to control cell proliferation, differentiation, and survival. Because the MAPK/ERK signal transduction pathway is hyperactivated in tumor cells, the kinases were seen as important targets to inhibit the disease progress in cancer and other proliferative disease.

There are 7 proteins (MEK1-MEK7) known to be in the MEK family and of these, only MEK1 and MEK2 are involved in the signal transduction of the Ras-Raf-MEK-ERK pathway. Although MEK1 and MEK2 are encoded by different genes, they share high homology (80%) both within the C-terminal catalytic kinase domains and most of the N-terminal regulatory regions. Although oncogenic forms of MEK1 and MEK2 have not been found in human cancers, it is known that constitutive activation of MEK has been shown to result in cellular transformation. In addition, MEK can also be activated by other oncogenes. Accordingly, the inhibition of MEK1 and MEK2 has been studied as a target for anticancer drug development. It is unclear, however, what role MEK1 and MEK2 and the MAPK/ERK pathway have on the proliferation and differentiation of adult neural stem cells.

Furthermore, there are study results that indicate a link between the MAPK/ERK pathway and Aβ or tau proteins in the brain of Alzheimer's (AD) patients. Unfortunately, it is unclear whether AD treatment will require the activation or the inhibition of this signaling pathway and whether or not the control of this signal transduction pathway can be linked to AD treatment.

There are reports of increased levels of expression of proteins in the MAPK/ERK pathway in patients of very early stage Alzheimer's disease (Arendt et al. (1995) Increased Expression and Subcellular Translocation of the Mitogen-Activated Protein Kinase Kinase and Mitogen-Activated Protein Kinase in Alzheimer's Disease. Neuroscience 68(1):5-18; Gartner et al. (1999) Elevated Expression of p21ras is an Early Event in Alzheimer's Disease and Precedes Neurofibrillary Degeneration. Neuroscience 91(1); 1-5), of the association between ERK1/2 and MEK1/2 with the hyperphosphorylation of tau in Alzheimer's patient brain (Pei et al. (2002) Up-Regulation of Mitogen-Activated Protein Kinases ERK1/2 and MEK1/2 is Associated with the Progression of Neurofibrillary Degeneration in Alzheimer's Disease. Brain Res Mol Brain Res. 109(1-2):45-55), and of increased Ras expression and ERK1/2 activation in B103 cells (mouse neuroblastoma cells) expressing amyloid precursor protein (APP) (Chaput et al. (2012) SILAC-based Proteomic Analysis to Investigated the Impact of Amyloid Precursor Protein Expression in Neuronal-Like B103 Cells. Electrophoresis 33(24):3728-3737).

Meanwhile, other studies have shown that when ERK1/2 is activated, apoptosis induced by Aβ is inhibited and Aβ accumulation decreases (Guerra et al. (2004) Plasma Membrane Oestrogen Receptor Mediates Neuroprotection Against β-Amyloid Toxicity Through Activation of Raf-1/MEK/ERK Cascade in Septal-Derived Cholinergic SN56 Cells. J. Neurochem. 91:99-109; Watson et al. (2005) Macrophage Inflammatory Through Activation of Mitogen-Activated Protein Kinase an Phosphatidylinositol 3-Kinase Signaling Pathway. Molecular Pharmacology 67(3):757-765; Mills et al. (1997) Regulation of Amyloid Precursor Protein Catabolism Involves the Mitogen-Activated Protein Kinase Signal Transduction Pathway. J. Neurosci. 17:9415-9422). In addition, it has been reported that ERK1/2 decreases the activity of γ-secretase, which produces Aβ from APP, and decreases the expression and activity of BACE1(β-secretase1) in oxidative stress conditions (Tamagno et al. (2009) JNK and ERK1/2 Pathways Have a Dual Opposite Effect on the Expression of BACE1. Neurobiology of Aging 30:1563-1573).

Therefore, there are conflicting views on the roles of the MAPK/ERK pathway regulation and MEK inhibition in relation to neurodegenerative diseases, such as Alzheimer's disease, which have yet to be clearly elucidated.

DISCLOSURE OF INVENTION

Technical Problem

The inventors of the present invention are to provide a method of inducing neuro-regeneration by differentiating neural stem cells into neurons and protecting neural stem cells and neurons from Aβ with a compound inhibiting both MEK1 and MEK2. In addition, the inventors are to provide a method of protecting neurons against neuronal loss or damage and a method of preventing or treating neurodegenerative disease due to neuronal loss or damage with the compound inhibiting both MEK 1 and MEK2.

Solution to Problem

The present inventors have discovered that the compound that inhibits both MEK1 and MEK2 (herein called "MEK 1/2 inhibitor"), specifically, the compound represented by [Formula 1] can effectively induce the differentiation of neural stem cells into neurons; more specifically, it protects neural stem cells and neurons against amyloid-beta at the same time it induces the differentiation of neural stem cells into neurons.

[Formula 1]

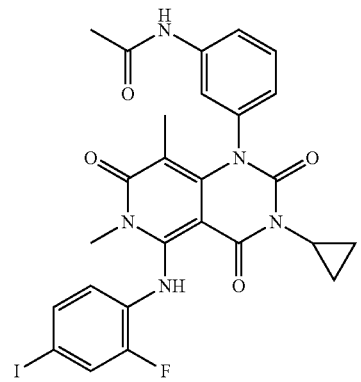

One aspect of the present invention relates to the neural stem cell differentiation-inducing composition comprising the compound of [Formula 1]. The composition does not illicit cancerous growth in neural stem cells.

The neural stem cell differentiation-inducing composition induces the differentiation of neural stem cells into neurons, even in the presence of amyloid-beta.

The induction of neuron differentiation by the neural stem cell differentiation-inducing composition may be the result of inhibition of both MEK1 and MEK2.

The present composition may include a specific MEK 1/2 inhibitor other than compound of [Formula 1]. This composition induces the differentiation of neural stem cells into neurons even in the presence of amyloid-beta.

Another aspect of the present invention relates to the method of differentiating neural stem cells into neurons using the neural stem cell differentiation-inducing composition.

The differentiation method may consist of treating neural stem cells with the neural stem cell differentiation-inducing composition and allowing 1 to 7 days for the completion of differentiation.

Another aspect of the present invention relates to the compound of [Formula 1] for use in inducing the differentiation of neural stem cells, specifically for use in the protection of neural stem cells and neurons and differentiation of neural stem cells into neurons even in the presence of amyloid-beta. Yet another aspect of the present invention relates to a specific MEK 1/2 inhibitor for use in inducing the differentiation of neural stem cells, specifically for use in the protection of neural stem cells and neurons and differentiation of neural stem cells into neurons even in the presence of amyloid-beta.

Another aspect of the present invention relates to a kit for use in inducing the differentiation of neural stem cells into neurons in vitro. This kit may include the neural stem cell differentiation-inducing composition, culture media, plates, coating solutions, and additives needed for culturing cells such as growth factors, etc.

Another aspect of the present invention relates to a method of inducing neuro-regeneration comprising administering a specific MEK 1/2 inhibitor to a patient in need thereof. In the present invention, the MEK 1/2 inhibitor induces neuro-regeneration by differentiating neural stem cells into neurons, by protecting neural stem cells and neurons against cytotoxicity of amyloid-betas, or by both of the above. The most preferable MEK 1/2 inhibitor for this method is the compound of [Formula 1]. An additional aspect of the present invention relates to the specific MEK 1/2 inhibitor, specifically the compound of [Formula 1], for use in inducing neuro-regeneration.

Another aspect of the present invention relates to a method of protecting neurons against neuronal loss or damage comprising administering a specific MEK 1/2 inhibitor to a patient in need thereof. The most preferable MEK 1/2 inhibitor for this method is the compound of [Formula 1]. An additional aspect of the present invention relates to the specific MEK 1/2 inhibitor, specifically the compound of [Formula 1], for use in protecting neurons against neuronal loss or damage.

Another aspect of the present invention relates to a pharmaceutical composition comprising the compound of [Formula 1] as its active ingredient for the prevention or treatment of neurodegenerative diseases or the method of prevention or treatment of neurodegenerative diseases using the compound of [Formula 1].

Neurodegenerative disease pertains to functional disorders in various systems such as motor control, cognition, perception, sensory function, and the autonomic nervous system due to the loss or decrease in neuronal function. Examples of neurodegenerative diseases include dementia, Alzheimer's disease (AD), vascular dementia, senile dementia, frontotemporal dementia (FTD), Lewy body dementia (LBD), Parkinson's disease (PD), multiple system atrophy (MSA), corticobasal degeneration(CBD), progressive supranuclear palsy (PSP), Huntington's disease (HD), amyotrophic lateral sclerosis (ALS, Lou-Gehrig's disease), primary lateral sclerosis (PLS), progressive bulbar palsy (PBP), progressive muscular atrophy (PMA), pseudobulbar palsy, hereditary spastic paraplegia (HSP), cerebellar ataxia, Creutzfeldt-Jakob disease (CJD), multiple sclerosis (MS), Guillain-Barré syndrome (GBS), etc.

The pharmaceutical composition or method may include or use another specific MEK1/2 inhibitor other than the compound of [Formula 1].

An additional aspect of the present invention relates to the compound of [Formula 1] for use in the prevention and treatment of neurodegenerative disease. In addition, it relates to the specific MEK 1/2 inhibitor for use in the prevention and treatment of neurodegenerative disease.

Another aspect of the present invention relates to a method of screening for compounds that induce the differentiation of neural stem cells into neurons and protect them in neurodegenerative disease simulated environments such as Alzheimer's disease. The screening method according to the present invention comprises the steps of:

1) treating neural stem cells isolated from adult mouse with neuron damage-inducing substances such as amyloid-beta (specifically in its oligomeric form), MPTP (1-methyl-4-phenyl-1,2,3,6-tetrahydropyridine), rotenone, oxidopamine, glutamate, LPS (lipopolysaccharide), S100B (S100 calcium-binding protein B);

2) adding a test material to the neural stem cells treated with the above neuron damage-inducing substances; and 3) examining the differentiation or death of the neural stem cells by morphology analysis.

In the following, various aspects and embodiments of the present invention will be described in detail.

As used herein in the present invention, "neural stem cells" refers to having the ability to continually proliferate in the undifferentiated state (self-renewal) and the ability to differentiate into various neurons and glia from one stem cell (multipotency). The neural stem cell is of animal origin. The term animal not only refers to human and primates, but is intended to include animals such as cows, pigs, sheep, horses, mice, rats, cats, etc., and preferably, humans. In instances, the term "neural stem cell" is used to include "neural progenitor cell".

As used herein in the present invention, the term "differentiation" refers to the development of a cell into a specialized cell. More specifically, it refers to the phenomenon in which the structure or function of the cell becomes specialized through cell division, proliferation, and growth of the cell and to the changes in the structure (morphology) or function of the cells and tissues in order to perform the tasks assigned to them. The differentiation of neural stem cells is preceded by the asymmetric division of the mother cell into two cells that have different properties. One of the daughter cells is the same as the mother cell, remaining as the stem cell, and the other differentiates into a specialized cell. The fact that this kind of asymmetric division process accompanies neural stem cell differentiation signifies that "differentiation of neural stem cell" encompasses the meaning of "proliferation".

As used herein in the present invention, the term "proliferation" refers to the phenomenon in which a cell divides and proliferates. This specifically refers to the increase in the same type of cells through cell division, the increase in the number of cells through the reproduction of the exact same form of cells.

As used herein in the present invention, the term "protection" refers to preventing cells from being damaged by harmful external stimuli so that neural stem cells can proliferate or differentiate without undergoing cell death, and the differentiated neurons can survive in the presence of cytotoxic factors, specifically, amyloid-beta. In connection to AD, the term "protection" in the present invention includes the aspect that neural stem cells and neurons are protected against damage caused by amyloid-beta through the lowering of the Aβ(1-42)/Aβ(1-40) ratio in the brain (Majid et al. (2015) Pharmacologic Treatment with Histone Deacetylase 6 Inhibitor (ACY-738) Recovers Alzheimer's Disease Phenotype in Amyloid Precursor Protein/Presenilin 1 (APP/PS1) Mice. Alzheimers Dement. 170-181; Borchelt et al. (1996) Familial Alzheimer's Disease-Linked Presenilin 1 Variants Elevate Aβ1-42/1-40 Ratio In Vitro and In Vivo. Neuron. 17:1005-1013).

As used herein in the present invention, the term "prevention" refers to all activities that inhibit or delay the progress of neurodegenerative diseases through the administration of the pharmaceutical composition according to the present invention. "Treatment" refers to all activities that alleviate symptoms or improve the disease state in suspected or diagnosed neurodegenerative patients.

One aspect of the present invention relates to the neural stem cell differentiation-inducing composition comprising the compound represented as [Formula 1].

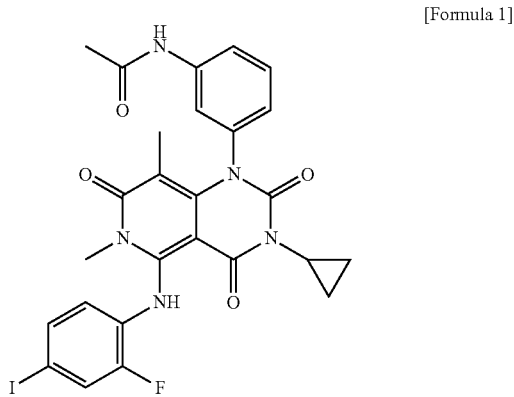 [SMILES: CC(=O)Nc1cccc(-n2c(=O)n(C3CC3)c(=O)c3c(Nc4ccc(I)cc4F)n(C)c(=O)c(C)c32)c1]

[Formula 1]

The common name of the compound represented above as [Formula 1] is trametinib and its chemical name is N-(3-{3-cyclopropyl-5-[(2-fluoro-4-iodophenyl)amino]-6,8-dimethyl-2,4,7-trioxo-3,4,6,7-tetrahydropyrido[4,3-d]pyrimidin-1(2H)-yl}phenyl)acetamide. It is disclosed in Example 4-1 of WO2005/121142, the applicant of which is Japan Tobacco Inc. The compound of [Formula 1] inhibits both MEK1 and MEK2, the upstream components of ERK in the MAPK/ERK (mitogen-activated protein kinase/extracellular regulated kinase) signal transduction pathway. This compound is used as a cancer drug for melanoma and non-small cell cancer. In the present invention, it is used in the form of a free base or a pharmaceutically acceptable salt or solvate. Examples of possible solvates are hydrates, dimethyl sulfoxide, acetic acid, ethanol, nitromethane, chlorobenzene, 1-pentanol, isopropyl alcohol, ethylene glycol, 3-methyl-1-butanol, etc.

In particular, one aspect of the present invention relates to a composition comprising the compound of [Formula 1], which both protects neural stem cells and neurons and differentiates neural stem cells into neurons. Amyloid-beta accumulates in the brain as amyloid plaques, is associated with synaptic damage, neuronal damage, and brain atrophy, and is known to ultimately cause the typical symptoms of Alzheimer's disease, memory and cognitive dysfunction. Therefore, protecting neural stem cells and neurons against amyloid-beta while regenerating neurons through the differentiation of endogenous neural stem cells may constitute a fundamental treatment for Alzheimer's disease.

Aβ(1-42) which consists of 42 amino acids has a higher tendency to form aggregates than Aβ(1-40) and a higher tendency to form the more toxic trimers or tetramers and is thus considered to be strongly associated with the pathologic state of Alzheimer's disease. Therefore, the composition that can protect and differentiate neural stem cells even in the presence of Aβ(1-42), especially Aβ(1-42) oligomers, is preferable.

As shown in the test examples, with the purpose of finding a composition that induces the differentiation of mouse neural stem cells into neurons, the inventors have confirmed that compound of [Formula 1] is very effective in inducing the differentiation of neural stem cells isolated from mouse embryonic or adult brain into neurons.

Neural stem cells have the ability to differentiate into various neurons or into glia, such as oligodendrocytes, astrocytes, and microglia. Compound of [Formula 1] differentiates neural stem cells mostly into neurons and limits the differentiation into glia. Therefore, compound of [Formula 1] can effectively induce the generation of neurons (neurogenesis), thereby allowing the replacement of damaged neurons with these "new" neurons in the brain of neurodegenerative disease patients with neuronal damage, and can be used as a drug that promotes neural regeneration or neuro-regeneration.

According to the specific examples of the present invention, the inventors have established through oligomeric Aβ-treated in vitro experiments that simulate the brain environment of Alzheimer's patients that compound of [Formula 1] protects against death of neural stem cells or neurons, and induces the differentiation of neural stem cells into neurons (FIG. 2)

Additionally, one aspect of the present invention relates to the neural stem cell differentiation-inducing composition comprising a specific compound that inhibits both MEK1 and MEK2. In this invention, the compound that inhibits both MEK1 and MEK2 is also called "MEK 1/2 inhibitor". "MEK 1/2 inhibitor" preferably has an IC50 value in the nM level and a difference of less than 10× in the IC50 values of MEK1 and MEK2, preferably less than 5×. The IC50 for MEK1 and 2 can be measured by methods in references such as [Yamaguchi et al. (2011) International Journal of Oncology 39:23-31]. The MEK 1/2 inhibitor that may be used in the present invention is a compound that induces the differentiation of neural stem cells into neurons while protecting the neural stem cells and neurons against toxic materials such as Aβ. Examples of MEK 1/2 inhibitors that may be used in the present invention are as follows: trametinib, pimasertib(AS703026), AZD8330, binimetinib (MEK162, ARRY-162, ARRY-438162), refametinib (RDEA119, Bay 86-9766), PD318088, PD0325901, RO5126766.

The chemical structure of the preferred MEK 1/2 inhibitors and their IC50 values and the references describing the methods of measuring the IC50 values are listed as follows:

| Name | Chemical Structure | IC50 value for MEK 1, MEK2 (References for the method of measuring IC50 values) |
|---|---|---|
| Trametinib | 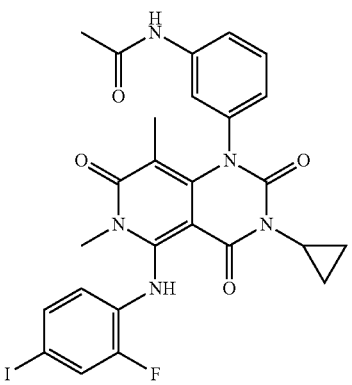 [SMILES: CC(=O)Nc1cccc(-n2c(=O)n(C3CC3)c(=O)c3c(Nc4ccc(I)cc4F)n(C)c(=O)c(C)c32)c1] | 0.92~3.4 nM (International Journal of Oncology 2011; 39: 23-31) |
| Pimasertib (AS703026) | 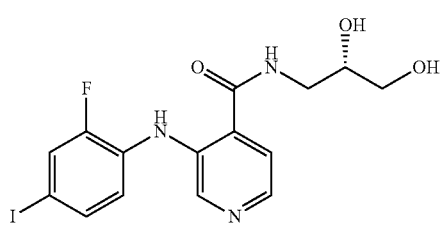 [SMILES: O=C(NC[C@H](O)CO)c1ccncc1Nc1ccc(I)cc1F] | ≤1 μM (US 2009/0093462, Table I, Example 115) |
| AZD8330 | 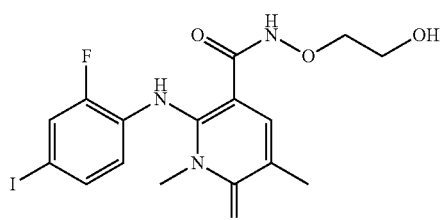 | 7 nM (AACR Annual Meeting, 2009, Abst 3696) |
| Binimetinib (ARRY-162, ARRY-438162) | 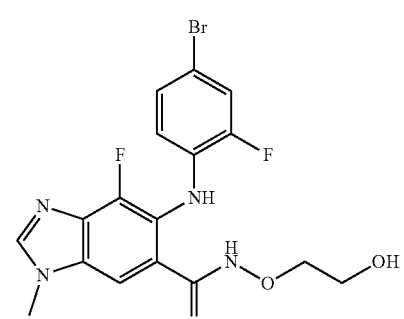 | 12 nM (American College of Rheumatology, 2006 Annual Scientific Meeting, Abst 794) |
| Refametinib (RDEA119, Bay 86-9766) | 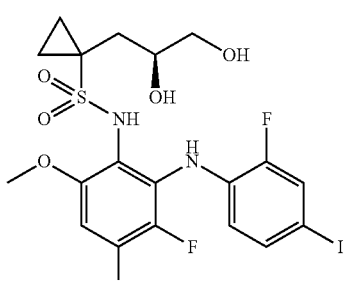 | MEK1: 19 nM, MEK2: 47 nM (Cancer Res. 2009; 69(17): 6839-47) |

| Name | Chemical Structure | IC50 value for MEK 1, MEK2 (References for the method of measuring IC50 values) |
|---|---|---|
| PD318088 | 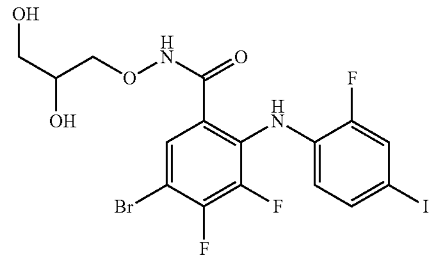 [SMILES: O=C(NOCC(O)CO)c1cc(Br)c(F)c(F)c1Nc1ccc(I)cc1F] | 1.4 nM (WO 02/06213, Example 40) |
| PD0325901 | 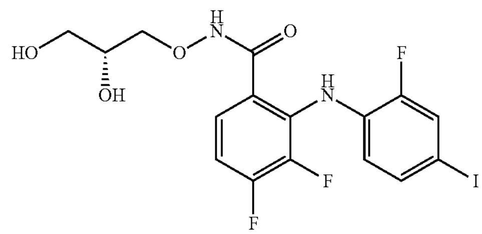 [SMILES: O=C(NOC[C@H](O)CO)c1ccc(F)c(F)c1Nc1ccc(I)cc1F] | 3.6~24 nM (Oncotarget 2012; 3: 1533-1545) |
| RO5126766 (CH5126766) | 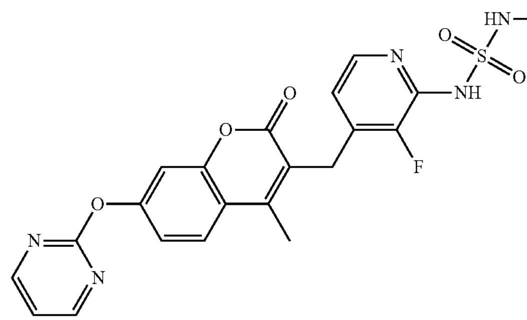 | 160 nM (Cancer Res. 2013; 73(13): 4050-4060) |

In addition, one aspect of the present invention relates to a composition comprising a MEK 1/2 inhibitor for differentiating the neural stem cells into neurons while protecting neural stem cells and neurons against amyloid-beta, especially the oligomeric Aβ(1-42) form.

Using a selective inhibitor for either MEK1 or MEK2, not the MEK 1/2 inhibitor that inhibits both MEK1 and MEK2, is not desirable since its neural stem cell differentiation-inducing activity is weak. For example, cobimetinib is a MEK1-selective inhibitor that shows 100× or greater selectivity toward MEK1 compared with MEK2 (MEK1 IC50=0.95 nM, MEK2 IC50=199 nM; Molecules 2017;22: 1551). Unlike the MEK 1/2 inhibitor, cobimetinib does not induce the differentiation of mouse adult neural stem cells even at a high concentration of 10 M, regardless of whether or not amyloid-beta was treated (Example 7).

Also, the fact that inhibition of both MEK1 and MEK2 is involved in inducing NSC differentiation into neurons and protecting NSC and neurons was confirmed by experiments in Example 5. These experiments used shRNA (short Hairpin RNA) to inhibit MEK1 and MEK2 expression and used plasmids with constitutively active MEK1 (CAMEK1) and constitutively active MEK2 (CAMEK2) to activate MEK1 and MEK2 expression (Example 5).

However, not all MEK 1/2 inhibitors show the same effect. For example, MEK 1/2 inhibitors U0126, PD184352, and BI847325 showed weak neural stem cell (NSC) to neuron differentiation-inducing effects or caused cytotoxicity, rendering them unsuitable to use as the neural stem cell differentiation-inducing composition of the present invention (FIG. 10a and FIG. 10c). Therefore, the NSC to neuron differentiation-inducing activity or NSC and neuron protection activity can differ depending on the different unique properties the compound has other than its MEK 1/2 inhibiting activity. In the present invention, the MEK 1/2 inhibitors that showed NSC to neuron differentiation-inducing activity or NSC and neuron protection activity are trametinib, pimasertib(AS703026), AZD8330, binimetinib, refametinib, PD318088, PD0325901, and RO5126766.

In particular, compound of [Formula 1] (trametinib) showed markedly superior differentiation and protection against Aβ capabilities even when compared to the other MEK1/2 inhibitors that may be used in the present invention. For example, compound of [Formula 1] showed markedly superior differentiation and protection against Aβ capabilities compared with AS703026 at 100× or greater lower concentration. This effect of compound of [Formula 1] is markedly superior to just the predicted effect of its MEK1/2 inhibitory activity.

Compound of [Formula 1] has never been used for the purpose of inducing the differentiation of neural stem cells into neurons and has only been known as a MEK 1/2 inhibitor that inhibits the activities of both MEK1 and MEK2 through ATP non-competitive binding and as melanoma and non-small cell cancer treatment drugs.

Another aspect of the present invention relates to the method of inducing the differentiation of NCS into neurons using the compound of [Formula 1] or other MEK1/2 inhibitors.

As for the method disclosed in the present invention, neural stem cells may be isolated from embryonic or adult brain according to known methods. Alternatively, neural stem cells may be purchased from the market or may be cultured by any conventional method known in the art. There is no particular restriction as to the above. In the Examples section that follows, neural stem cells isolated from the frontal lobes of day 14.5 mouse embryos and the subventricular zone of week 8 mice were used.

Before differentiation, the neural stem cells may be inoculated into a culture medium and cultured at 37° C. The culture medium may be any growth factor supplemented serum-free medium with no particular restrictions. The medium may be, for example, Dulbecco's Modified Eagle's Medium/Nutrient Mixture F12 (DMEM/F12)(1:1) with the addition of one or more medium components selected from the group consisting of 90-110 µM putrescine, 20-40 nM selenite, 10-30 nM progesterone, 1.0-2.0 mg/ml d-(+) glucose, 20-30 µg/ml insulin, 0.05-0.2 mg/ml apo-transferrin, 0.3-0.6 mM Glutamax, 50-150 IU/ml penicillin, and 50-150 µg/ml streptomycin, and with the further addition of growth factor selected from the group consisting of 10-30 ng/ml bFGF, 10-30 ng/ml EGF, or mixtures thereof.

The neural stem cells may be cultured in growth factor supplemented N2 medium [Dulbecco's Modified Eagle's Medium (DMEM/F12 (1:1) supplemented with 100 µM putrescine, 30 nM selenite, 20 nM progesterone, 1.55 mg/ml d-(+)-glucose, 25 µg/ml insulin, 0.1 mg/ml apo-transferrin, 0.5 mM Glutamax, 100 IU/ml penicillin, and 100 µg/ml streptomycin)] to obtain undifferentiated neural stem cells.

The differentiation of cultured neural stem cells into neurons involves the treatment of neural stem cells with the differentiation-inducing composition comprising the compound of [Formula 1] and then allowing for differentiation according to a method known in the art. For example, the neural stem cell differentiation-inducing composition of the present invention is added to the medium containing the cultured neural stem cells, and differentiation is induced at 37° C.

Neural stem cells differentiate into neurons through a process of differentiation under the various culture conditions mentioned above (e.g., the contents and quantity of the medium components and the culture period). The culture conditions are not particularly limited to the conditions mentioned above. Preferably, the culture temperature is from 35° C. to 40° C., at which the differentiation of the neural stem cells can be induced. If the culture temperature is lower than 35° C. or exceeds 40° C., the neural stem cells undergo cell death before differentiating into neurons.

Before the neural stem cell differentiation-inducing composition comprising the compound of [Formula 1] is added, it is preferable to ensure a sufficient concentration of cells in the neural stem cell culture. In addition, to observe changes in the culture such as cell proliferation, differentiation, or death, it is preferable to treat the neural stem cells with the neural stem cell differentiation-inducing composition comprising the compound of [Formula 1] by the above-described method within a culture period of 7 days or less. To this end, the culture period of the neural stem cells is preferably at least 1 day to a maximum of 7 days to ensure a sufficient concentration of cells.

As for the concentration of the compound of [Formula 1], it is preferable to add it to the neural stem cells at a concentration of 1 nM to 20 µM. If the concentration is less than 1 nM, the neural stem cell differentiation-inducing ability is reduced, if it is greater than 20 µM, cell cytotoxicity becomes a problem. For the addition of the compound, neural stem cells are typically seeded into the plate wells to cover up to 70-80% of the surface of the well. For example, 1×105 cells/well are seeded into 12 well plates, 5×105 cells/well for 6 well plates.

Furthermore, as it will be later explained in the Examples section, it is preferable to use the compound of [Formula 1] at a concentration of 10 nM to 10 µM, more preferably, 10 nM to 100 nM. If the concentration is less than 10 nM, the time it takes to induce differentiation increases, which is uneconomical. However, if it is greater than 10 µM, the compound of [Formula 1] as an active ingredient becomes in excess, and upon subsequent in vivo administration, the inhibition of MEK1 and MEK2 may become too strong, may affect many intracellular signaling pathways, and as a result, may induce many unwanted reactions.

After the addition of the neural stem cell differentiation-inducing composition comprising the compound of [Formula 1] which is an inhibitor to both MEK1 and MEK2 to the neural stem cell culture, it takes 1 to 7 days, preferably about 3 to 5 days, for the differentiation process to complete.

Advantageous Effect of Invention

When the neural stem cell differentiation-inducing composition of the present invention is applied to patients with neurodegenerative disease, it induces the neural stem cells in the patient's brain to differentiate into neurons and allows the replacement of damaged or lost neurons by the "newly made" neurons. That is, the composition of the present invention induces neural regeneration or neuro-regeneration through neurogenesis from neural stem cells. Therefore, the composition can be used for the prevention or treatment of neurodegenerative diseases. In the present invention, "neurogenesis" signifies the generation of neurons from neural stem cells, and "neural regeneration" or "neuro-regeneration" signifies the organizational and functional regeneration of the nervous system that was degenerated due to neuronal cell death through neurogenesis. In addition, the composition of the present invention can exert a treatment or prevention effect by protecting neural stem cells or neurons against amyloid-beta oligomers.

Furthermore, applications of the present invention can be widely used as materials for the examination of drug effects or for numerous studies in the development of new drugs for neurodegenerative disease.

BRIEF DESCRIPTION OF DRAWINGS

FIGS. 5a-5b show the result of Example 4-1 that shows the relative mRNA expression levels of the neuronal-specific marker Tuj1 (FIG. 5a) and the dopaminergic neuronal marker TH (FIG. 5b) in mouse embryonic neural stem cells treated with various concentrations of trametinib and AS703026.

FIGS. 6a-6d are part of the result of Example 4-2 that shows the relative mRNA expression levels of the dopaminergic neuronal marker TH (FIG. 6a), the cholinergic neuronal marker ChAT (FIG. 6b), the motor neuron marker Isl1 (FIG. 6c), and the GABAergic neuronal marker Gad1 (FIG. 6d) in mouse embryonic neural stem cells treated with various concentrations of trametinib.

FIGS. 7a-7c are part of the result of Example 4-2 that shows the relative mRNA expression levels of the neuronal marker Tuj1 (FIG. 7a), the cholinergic neuronal marker ChAT (FIG. 7b), and the dopaminergic neuronal marker TH (FIG. 7c) in mouse adult neural stem cells treated with 10 nM trametinib (Tra) and 10 μM AS703026 (AS).

FIG. 8a is the result of Example 5-1 that confirms the presence or absence of expression of the dopaminergic neuronal marker TH through RT-PCR in order to analyze the ability of mouse embryonic neural stem cells, where MEK1 or both MEK1 and MEK2 expression are inhibited, to differentiate into neurons.

FIG. 10c is the phase-contrast microscopy observations of mouse adult neural stem cells treated with PD0325901, RO5126766, BI847325, and U0126 (FIG. 10c).

FIG. 12b shows the quantitated cell number ratio of NeuN stained cells in trametinib-administered mice compared to controls that were only administered vehicles (FIG. 12b).

FIG. 13b shows the quantitated cell number ratio of NeuN stained cells in trametinib-administered mice compared to controls that were only administered vehicles (FIG. 13b).

FIG. 14b shows the quantitated cell number ratio of NeuN stained cells in trametinib-administered mice compared to controls that were only administered vehicles (FIG. 14b).

In FIG. 16a, parts marked with arrows (→) indicate cells stained with Dcx and the parts marked with arrowheads (▼) indicate cells labeled with BrdU.

FIG. 19b is the quantification of the pERK protein levels (FIG. 19b).

Figure 1:
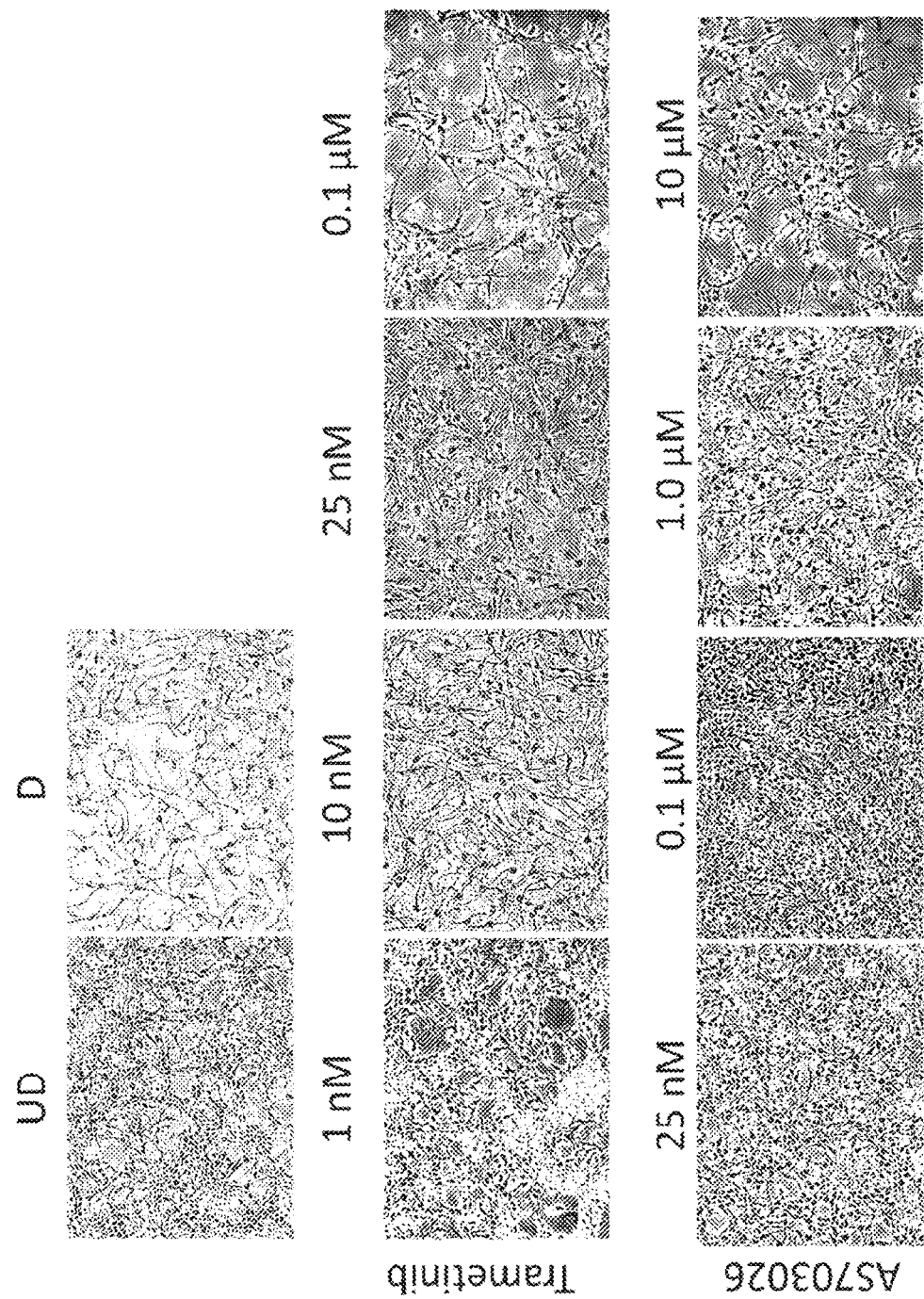
FIG. 1 is the morphology analysis of Example 1 in which the differentiation of mouse embryonic neural stem cells into neurons when treated with various concentrations of trametinib and pimasertib (AS703026) is observed by phase-contract microscopy. UD and D are undifferentiated mouse embryonic neural stem cells obtained from Example 1 Step 1A and differentiated mouse embryonic neural stem cells obtained from Step 1B, respectively, that are not treated with any test material.

The asterisk (*) marks in the graphs of the Figures indicate the following through statistical t-test results: *: $P<0.05$, : $P<0.01$, *: $P<0.005$.

BEST MODE FOR CARRYING OUT THE INVENTION

When neural stem cells were treated with the compound of [Formula 1] of the present invention, the present inventors saw an increased level of expression in the neuronal marker Tuj1, as well as increased levels of expression in all of the following: the dopaminergic neuron marker TH, the GABAergic neuron marker Gad1, the motor neuron marker Isl1, and the cholinergic neuron marker ChAT (Example 4). This signifies that the compound of [Formula1] can differentiate neural stem cells into various types of neurons such as dopaminergic neurons, GABAergic neurons, cholinergic neurons, and motor neurons. Accordingly, the compound of [Formula 1] can be used in the treatment for various neurodegenerative diseases that are caused by various neuronal loss or damage. For example, Parkinson's disease is generally associated with the loss of dopaminergic neurons, motor neuron diseases such as Lou-Gehrig's disease/ALS, progressive bulbar palsy (PBP), progressive muscular atrophy (PMA), primary lateral sclerosis (PLS), pseudobulbar palsy (PBA), and hereditary spastic paraplegia (HSP) are associated with the loss of motor neurons, and dementia such as Alzheimer's, vascular dementia, and senile dementia are usually associated with the loss of cholinergic neurons. In addition, Huntington's disease is usually associated with the loss of GABAergic medium spiny neurons in the striatum of the basal ganglia.

In particular, because the compound of [Formula 1] allows the differentiation of neural stem cells into neurons while protecting them against Aβ, the major neuropathological feature of Alzheimer's disease, it can be usefully applied as a treatment for Alzheimer's disease.

The present inventors have confirmed that the compound of [Formula 1] increased the number of neurons in the regions of the subiculum and cerebral cortex layer 5 in the Alzheimer's mouse model (5xFAD) which expresses the human Alzheimer's genes (Example 8). The 5xFAD mouse carries the gene mutations for APP (amyloid precursor protein) and presenilin (PSEN1) which are known to cause human familial Alzheimer's disease and accumulates high levels of amyloid deposition in the subiculum and cerebral cortex layer 5 with concomitant neuronal loss in these regions. The finding that the compound of [Formula 1] increased the number of neurons in the 5xFAD mouse model supports the fact that the compound of [Formula 1] induces the differentiation of neural stem cells into neurons in vivo to increase the number of neurons and/or protects neurons against amyloid-beta.

Also, the compound of [Formula 1] increased the number of neurons in various regions of the cerebral cortex in the 5xFAD mouse, especially the motor cortex and somatosensory cortex regions, when compared with controls (Example 8, FIG. 12, 13). This shows that the compound of [Formula 1] can be used for the treatment of motor neuron disease, such as ALS, caused by loss of neurons in that region.

Figure 18:
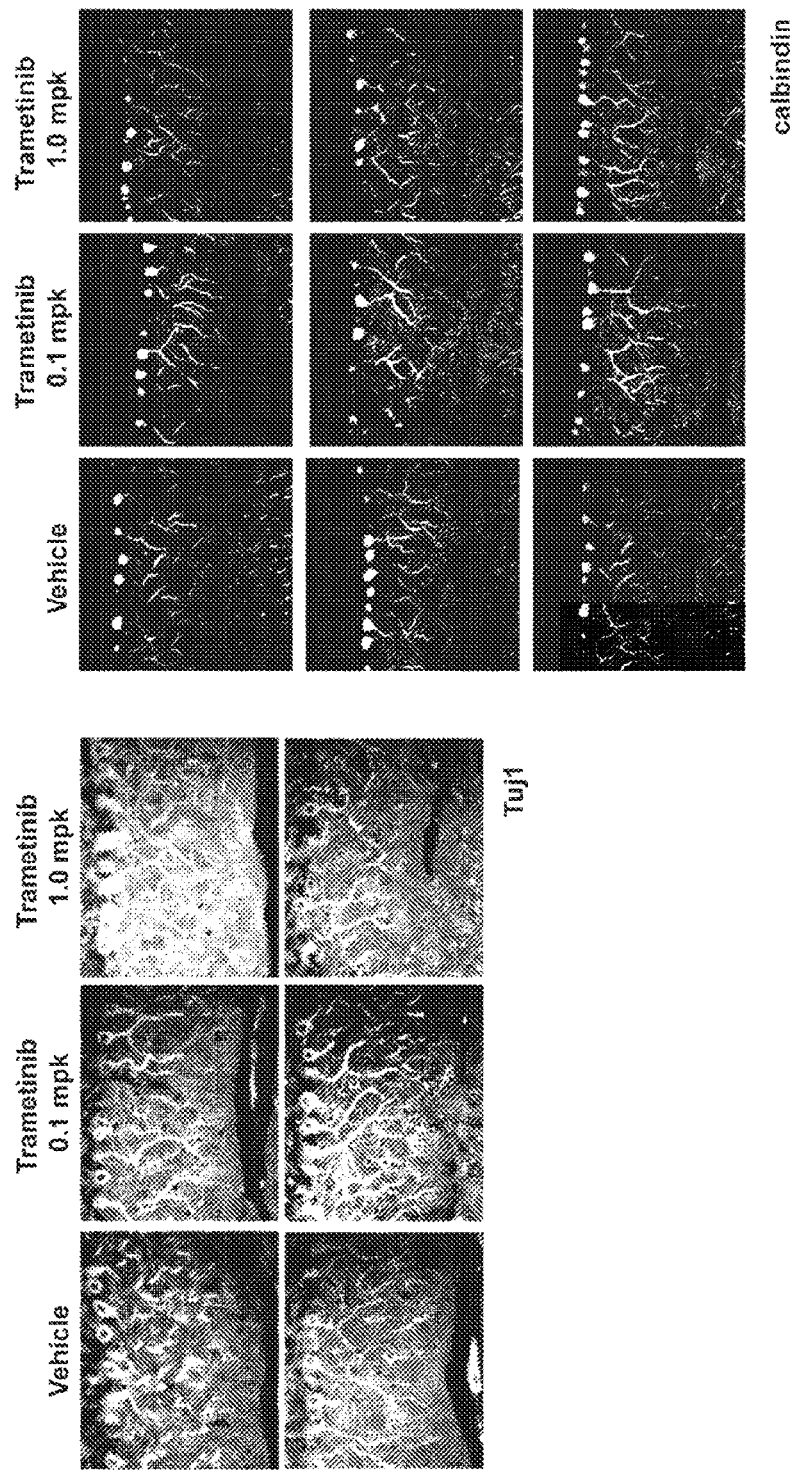
FIG. 18 is the result of Example 11 that shows Purkinje Cells through Tuj1 and calbindin staining in slices of the cerebellum of trametinib-administered 5XFAD mice. Two (Tuj1 staining) or three (calbindin staining) slide pictures of each group are shown.

Also, the compound of [Formula 1] increased axon arborization or preserved axon structure of the Purkinje Cells in the 5xFAD mouse cerebellum when compared with controls (Example 11, FIG. 18). This shows that the compound of [Formula 1] can be used for the treatment of cerebellar ataxia caused by the loss or damage of cerebellar Purkinje Cells.

The compound of [Formula 1] generates new neurons (neurogenesis), protects neurons, or does both and through this, has the effect of inducing neural regeneration or neuro-regeneration. As shown in the results of Example 9, the compound of [Formula 1] increased the expression of the neuronal marker Tuj1(marker for neurons in the process of neurogenesis) in the somatosensory cortex region of the Alzheimer model mouse (5xFAD), increased the number of type 2 or type 3 shaped cells (that appear specifically during neurogenesis) in the subgranular zone (SGZ) of the dentate gyrus (Nissl and NeuN staining results in FIG. 16), and increased the number of immature neuronal cells that express DCX and dividing cells stained by BrdU (FIG. 16). The results support that trametinib induces neurogenesis in the cerebral cortex and hippocampal dentate gyrus of the mouse.

Figure 20:
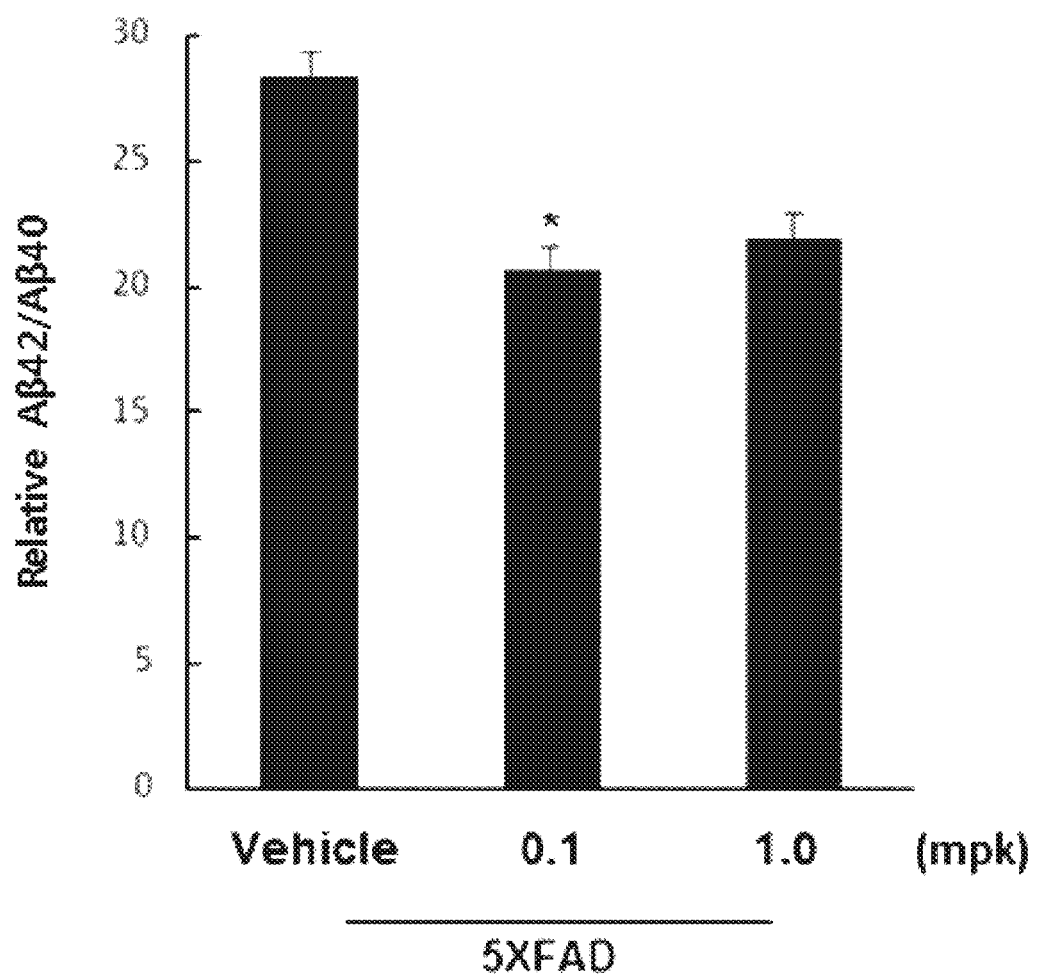
FIG. 20 is the result of Example 13 that shows the quantification of Aβ40 and Aβ42 and the ratio (Aβ42/Aβ40) through ELISA (Enzyme-linked immunosorbent assay) using the brain hemispheres of trametinib-administered 5XFAD mice.

Moreover, the compound of [Formula 1] decreased the number of dying cells as detected by TUNEL assay in the 5xFAD mouse (Example 10, FIG. 17), increased axon arborization or preserved axon structure of the cerebellar Purkinje Cells (Example 11, FIG. 18), and decreased the ratio of Aβ(1-42)/Aβ(1-40) in the 5xFAD mouse brain tissue (Example 13, FIG. 20). This shows that the compound of [Formula 1] can play a role in neuro-regeneration by protecting neurons and improving their condition or activity in an environment where neuronal damage and loss occur.

Accordingly, another aspect of the present invention relates to the pharmaceutical composition comprising the compound of [Formula 1] as an active ingredient for the prevention and treatment of neurodegenerative disease, to the method of prevention and treatment for neurodegenerative disease using the compound of [Formula 1], and to the compound of [Formula 1] for use in the prevention and treatment of neurodegenerative disease. In the present invention, other MEK1/2 inhibitors that differentiate NSC into neurons while protecting them from toxic substances such as Aβ may be used in place of the compound of [Formula 1], but it is particularly preferable to use the compound of [Formula 1].

As mentioned above, neurodegenerative disease signifies the degeneration of mental and physical function caused by the gradual loss of the structure and function of neurons. Specifically, it includes disorders selected from dementia, Alzheimer's disease, vascular dementia, senile dementia, frontotemporal dementia, Lewy body dementia, Parkinson's disease, multiple system atrophy, corticobasal degeneration, progressive supranuclear palsy, Huntington's Disease, Lou Gehrig's disease/ALS, primary lateral sclerosis, spinal muscular atrophy, progressive bulbar palsy (PBP), progressive muscular atrophy (PMA), pseudobulbar palsy, hereditary spastic paraplegia (HSP), cerebellar ataxia, Creutzfeldt-Jakob disease, multiple sclerosis, Guillain-Barre syndrome, etc.

In particular, because the compound of [Formula 1] shows a significant differentiation-inducing effect and neuro-protective effect, even at lower concentrations than the previous concentrations used for its anticancer activity, it can be safely administered at a lower dose than that used for cancer treatment. When using the compound of [Formula 1] as a cancer drug, the recommended dose is 2 mg once a day, and if a lower dose is required due to side-effects, the dose is reduced to 1.5 mg once daily and then to 1 mg once daily. In the present invention, we confirmed that the compound of [Formula 1] shows neural stem cell differentiation-inducing activity at a dose as low as 0.1 mg/kg/day in 5xFAD mouse experiments. When this dose is converted to adjust for a 60 kg person, it translates to 0.48 mg/day (Journal of Basic and Clinical Pharmacy, 7(2), 27-31, 2016).

In the present application, the term 'comprising as an active ingredient' indicates including enough of the ingredient to suppress the neurodegenerative disease associated with the present invention.

The preventive or therapeutic composition of the present invention can be produced into formulations commonly used in the art, for example, oral medication or parenteral medication such as injectables.

The pharmaceutical composition of the present invention can include suitable carriers, excipients, and diluents commonly used in pharmaceutical preparations and can be formulated in the form of oral formulations such as powder, granules, tablets, capsules, suspensions, emulsions, syrups, aerosols, etc., or topical preparations, suppositories, patches, and sterilized injection solutions.

The carriers, excipients, and diluents that can be included in the composition of the present invention are lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, croscarmellose sodium, hydroxypropylmethyl cellulose, polyvinlypyrrolidone, water, methyl hydroxybenzoate, propyl hydroxybenzoate, talc, magnesium stearate, sodium lauryl sulfate, colloidal silicon dioxide, croscarmellose sodium, mineral oil, etc.

Commonly used diluents and excipients such as fillers, extenders, binders, wetting agents, disintegrators, and surfactants are used for pharmaceutical formulations. Solid formulations for oral administration include tablets, pills, powder, granules, capsules, etc. Solid formulation is prepared by adding at least one excipient such as starch, calcium carbonate, sucrose, lactose, or gelatin to the composition of the present invention. In addition to simple excipients, lubricants such as magnesium stearate and talc are also used. Liquid formulations for oral administration include suspension, liquids for internal use, emulsion, syrups, etc., and in addition to the commonly used simple diluents such as water and liquid paraffin, they can include various excipients such as wetting agents, sweeteners, fragrances, preservatives, etc. Formulations for parenteral administration include sterilized aqueous solutions, non-aqueous solutions, suspensions, emulsions, freeze-dried formulations, suppositories, and patches. For non-aqueous solutions and suspensions, propylene glycol, polyethylene glycol, vegetable oils such as olive oil, and injectable esters such as ethyl oleate can be used. Witepsol, macrogol, Tween 61, cacao butter, lauric butter, glycerogelatin, etc., can be used for the suppository base.

The composition of the present invention can be administered either orally or parenterally and can be either a systemic or topical administration.

The recommended dose of the therapeutic composition of the present invention may vary depending on the patient's condition, the patient's weight, the severity of the disease, form of medication, route of administration, period of treatment, etc. and can be accordingly determined by those skilled in the art. For example, the composition of the present invention can be administered daily at a dose of 0.0001 to 10 g/kg, preferably 0.001 to 8 mg/kg. The dosage can be once a day or divided into several times a day. Preferably, the compound of [Formula 1] can be administered at a daily dose ranging from 0.1 mg to 10 mg, 0.1 mg to 5 mg, 0.1 mg to 2 mg, 0.1 mg to 1 mg, 0.1 mg to 0.5 mg, 0.25 mg to 2 mg, 0.25 mg to 1 mg, 0.25 mg to 0.5 mg, 0.5 mg to 2 mg, 0.5 mg to 1 mg. For example, the compound of [Formula 1] can be administered at a daily dose of 0.1 mg, 0.125 mg, 0.25 mg, 0.5 mg, 0.75 mg, 1 mg, 1.5 mg, or 2 mg.

In another aspect of the present invention, the present invention discloses a method of screening for materials that induce the differentiation of neural stem cells into neurons while at the same time protecting NSCs and neurons in neurodegenerative disease simulated environments such as Alzheimer's. The screening method utilizes neuron damage-inducing substances such as amyloid-beta, MPTP (1-methyl-4-phenyl-1,2,3,6-tetrahydropyridine), rotenone, oxidopamine, glutamate, LPS (lipopolysaccharide), and S100B (S100 calcium-binding protein B) and neural stem cells derived from the mouse and includes the steps of:

1) treating neural stem cells isolated from adult mouse with neuron damage-inducing substances such as amyloid-beta, specifically in its oligomeric form, MPTP (1-methyl-4-phenyl-1,2,3,6-tetrahydropyridine), rotenone, oxidopamine, glutamate, LPS (lipopolysaccharide), and S100B (S100 calcium-binding protein B);

2) adding a test material to the neural stem cells treated with the above neuron damage-inducing substances; and 3) examining the differentiation or death of the neural stem cells by morphology analysis.

In the screening method, it is preferable that the neural stem cells used derive from the mouse. Using neural stem cells from animals such as the mouse over human neural stem cells has the advantages of easier cell culturing methods and less controversial ethical issues. Human neural stem cell cultures require frequent culture media replacement and expensive growth factors, whereas mouse neural stem cell cultures do not. Human neural stem cell cultures require 7 days each for the process of cell expansion and differentiation, whereas mouse neural stem cell cultures require 3-4 days for expansion and only a short period of time for differentiation, allowing faster speed for screening.

Neural stem cells can be isolated from mouse adult brain and cultured for use. Mouse adult neural stem cells are isolated from week 8 to week 12 mouse, for example, from the sub-ventricular zone of week 8 mouse. It is common to isolate mouse neural stem cells from the frontal lobes of mouse embryos that are 12 to 16 days of gestation. Compared to mouse adult neural stem cells, mouse embryonic neural stem cells have a stronger stemness, which would make them more likely to withstand toxic environments. However, the present inventors observed that when mouse embryonic neural stem cells were treated with amyloid-beta, irrelevant to whether or not the test material was added, all the cells died and no neuronal differentiation could be observed (Comparative Example 1, FIG. 3). In contrast, neural stem cells isolated from mouse adult brains showed a stronger tolerance to amyloid-beta and was thus considered to be more suitable for the screening of the neural stem cell differentiation-inducing material in AD simulated environment. Therefore, we use neural stem cells of the adult mouse for the methods of the present invention.

The neural stem cells isolated from adult mouse may be inoculated into a culture medium in the undifferentiated state and cultured at 37° C. The culture medium for the neural stem cells may be any growth factor supplemented serum-free medium, but it is preferably a growth factor supplemented IPM medium when first isolating and culturing neural stem cells from adult mouse and then N2 medium when isolating and culturing single cells after the formation of neurospheres. The IPM medium is a Neurobasal medium that may include 1-4% B27 supplement, 0.5-2% Glutamax, 100 IU/ml penicillin, and 100 µg/ml streptomycin. The N2 medium is a Dulbecco's Modified Eagle's Medium/Nutrient Mixture F12 (DMEM/F12)(1:1) that may further contain one or more medium components selected from the group consisting of 90-11 µM putrescine, 20-40 nM selenite, 10-30 nM progesterone, 1.0-2.0 mg/ml d-(+)-glucose, 20-30 µg/ml insulin, 0.05-0.2 mg/ml apo-transferrin, 0.3-0.6 mM Glutamax, 50-150 IU/ml penicillin, and 50-150 µg/ml streptomycin. The N2 medium may be supplemented with growth factor selected from the group consisting of 10-30 ng/ml bFGF, 10-30 ng/ml EGF, and mixtures thereof. Growth factors play a role in maintaining the neural stem cells in the undifferentiated state. In order to accurately determine the test material's activity on inducing neural stem cell differentiation, the test material should be added to neural stem cells maintained in the undifferentiated state by growth factors that suppress differentiation.

In the present invention's screening method, commercial amyloid-beta, the one available from Gibco (Waltham, Mass.) for example, can be used. It is preferable to use amyloid-beta of human origin. The most common forms of amyloid-beta are Aβ(1-40) which consists of 40 amino acids and Aβ(1-42) which consists of 42 amino acids. Of the two, Aβ(1-42) has a stronger tendency to form aggregates, especially the highly toxic trimers and tetramers, and is thus considered to be more highly correlated with the pathological state of Alzheimer's disease (Dahlgren et al. (2002) Oligomeric and Fibrillar Species of Amyloid-β Peptides Differentially Affect Neuronal Viability, J. Biol. Chem. 277(35):32046-32053; K. Murakami (2014) Conformation-Specific Antibodies to Target Amyloid-β Oligomers and Their Application to Immunotherapy for Alzheimer's Disease, Biosci. Biotechnol. Biochem. 78(8): 1293-1305). Therefore, it is preferable to use Aβ(1-42), particularly the oligomeric form of Aβ(1-42), in the present invention's screening method.

In the present invention's screening method, the oligomeric form of amyloid-beta should be oligomers of less than 24, preferably 12 or fewer amyloid-beta monomers, more preferably a mixture mainly consisting of amyloid-beta tetramers and trimers with almost no amyloid-beta protofibrils or fibrils. The oligomeric form of Aβ(1-42) in the present invention can be prepared by the method disclosed in the reference [Dahlgren et al. (2002) Oligomeric and Fibrillar Species of Amyloid-β Peptides Differentially Affect Neuronal Viability, J. Biol. Chem. 277(35): 32046-32053]. Specifically, Aβ(1-42) is dissolved in hexafluoroisopropanol (HFIP), dried in a vacuum, and the dried peptide is resuspended in DMSO at a concentration of 5 mM. DMEM/F12 (without phenol red) is added and the peptide concentration is adjusted to 100 µM, after which it is cultured at 4° C. for 24 hours.

In the present invention's screening method, MPTP is a prodrug for the neurotoxin MPP+ (1-methyl-4-phenylpyridinium). MPP+ causes permanent symptoms of Parkinson's disease (PD) through the destruction of dopaminergic neurons in the substantia nigra of the brain.

Rotenone, a substance that causes the degeneration of dopaminergic neurons in the substantia nigra by inhibiting the activity of the mitochondrial complex 1 in the cell, is known to produce the pathological features of PD.

Oxidopamine, also called 6-hydroxydopamine (6-OHDA) or 2,4,5-trihydroxyphenethylamine, is a neurotoxic compound used by investigators to selectively destroy dopaminergic and noradrenergic neurons in the brain. It is thought that oxidopamine enters the neuron through the dopaminergic and noradrenergic reuptake transporters. In order to selectively damage dopaminergic neurons, it is also used with a selective noradrenergic reuptake inhibitor such as desipramine.

Glutamate acts as the main excitatory neurotransmitter in the central nervous system (CNS), but is known to damage neurons and cause cell death when present in high concentrations. The excitotoxicity of glutamate is not only associated with acute CNS damage such as ischemia or traumatic brain damage, but also with chronic neurodegenerative disease such as ALS, multiple sclerosis, PD, etc.

LPS (lipopolysaccharide) is a component of the cell surface of Gram negative bacteria and the one isolated from Salmonella typhimurium (Sigma, St. Louis, Mo.) may be used, for example. LPS elicits a strong immune response in animals and causes an inflammatory response by activating microglia in the nervous system. The secretion of inflammatory substances due to overactivated microglia can disturb the homeostasis of the immune system and cause CNS autoimmune disease related neurodegenerative disease such as multiple sclerosis, AD, and PD.

S100B is a calcium-binding protein expressed and secreted by astrocytes. It has neurotrophic activity for the development and maintenance of neurons and affects normal cognitive functions of the brain. However, abnormally high levels of S100B will activate glia and cause neuroinflammatory responses that are harmful to neurons.

In the present invention's screening method, neural stem cells are treated with neuron damage-inducing substances such as amyloid-beta before the addition of the test material. In previously published experiments, neural stem cells were first treated with the test materials a certain time before amyloid-beta was added to observe the test materials' neural protection effect (J. Korean Neurol. Assoc. 21(2):174-182, 2003). This method does not reflect the actual treatment situation where Alzheimer's patients are administered drugs after amyloid-beta is already present in their brains. Neural stem cells should first be treated with amyloid-beta before the addition of the test material as performed in the present invention in order to more closely simulate the brain environment of Alzheimer's patients at the time point when treatment is commenced.

The test material is added to the neural stem cells after they are treated with amyloid-beta and further cultured with the daily addition of growth factors. After treating the neural stem cells with the test material, it can be determined whether or not the test material has neural stem cell differentiation-inducing activity by a morphology analysis at the earliest, 12 hours, and latest, 48-72 hours after treatment.

Morphology analysis uses the phase-contrast microscope to observe and determine the morphology of the cell. As can be seen in the top part of FIG. 2 labeled UD (undifferentiated) and D (differentiated), differentiated (D) neural stem cells can be clearly distinguished from undifferentiated (UD) ones. In undifferentiated cells, cell bodies are wide, the shape of neurites such as axons and dendrites are difficult to discern, and the total cell number is high since the cells are continually dividing. In differentiated cells, cell bodies are small and round, while neurites are thin and extended.

The neural stem cells used in the present invention's screening method are relatively fragile cells compared to normal or cancer cell lines and respond sensitively to the toxicity of the test material. If the test material shows cell toxicity, dead cells can be seen in the microscope, making it possible to determine cell toxicity at the same time as determining differentiation-inducing activity.

According to the present invention's screening method, materials that have neural stem cell differentiation-inducing activities can be screened in an environment that simulates the brain environment of an Alzheimer's patient, especially in which oligomeric forms of amyloid-beta, the form which is known to be strongly correlated with neuronal loss, are present. This makes the present invention's screening method suitable for the screening of candidate materials that can be used for the fundamental treatment of Alzheimer's disease. In addition, the screening method is convenient in that it allows the determination of whether or not cells have differentiated by examining cell morphology, without the need for additional experimental analyses. Also, when neural stem cells are allowed to naturally differentiate in media without growth factors, it takes at least 48 hours, after which the change in cell morphology can be observed. In the case of cells treated with materials that have highly efficient differentiation-inducing activity, their effect can be observed as early as 12 hours after treatment and at latest, 48-72 hours after treatment despite the presence of growth factors in the cell culture media for suppression of differentiation. In this way, the screening method is fast and efficient, since the toxicity of the test material can also be determined at the same time the differentiation-inducing effect is.

In addition, the present invention relates to the kit that can be used to perform the aforementioned screening method. This kit may include neural stem cells derived from adult mouse, neuron damage-inducing substances such as amyloid-beta, MPTP, rotenone, oxidopamine, glutamate, LPS, or S100B, growth factors, culture media, supplements for cell cultures, and cell culture plates (coated or with separate coating solutions).

The present invention will be explained in more detail with reference to the following examples. However, these examples are not to be construed as limiting or restricting the scope and disclosure of the invention. It is to be understood that based on the teachings of the present invention including the following examples, those skilled in the art can readily practice other embodiments of the present invention whose experimental results are not explicitly presented. Such modifications and variations are intended to come within the scope of the appended claims.

EXAMPLES

Example 1

The NSC Differentiation-Inducing Ability of the Compound of [Formula 1] in Mouse Embryonic Neural Stem Cells Step 1: Culturing mouse embryonic neural stem cells
Step 1A: Culturing mouse embryonic neural stem cells in the undifferentiated state Neural stem cells were isolated from the brain of a day 14.5 mouse embryo, treated with 10 ng/ml human basic fibroblast growth factor (bFGF) (Peprotech, Princeton, NG, cat#.100-18B) and 20 ng/ml human epidermal growth factor (EGF) (Peprotech, cat#. AF-100-15) in a N2 culture medium, and cultured in suspension in a 25 cm2 flask (Nunc, Pittsburgh, Pa.) for 4 days. Formation of neurospheres was observed after 2 days.

In order to isolate single cells, 6-well plates were prepared the day before by treating the wells with 15 μg/ml poly-L-ornithine (Sigma, St. Louis, Mo., cat#.P2533) solution and incubating overnight at 37° C. for coating. The day of the single cell isolation, poly-L-ornithine solution was removed, the plates were washed with PBS three times, and 10 μg/ml fibronectin (Gibco, Waltham, Mass., cat#. 33016015) solution was added and incubated at 37° C. for 2 hours for coating. When plate preparation was complete, neurospheres were treated with TryPLE (Gibco cat#. 12604013), separated into single cells, and counted and prepared to comprise 4~5×105 cells per 200~300 μl culture solution (N2 culture medium with 10 ng/ml bFGF and 20 ng/ml EGF). Right before seeding, the coating solution was suctioned out, and the single cells were uniformly seeded into the culture plate before the plate dried up. Cells were allowed to attach to the plates for about 1 minute and after checking that cells were sufficiently attached, an additional 1.5 ml of culture medium (N2 culture medium with 10 ng/ml bFGF and 20 ng/ml EGF) was added to the cells and cultured in a 37° C. incubator.

The composition of the N2 culture medium is as follows:
Dulbecco's modified Eagle's medium (DMEM)/F12 (1:1) (Gibco, cat#. 11320033), 100 μM putrescine (Sigma, cat#. 51799), 30 nM selenite (Sigma cat#. S5261), 20 nM progesterone (Sigma cat#. P0130), 1.55 mg/ml d-(+)-glucose (Sigma, cat#. G8270), 25 μg/ml insulin (Gibco, cat#. 12585014), 0.1 mg/ml apo-transferrin (Sigma cat#. T1147), 0.5 mM Glutamax (Gibco, cat#. A1286001), 100 IU/ml penicillin (Gibco, cat#. 15140122), 100 μg/ml streptomycin (Gibco, cat#. 15140122).

Step 1B: Culturing Neural Stem Cells without Inhibiting Differentiation

Mouse embryonic neural stem cells were cultured in accordance with the procedure in Step 1A except for the addition of bFGF and EGF when neural stem cells were separated into single cells and seeded.

Step 2: Addition of Test Material

Various concentrations of the compound of [Formula 1] (hereinafter also referred to as trametinib) (Medchem express, Monmouth Junction, N.J., cat#. HY-10999A) and AS703026 (pimasertib) (Selleckchem, Houston, Tex., cat#. S1475) were added daily to mouse embryonic neural stem cells cultured as described in Step 1A and cultured for 4 days.

Step 3: Morphology Analysis

Cell morphology was observed by phase-contrast microscopy after four days of culture, and the results are shown in FIG. 1.

In FIG. 1., UD (undifferentiated) is undifferentiated mouse embryonic NSC obtained in Step 1A where the cells are not treated with any test material. D (differentiated) is differentiated mouse embryonic NSC obtained in Step 1B where the cells are not treated with any test material. The undifferentiated NSC of the UD group have wide cell bodies, the neurite shape is hard to distinguish, and the overall cell numbers are higher compared with the D group due to continuous cell division. The differentiated cells of the D group have smaller round cell bodies with elongated thin neurites, making them easily distinguishable from the UD group cells.

As shown in FIG. 1, the compound of [Formula 1] (trametinib) readily induced the differentiation of NSC into neurons at low concentrations of 10 nM, 25 nM, and 100 nM (0.1 μM). The AS703026-treated group required 1.0 μM, a concentration 100 times higher than that of trametinib, for neuronal differentiation to initiate.

Taken together, these results indicate that the compound of [Formula 1] (trametinib) induces the differentiation of NSC into neurons and this effect is seen even at very low concentrations (at 10 nM and greater). This suggests that the compound of [Formula 1] can be used for the composition and method for differentiation to induce the differentiation of NSC to neurons and for the treatment of neurodegenerative disease.

Example 2

The NSC Differentiation-Inducing Ability of the Compound of [Formula 1] in Mouse Adult NSC (Method of Screening for Substances that can Induce the Differentiation of NSC into Neurons while Protecting them at the Same Time)

Step 1: Culturing Mouse Adult NSC

Step 1A: Culturing Mouse Adult NSC in the Undifferentiated State

NSC were isolated from the subventricular zone of week 8 mouse brain, treated with 20 ng/ml human basic fibroblast growth factor (bFGF) and 20 ng/ml human epidermal growth factor (EGF) in an IPM medium, and cultured as a suspension in 24-well plates for 7 days. The formation of neurospheres was observed after 4 days.

Two days before the isolation of single cells, 6-well plates were prepared by treating the wells with 10 μg/ml poly-L-ornithine solution and incubating overnight at room temperature for coating. The next day, poly-L-ornithine solution was removed and the plates were washed 3 times with sterilized triple distilled water. Next, 0.5 mg/ml laminin (Roche, Upper Bavaria, Germany, cat#. 11243217001) solution was added and incubated overnight at 37° C. for coating. When plate preparation was complete, neurospheres were treated with 0.025% Trypsin-EDTA, separated into single cells, and counted and prepared to comprise 4~5×105 cells per 200~300 μl culture solution. The culture solution used is N2 culture medium (supplemented with 20 ng/ml bFGF and 20 ng/ml EGF). Right before seeding, the coating solution was suctioned out, and the single cells were uniformly seeded into the culture plate before the plate dried up. Cells were allowed to attach to the plates for about one minute, and after checking that cells were sufficiently attached, an additional 1.5 ml of culture medium (N2 culture medium with 20 ng/ml bFGF and 20 ng/ml EGF) was added to the cells and cultured in a 37° C. incubator for 24 hours.

The compositions of the 1PM and N2 culture medium are as follows:

IPM medium: Neurobasal medium (Gibco, cat#. 21103049), B27 supplement (Gibco, cat#. A3582801), Glutamax, 100 IU/ml penicillin, 100 μg/ml streptomycin.

N2 medium: Dulbecco's modified Eagle's medium (DMEM)/F12 (1:1), 100 μM putrescine, 30 nM selenite, 20 nM progesterone, 1.55 mg/ml d-(+)-glucose, 25 μg/ml insulin, 0.1 mg/ml apo-transferrin, 0.5 mM Glutamax, 100 IU/ml penicillin, 100 μg/ml streptomycin.

Step 1B: Culturing Neural Stem Cells without Inhibiting Differentiation

Mouse adult neural stem cells were cultured in accordance with the procedure in Step 1A except for the addition of bFGF and EGF when neural stem cells were separated into single cells and seeded.

Step 2: Amyloid-Beta Treatment

After changing the medium of the cultured NSC in Step 1, each well was treated with 10 μM amyloid-beta (Aβ) (Gibco, cat#. 03112). Wells not treated with amyloid-beta were left to use as negative controls.

Gibco's (Waltham, Mass.) human Aβ (1-42) was purchased to use for the amyloid-beta (Aβ), and the following process was followed to create oligomers. First, amyloid-beta was dissolved in 100% HFIP (1,1,1,3,3,3-hexafluoro-2-propanol) (Sigma, cat#.105228) to obtain a concentration of 1 mg/ml and vortexed at room temperature for 1 hour. Then, it was dried for 10 minutes in a speed Vac, after which DMSO (Sigma, cat#.D2650) was added to bring the concentration to 5 mM and then lightly vortexed at room temperature for 10 minutes. DMEM/F12 (without phenol red) (Gibco, cat#. 21041025) was added for a final concentration of 100 μM. The solution was incubated at 4° C. for 24 hours and then added into the cultured cells.

Step 3: Addition of Test Material

Immediately following treatment with amyloid-beta, 10 nM, 100 nM trametinib, 5 μM, 10 μM memantine (Sigma, cat#. M9292), and 10 μM AS703026 (pimasertib) were added to the cell cultures. The NCSs were cultured with the daily addition of EGF, bFGF, amyloid-beta, and test materials for 4 days.

Step 4: Morphology Analysis

Figure 2:
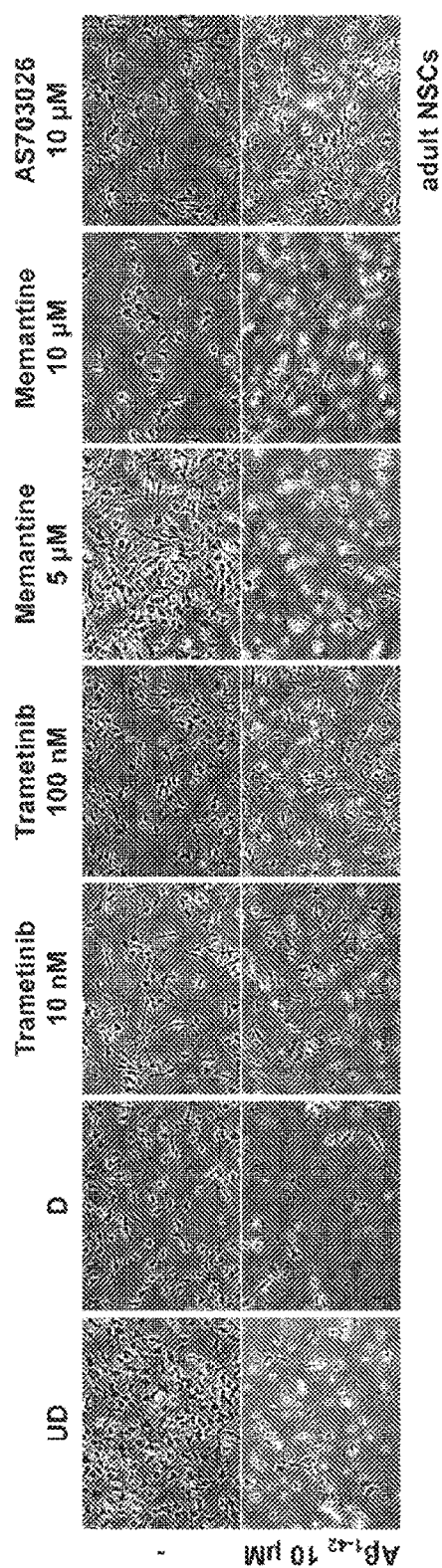
FIG. 2 is the morphology analysis of Example 2, where the bottom row shows the result of mouse adult neural stem cells treated with 10 µM oligomeric amyloid-beta (Aβ1-42) and the top row shows neural stem cells not treated with amyloid-beta. UD and D are undifferentiated mouse adult neural stem cells obtained from Example 2 Step 1A and differentiated mouse adult neural stem cells obtained from Step 1B, respectively, that are not treated with any test material. Trametinib (10 nM), trametinib (100 nM), memantine (5 μM), memantine (10 μM), and AS703026 (10 μM) are the results obtained when the undifferentiated mouse adult neural stem cells obtained from Example 2 Step 1A were treated with the respective test materials at the respective concentrations.

Cell morphology was observed by phase-contrast microscopy after four days of culture, and the results are shown in FIG. 2.

In FIG. 2., the top row is mouse adult NSC not treated with amyloid-beta and the bottom row is NSC treated with 10 μM amyloid-beta. UD (undifferentiated) is undifferentiated mouse adult NSC obtained in Step 1A where the cells are not treated with any test material. D (differentiated) is differentiated mouse adult NSC obtained in Step 1B where the cells are not treated with any test material. Of the top Aβ non-treated group, the undifferentiated NSC of the UD group have wide cell bodies, the neurite shape is hard to distinguish, and the overall cell numbers are higher compared with the D group due to continuous cell division. The differentiated cells of the D group have smaller round cell bodies with elongated thin neurites, making them easily distinguishable from the UD group cells.

The trametinib-treated group readily induced the differentiation of NSC into neurons at low concentrations of 10 nM and 100 nM, regardless of whether or not amyloid-beta was treated. The AS703026-treated group required a much higher concentration than that of trametinib, 10 μM, for neuronal differentiation, regardless of whether or not amyloid-beta was treated. Both materials did not elicit cell toxicity at these concentrations, confirming that they are suitable candidates for Alzheimer's disease (AD).

Moreover, in the group treated with memantine, a drug currently used for the relief of AD symptoms, the differentiation of NSC into neurons was not observed, but rather the opposite, the death of neural stem cells, was observed. Memantine is an NMDA receptor antagonist involved in glutamate signal transduction and works to help normalize neuronal signal transduction in AD patients. This kind of mechanism does not provide a fundamental treatment for AD through the recover of damaged neurons. The finding that memantine does not induce differentiation of NSC but rather causes cell death confirms that it cannot be used as a fundamental treatment for dementia.

Comparative Example 1

Effect of Amyloid-Beta Treatment on Mouse Embryonic Neural Stem Cells

Step 1: Culturing Mouse Embryonic NSC

Cells were cultured as described in Example 1, Step 1A and 1B.

Step 2: Treatment with Amyloid-Beta

Mouse embryonic NSCs cultured as described in the above Step 1 were treated with amyloid-beta using the same method as Example 2, Step 2.

Step 3: Addition of Test Material

Immediately following treatment with amyloid-beta, 100 nM trametinib, 10 μM memantine, and 10 μM AS703026 (pimasertib) were added. The NCS were cultured with the daily addition of EGF, bFGF, amyloid-beta, and test materials for 4 days.

Step 4: Morphology Analysis

Figure 3:
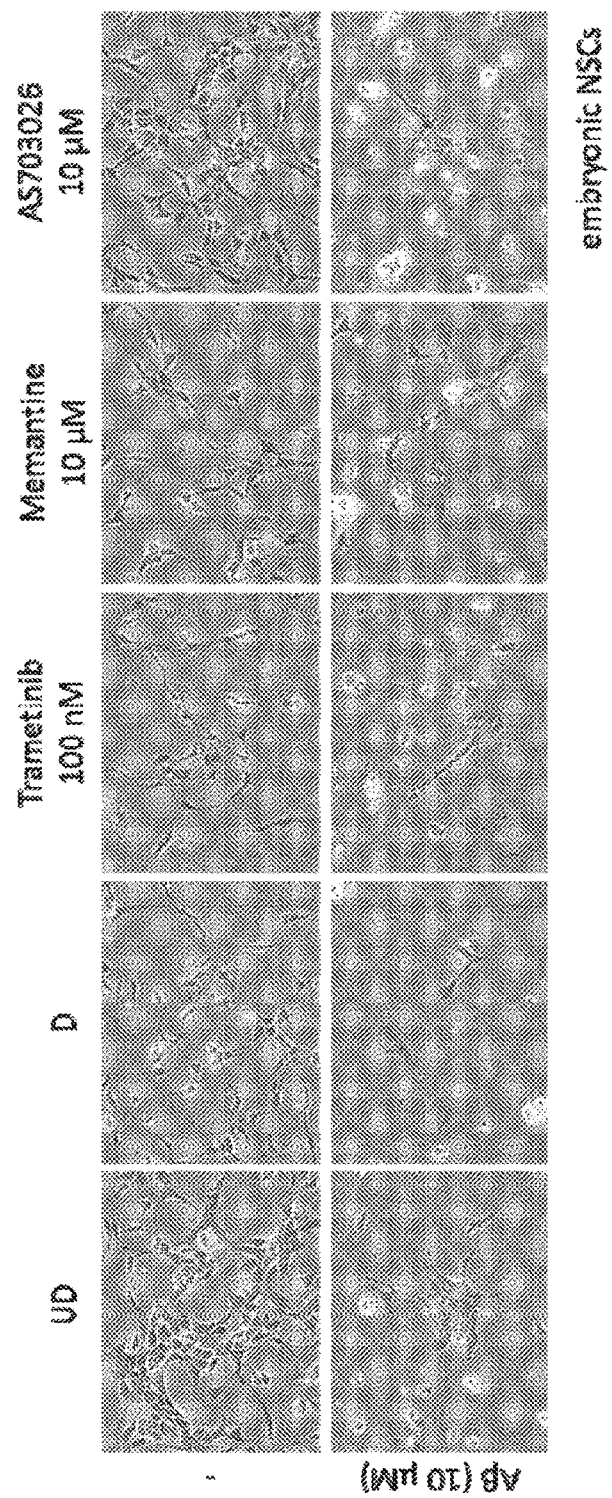
FIG. 3 is the comparison of cell morphology analysis of mouse embryonic 14.5 day neural stem cells that are treated (bottom row) or not treated (top row) with 10 μM oligomeric amyloid-beta according to Comparative Example 1. UD (undifferentiated) and D (differentiated) are undifferentiated and differentiated mouse embryonic neural stem cells obtained from Comparative Example 1 Step 1, respectively, that are not treated with any test material. Trametinib (100 nM), memantine (10 μM), and AS703026 (10 μM) are the results obtained when undifferentiated mouse embryonic neural stem cells obtained from Comparative Example 1 Step 1 were treated with the respective test materials at the respective concentrations.

Cell morphology was observed by phase-contrast microscopy after four days of culture, and the results are shown in FIG. 3.

In FIG. 3., the top row is mouse embryonic NSC not treated with amyloid-beta and the bottom row is NSC treated with amyloid-beta. UD (undifferentiated) is undifferentiated mouse embryonic NSC (not treated with any test material) and D (differentiated) is differentiated mouse embryonic NSC (not treated with any test material). In the Aβ-treated group, all the cells died, regardless of whether or not the test materials were added, and hence, the effect of the test materials could not be determined.

Example 3

Immunocytochemistry Analysis

In order to reconfirm the differentiation of NSC into neurons in Example 1, immunocytochemical staining of Tuj1 and DAPI (4',6-diamidino-2-phenylindole) markers was performed. Tuj1 (Neuron specific class III beta-tubulin) is a neuron specific marker protein, which was conjugated to rhodamine to show fluorescent red, while DAPI binds to the cell DNA and stains the cell nuclei fluorescent blue.

Figure 4:
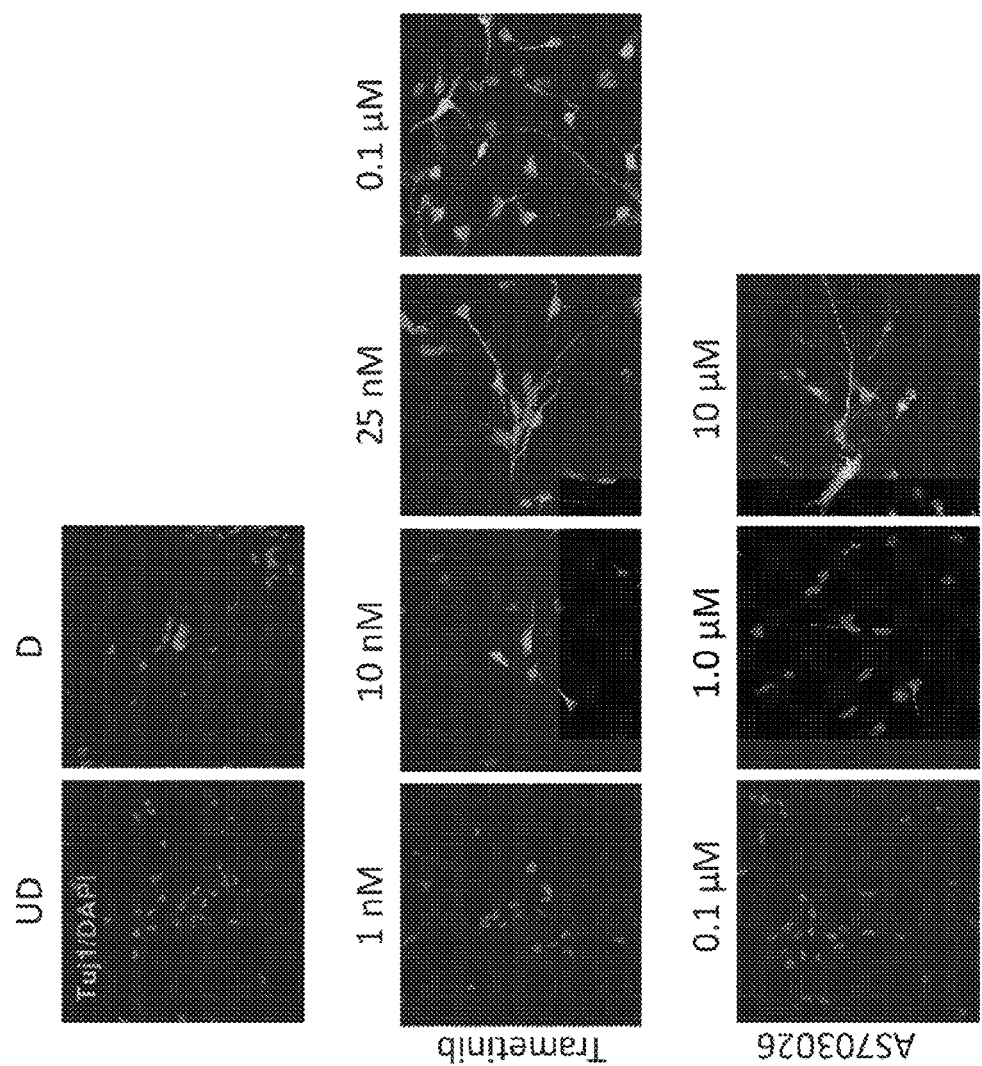
FIG. 4 is the fluorescent microscopy images of Example 3. In the first row, UD and D are undifferentiated and differentiated embryonic neural stem cells, respectively, not treated with any test material. The second and third rows are images of cells treated with the respective concentrations of trametinib and AS703026. The blue dots represent cell nuclei stained with DAPI, and the cells with red elongated thin branches represent neurons stained with rhodamine-coupled Tuj1.

Embryonic NSCs cultured as described in Example 1 were seeded into 24-well plates with coverslips and treated with trametinib and AS703026 in the respective concentrations for 4 consecutive days. The medium was removed and the cells were washed with PBS. After fixing with 10% formaldehyde (Sigma cat#. HT501128) at room temperature for 10 minutes, they were washed again with PBS. They were permeabilized with 0.2% Triton X-100 (Sigma, cat#. 93443) at room temperature for 15 minutes, washed with PBS, and incubated with 10% BSA (Sigma, cat#. A2153)+ 1% normal goat serum (Vector lab, Burlingame, Calif., cat#. S1000) at room temperature for 1 hour. Anti-Tuj1 antibody (Cell signaling, Danvers, Mass., cat#. 4466) was diluted in 1% BSA+1% normal goat serum at a ratio of 1:200 and added to the cells and incubated at 4° C. overnight. The solution was removed, washed with PBS, and incubated at room temperature for 1 hour with the secondary antibody (rhodamine-conjugated antibody) diluted in 1% BSA+1% normal goat serum at a ratio of 1:200. Then, the cells were washed with PBS, incubated with 5 μg/ml DAPI (Sigma, cat#. D9542) for 5 minutes, washed with PBS again, and mounted on a slide glass for analysis with a fluorescent microscope. The results are shown in FIG. 4. As seen in FIG. 4, the group treated with 1.0 μM AS703026 showed images of red thin elongated neurites, indicating that neuron differentiation occurs at this concentration, albeit only to a marginal extent. At concentrations lower than this (0.1 μM), no differentiation was observed.

In contrast, the group treated with trametinib, even at a very low concentration of 10 nM, showed increasingly active differentiation activity. As for the morphology of the cells, an increasing number of neurons showing elongated neurites are visible in 10 nM trametinib-treated cells.

Example 4

Analysis of the Relative Levels of mRNA Expression

Example 4-1

Analysis of Tuj1 and TH mRNA Expression Induced by the Compound of [Formula 1] in Mouse Embryonic NSC In order to determine what type of cells the NSCs differentiated into in Example 1, mRNA expression of the neuron specific marker Tuj1 and the dopaminergic neuron marker TH (tyrosine hydroxylase) was analyzed through quantitative RT-PCR (qRT-PCR).

Step 1: RNA Isolation

After completing the morphology analysis in Example 1, the medium of each treated group of cells was removed and TRIzol® (Invitrogen, Waltham, Mass.) was added to the plate and incubated for 5 minutes at room temperature to facilitate cell lysis. The cell lysates, together with TRIzol, were transferred to a tube, mixed thoroughly with chloroform (Sigma, cat#. 366919), centrifuged, and the supernatant transferred to a new tube. Isopropanol (Ducsan, GyunggiDo, Korea, cat#. 67-63-0) was added and mixed for RNA isolation, then centrifuged again to remove the supernatant and obtain the pellet. The RNA pellet was resuspended in 75% ethanol (Ducsan, cat#. 64-17-15), centrifuged, and the supernatant removed. The pellet was then resuspended in sterilized triple distilled water to obtain the mRNA, incubated for 10 minutes at 55° C., and stored at −80° C.

Step 2. Reverse Transcription

After measuring the RNA concentration, each group of RNA was adjusted to 2 μg and the experiment was performed using a reverse transcription kit (Invitrogen, cat#. 28025013). Sterilized triple distilled water, 1 pM oligo dT, and 1 mM dNTP were added to the RNA and incubated for 5 minutes at 65° C. This was followed by the addition of 5X First-strand buffer, 10 mM DTT, and M-MLV reverse transcriptase and incubated at 42° C. for 1 hour, then at 72° C. for 15 minutes, and at 4° C. for 30 minutes. The synthesized cDNA was stored at −20° C.

Step 3: qRT-PCR

PCR was performed by mixing 1 μl cDNA (synthesized above), 1 pM primer, triple distilled water, and Rotor-Gene SYBR® Green (Qiagen, Venlo, Netherlands, cat#. 204074) and using the Rotor-Gene Q (Qiagen). The primers (Bioneer, Daej eon, Korea) used are shown in Table 2.

TABLE 2

| Gene | Forward Primer | Reverse Primer |
|---|---|---|
| GAPDH | 5'-CGTGCCGCCTGGAGAAACC-3' (SEQ ID NO: 1) | 5'-TGGAAGAGTGGGAGTTGCTGTTG-3' (SEQ ID NO: 4) |
| Tuj1 | 5'-GGTCTGGCGCCTTTGGA-3' (SEQ ID NO: 2) | 5'-CACCACTCTGACCAAAGATAAAGTTG-3' (SEQ ID NO: 5) |
| TH | 5'-AGGTATACGCCACGCTGAAG-3' (SEQ ID NO: 3) | 5'-CTCGGGTGAGTGCATAGGTG-3' (SEQ ID NO: 6) |

The results are shown in FIG. 5. FIG. 5a, 5b are the average values of the relative mRNA expression levels for each group after 3 rounds of experiments. The term relative mRNA expression level signifies that in order to normalize each group's total RNA level, the mRNA expression level of each differentiation marker is divided by the expression level of GAPDH whose expression level is fairly constant across cells, and then the values of each test material are compared with those of the controls (undifferentiated NSC) in each group.

As shown in FIG. 5, the trametinib-treated group showed high levels of expression of the neuron specific marker Tuj1 and the dopaminergic neuron marker TH at concentrations of 10 nM, 25 nM, and 100 nM. This result indicates that trametinib efficiently induces the differentiation of NSC into neurons, especially into dopaminergic neurons. In addition, trametinib exerted its differentiation-inducing effect at a very low concentration of 1 nM. This suggests that the composition according to the present invention can be used for the treatment of neurodegenerative disease.

10 μM (10000 nM) AS703026 yielded results comparable to those of 25 nM trametinib, indicating that trametinib induces differentiation of NSC into neurons at 400 times (or more) lower concentration than that of AS703026.

Example 4-2

Analysis of TH, ChAT, Isl1, and Gad1 mRNA Expression Induced by the Compound of [Formula 1] in Mouse Embryonic and Adult NSC In order to determine if the compound of [Formula 1] induces the differentiation of NSC into cell types other than dopaminergic neurons, mRNA expression of the cholinergic neuron marker ChAT (choline acetyltransferase), the motor neuron marker Isl1 (Islet1), and the GABAergic neuron marker Gad1 (glutamate decarboxylase 1) was determined through qRT-PCR.

Neural stem cells were cultured as described in Example 1 and after the addition of 1 nM, 10 nM, 25 nM, and 100 nM trametinib for 2 days, RNA was isolated and examined for the differentiation markers. mRNA expression was determined by the same method as in Example 4-1, and the primers used are shown in Table 3.

The results are shown in FIG. 6.

TABLE 3

| Gene | Forward Primer | Reverse Primer |
|---|---|---|
| GAPDH | 5'-CGTGCCGCCTGGAGAAAC-3' (SEQ ID NO: 1) | 5'-TGGAAGAGTGGGAGTTGCTGTTG-3' (SEQ ID NO: 4) |
| Tuj1 | 5'-GGTCTGGCGCCTTTGGA-3' (SEQ ID NO: 2) | 5'-CACCACTCTGACCAAAGATAAAGTTG-3' (SEQ ID NO: 5) |
| TH | 5'-AGGTATACGCCACGCTGAAG-3' (SEQ ID NO: 3) | 5'-CTCGGGTGAGTGCATAGGTG-3' (SEQ ID NO: 6) |
| ChAT | 5'-CCTGCCAGTCAACTCTAGCC-3' (SEQ ID NO: 7) | 5'-TACAGAGAGGCTGCCCTGAG-3' (SEQ ID NO: 10) |
| Gad1 | 5'-TCATGTTATGGAAATCTTGCTTCAG-3' (SEQ ID NO: 8) | 5'-CGAGTCACAGAGATTGGTCATATACTACT-3' (SEQ ID NO: 11) |
| Isl1 | 5'-CGGAGAGACATGATGGTGGT-3' (SEQ ID NO: 9) | 5'-GGCTGATCTATGTCGCTTTGC-3' (SEQ ID NO: 12) |

As shown in FIG. 6, the expression of all the tested neuron markers, dopaminergic neuron marker TH, cholinergic neuron marker ChAT, motor neuron marker Isl1, and GABAergic neuron marker Gad1, increased with the increase in concentration of the trametinib added. This suggests that trametinib can be used in the treatment of neurodegenerative disease that is caused by various types of neuronal damage.

In order to determine if the same effect takes place in mouse adult NSC, 10 nM trametinib and 10 μM AS703026 were each added for 2 days to the mouse adult NSC cultured as described in Example 2, Step 1A, and the mRNA expression levels of the neuronal marker Tuj1, dopaminergic neuron marker TH, and cholinergic neuron marker ChAT were analyzed by qRT-PCR.

Figure 7A:
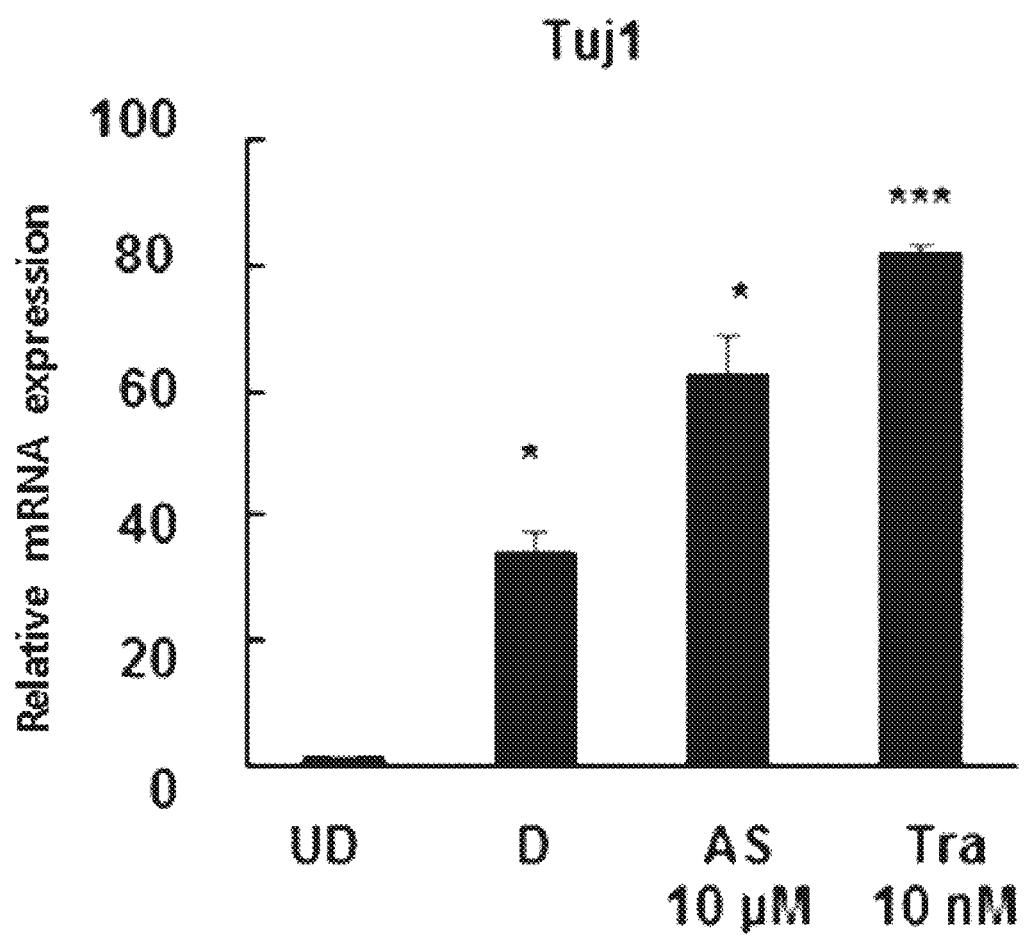
Figure 7B:
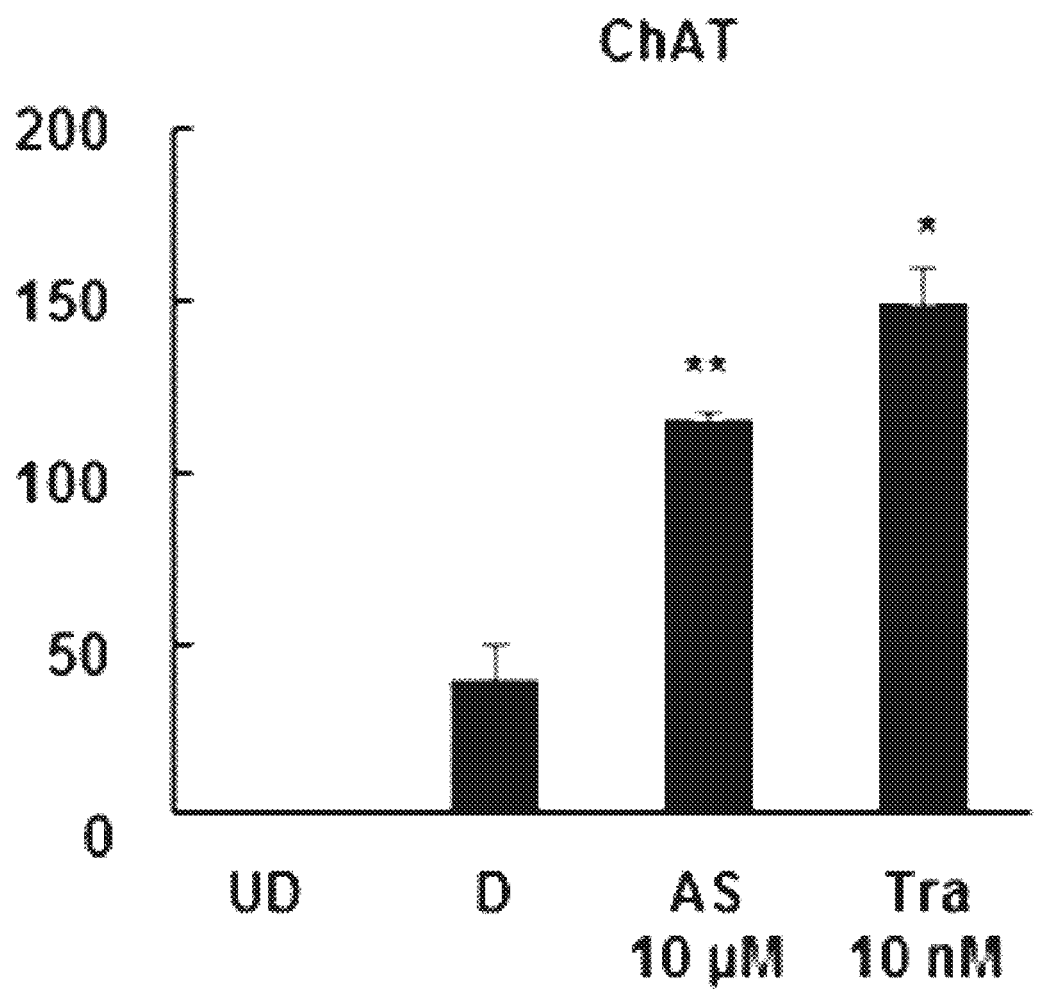

This result is shown in FIG. 7. Trametinib increased the expression of Tuj1, TH, and ChAT in adult NSC as it did in embryonic NSC. It is noteworthy that trametinib exhibited a stronger NSC to neuron differentiation-inducing effect at 1000 times lower concentration than AS703026.

Example 5

Examination of the NSC Differentiation-Inducing Ability Through the Control of MEK1 and MEK2 Expression in Neural Stem Cells Example 5-1

Inhibition of MEK1, MEK2 Expression in Mouse Embryonic Neural Stem Cells

The NSC to neuron differentiation-inducing ability in relation to the expression levels of MEK1 and MEK2 was examined. The following method was used to produce cells where MEK1 and MEK2 expression is controlled.

First, in order to produce NSCs where MEK1 and MEK2 expression is inhibited, the respective shRNAs that inhibit the expression of MEK1 and MEK2 were used. Specifically, mouse embryonic NSCs cultured as described in Example 1, Step 1A were seeded into plates and cultured for 24 hours. Then 1 μg/ml shRNA-MEK1 (CCGGGCCATCCAACAT-TCTAGTGAACTCGAGTTCACTAGAATGTTGGATG GCTTTTT (SEQ ID NO: 13)) or shRNA-MEK2 (CCGGCCTCCGAGAGAAGCACCAGATCTCGAGATC-TGGTGCTTCTCTCGGA GGTTTTTG (SEQ ID NO: 14)) were transfected into the cells using lipofectamine (Invitrogen, cat#. 18324010) to create NSCs where the expression of either MEK1 or MEK2 or both are inhibited.

After 4 hours, the culture medium of these transfected cells was replaced with N2 culture medium, cultured for an additional 4 days, and then RNA was extracted using the method in Example 4-1. The NSC to neuron differentiation-inducing ability was analyzed by reverse transcription PCR (RT-PCR). Specifically, RNA was converted to cDNA through reverse transcription, and then EX-Taq DNA polymerase (SG Bio, Kyunggi Do, Korea) and primer were added to perform PCR in the T100TM Thermal Cycler (Bio-rad, Hercules, Calif.). PCR was performed by incubating at 95° C. for 5 minutes, then repeating 25-35 cycles of reaction where 1 cycle consists of incubating at 95° C. for 30 seconds, at 55~62° C. for 30 seconds, and at 72° C. for 30 seconds. The PCR results were examined by performing gel electrophoresis on 2% agarose gel, which was then analyzed by an image analyzer, LAS-3000 (Fujifilm, Tokyo, Japan).

The primers used for RT-PCR and qRT-PCR in the present Example as well as Example 5-2 and 5-3 are shown in Table 4.

TABLE 4

| Gene | Forward Primer | Reverse Primer |
| --- | --- | --- |
| GAPDH | 5'-CGTGCCGCCTGGAGAA ACC-3' (SEQ ID NO: 1) | 5'-TGGAAGAGTGGGAGTTGCTGTT G-3' (SEQ ID NO: 4) |

TABLE 4-continued

| Gene | Forward Primer | Reverse Primer |
| --- | --- | --- |
| Tuj1 | 5'-GGTCTGGCGCCTTTGG A-3' (SEQ ID NO: 2) | 5'-CACCACTCTGACCAAAGATAAA GTTG-3' (SEQ ID NO: 5) |
| TH | 5'-AGGTATACGCCACGCT GAAG-3' (SEQ ID NO: 3) | 5'-CTCGGGTGAGTGCATAGGTG-3' (SEQ ID NO: 6) |
| MEK1 | 5'-CGGCGGTTAACGGGAC CA-34' (SEQ ID NO: 15) | 5'-GGATTGCGGGTTTGATCTC CA-3' (SEQ ID NO: 17) |
| MEK2 | 5'-CCTGGATGAGCAGCAA AGGA-3' (SEQ ID NO: 16) | 5'-CAGTGAGCCACCATCCATGT-3' (SEQ ID NO: 18) |

The results are shown in FIG. 8a. As shown in FIG. 8a, expression of the dopamine neuron marker TH is significantly increased in the NSC where both MEK1 and MEK2 are inhibited by the transfection of both shMEK1 and shMEK2 (shMEK1+, shMEK2+) in comparison to NSC where only MEK2 expression is inhibited (shMEK1−, shMEK2+).

Figure 8B:
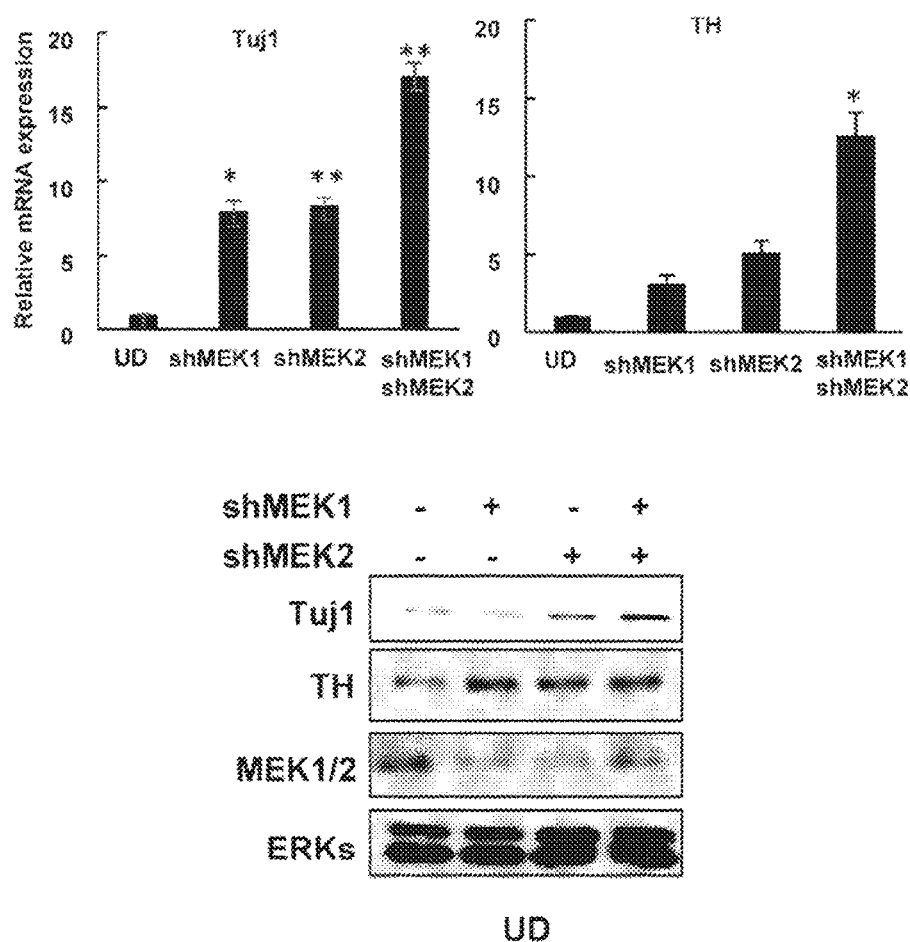
FIG. 8b is part of the result of Example 5-1 that shows the relative mRNA expression levels of Tuj1 and TH in mouse embryonic neural stem cells where either MEK1 or MEK2 or both MEK1 and MEK2 expression are inhibited by shMEK1 and shMEK2, and confirms the presence or absence of the Tuj1 and TH proteins though western blotting.

In order to examine once more the effect of inhibiting only MEK1 or MEK2 or inhibiting both MEK1 and MEK2, the NSC to neuron differentiation-inducing effect was examined by qRT-PCR and western blotting. NSC where only MEK1 or MEK2 are inhibited and NSC where both MEK1 and MEK2 are inhibited were produced with the aforementioned methods. After 4 hours, the culture medium of the transfected cells was replaced with N2 culture medium, cultured for an additional 4 days, and qRT-PCR performed using the method in Example 4-1. The results are shown in the graph of FIG. 8b. As shown in the graph of FIG. 8b, expression of the neuron markers Tuj1 and TH is significantly increased when both MEK1 and MEK2 expression is inhibited compared with when only MEK1 or MEK2 is.

Western blotting was performed to examine if the NSC to neuron differentiation-inducing effect is seen with the inhibition of MEK1 and MEK2 expression, not only in mRNA but also in protein levels.

Western blotting was performed on each group of cells by the following method: After culturing the NSC where MEK1 and MEK2 expression is inhibited for 4 days, medium was removed, RIPA buffer (0.05 M Tris HCl pH7.4 (Sigma, cat#.T3253), 0.15 M NaCl (Ducsan, cat#. 7647-14-5), 0.25% deoxycholic acid (Sigma, cat#.D6750), 1% NP-40 (USB, Waltham, Mass., cat#.19628), 1 mM EDTA (Sigma, cat#.EDS), 1 mM PMSF (Acros organics, Geel, Belgium, cat#. 215740050), 1 mM sodium orthovanadate (Bio labs, Ipswich, Mass., cat#. P0758L), 1 mM sodium fluoride (Sigma, cat#.S7920), protease inhibitors (Sigma, cat#.P83430)) was added into the plate on ice, and cells were collected with a scrapper. After incubation on ice for 10 minutes, the supernatant was collected after centrifugation at 13000 rpm at 4° C. The protein concentration was measured, sample buffer (0.25 M Tris-HCl pH6.8, 0.05% SDS (Amersco, Solon, Ohio, cat#. 227), 50% glycerol (Ducsan, cat#. 56-81-5), 0.25 M DTT (Invitrogen, cat#.R0861), 0.5 mg/ml BPB (Bio-rad, Hercules, Calif., cat#.161-0404) was added, and the sample was boiled at 100° C. for 10 minutes and then stored at −20° C.

10~20 μg protein samples were loaded onto 8~12% SDS-PAGE gel, separated, and transferred to a nitrocellulose membrane, which was then blocked with 5% skim milk at room temperature for 1 hour. Antibodies against Tuj1, TH (Cell signaling, cat#. 2792), MEK1/2 (Santa Cruz, Dallas, Tex., cat#. Sc-292838), and ERK (Santa Cruz, cat#. Sc-135900) were each prepared in 0.1% Tween 20 (Sigma, cat#. P1379) containing tris buffered saline (TBS) and incubated with the membrane at room temperature for 2 hours or at 4° C. overnight, after which it was incubated with a horseradish peroxidase-conjugated secondary antibody at room temperature for 1 hour. Protein expression was detected with a photosensitive equipment and the result is shown in the bottom picture of FIG. 8b. As shown in FIG. 8b, the expression levels of both mRNA and proteins in the neuron marker Tuj1 and dopamine neuron marker TH significantly increased in NSC where MEK1 and MEK2 expression are both inhibited by the use of both shMEK1 and shMEK2 (shMEK1+, shMEK2+).

In contrast, in the case of NSC where only one of MEK1 or MEK2 expression is inhibited, a lower level of expression of Tuj1 and TH is seen compared with that of NSC with both MEK1 and MEK2 inhibition.

Example 5-2

Inducing Expression of CAMEK1 and CAMEK2 in Mouse Embryonic Neural Stem Cells

In order to examine the NSC to neuron differentiation-inducing effect in relation to the activation of MEK1 and MEK2, a constitutively active MEK1 (CAMEK1) plasmid and constitutively active MEK2 (CAMEK2) plasmid that have mutations for the constitutive expression of MEK1 and MEK2, respectively, were used in the experiments. Specifically, mouse embryonic NSC cultured as described in Example 1, Step 1A were seeded into plates and incubated for 24 hours. Then, 1 µg/ml CAMEK1 and CAMEK2 were transfected into the cells using lipofectamine to create NSC where the expression of either CAMEK1 or CAMEK2 or both are expressed. After 4 hours, the culture medium of these transfected cells was replaced with N2 culture medium that does not contain EGF or bFGF, cultured for an additional 4 days, RNA and protein were extracted, and quantitative RT-PCR (qRT-PCR) and western blotting were performed. Through these experiments, the effect of MEK1 and MEK2 activation on the NSC to neuron differentiation-inducing effect was examined and shown in FIG. 8c.

Figure 8C:
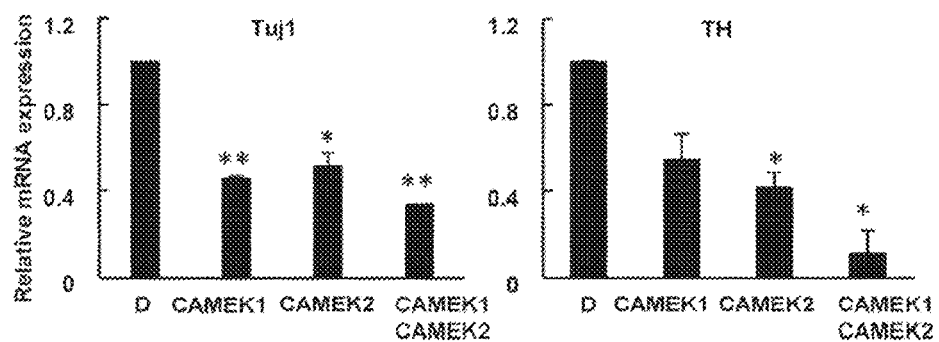
FIG. 8c is part of the result of Example 5-2 that shows the relative mRNA expression levels of Tuj1 and TH in mouse embryonic neural stem cells where either MEK1 or MEK2 or both MEK1 and MEK2 expression are activated by CAMEK1 and CAMEK2, and confirms the presence or absence of the Tuj1 and TH proteins though western blotting.
Figure 8C:
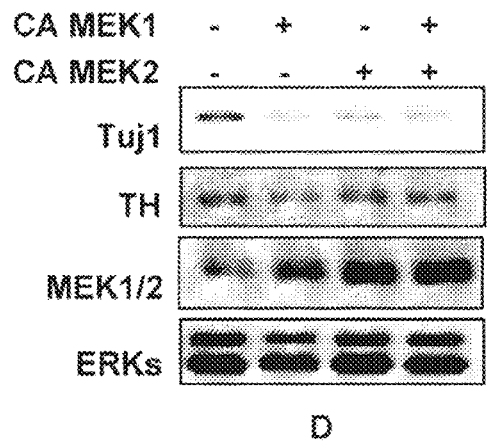

In contrast to FIG. 8b, FIG. 8c shows that when MEK1 and MEK2 are activated in an otherwise differentiation-inducing environment, differentiation of the NCS are inhibited. mRNA and protein expression of the neuron marker Tuj1 and the dopaminergic neuron marker TH were shown to be inhibited by qRT-PCR and western blotting. The expression of Tuj1 and TH was significantly lower in the case of both MEK1 and MEK2 activation in comparison with only one of them being activated.

Example 5-3

Inhibition of MEK1 and MEK2 in Mouse Adult Neural Stem Cells

The following experiments were performed to determine if the inhibition of MEK1 and MEK2 induces the differentiation of NSC in mouse adult NSC and if the effect is the same in conditions where amyloid-beta is present.

Mouse adult NSCs cultured as described in Example 2, Step 1A were seeded into plates and cultured for 24 hours. Then 1 µg/ml shRNA-MEK1 (CCGGGCCATCCAACAT-TCTAGTGAACTCGAGTTCACTAGAATGTTGGATG GCTTTTT (SEQ ID NO: 13)) or shRNA-MEK2 (CCGGCCTCCGAGAGAAGCACCAGATCTCGAGA-TCTGGTGCTTCTCTCGGA GGTTTTTG (SEQ ID NO: 14)) were transfected into the cells using lipofectamine (Invitrogen) to create NSC where the expression of either MEK1 or MEK2 or both are inhibited.

After 4 hours, the culture medium of these transfected cells was replaced with N2 culture medium or N2 medium treated with 10 µM amyloid-beta, cultured for an additional 2 days, and cell morphology observed under a microscope. RNA was extracted using the method in Example 4, qRT-PCR was performed, and the NSC to neuron differentiation-inducing effect was analyzed.

The result is shown in FIG. 9.

Figure 9A:
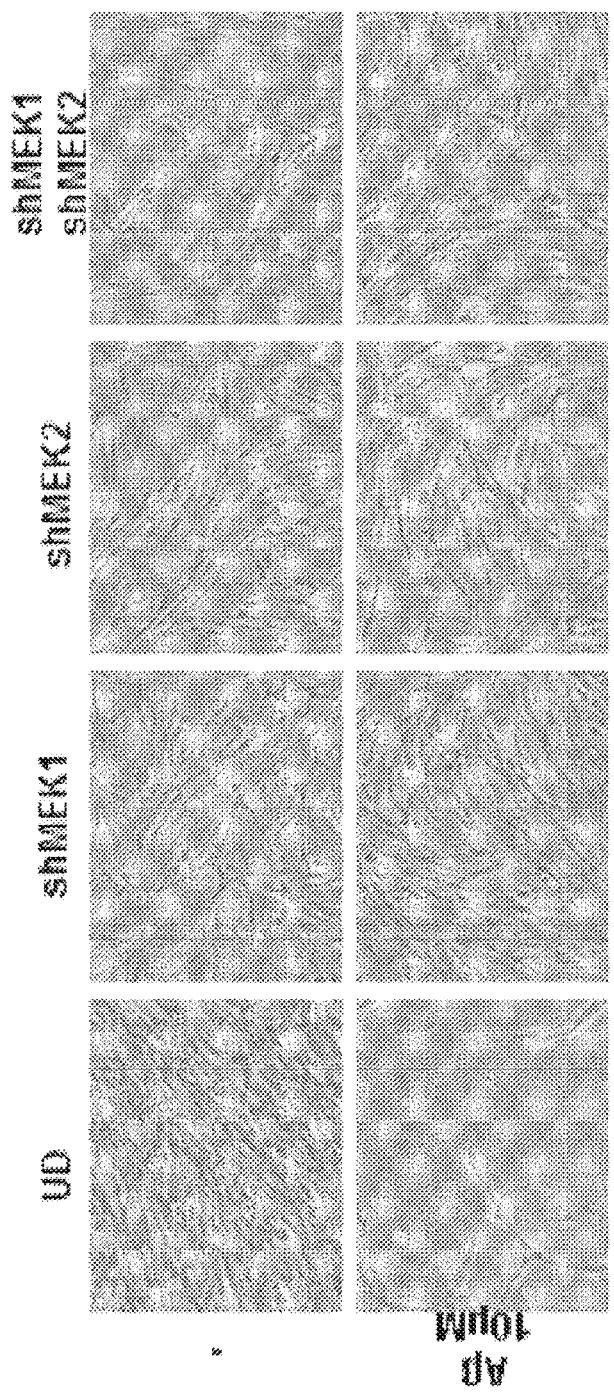
FIGS. 9a-9b are the result of Example 5-3 that shows cell morphology observations as seen by phase-contrast microscopy (FIG. 9a) and the analysis of the relative mRNA expression levels of the neuronal marker Tuj1 (FIG. 9b) in Aβ-treated or non-treated mouse adult neural stem cells where either MEK1 or MEK2 or both MEK1 and MEK2 expression are inhibited by shMEK1 and shMEK2.

As shown in FIG. 9a, differentiation was more readily induced in NSC where both MEK1 and MEK2 expression was inhibited by the transfection of both shMEK1 and shMEK2 than in NSC where only one of shMEK1 or shMEK2 was transfected.

In the case of Aβ-treated cells, cells died in the group where both MEK1 and MEK2 were not inhibited, but in the group where either MEK1 or MEK2 or both MEK1 and MEK2 were inhibited, cell death did not occur but induction of differentiation did.

Figure 9B:
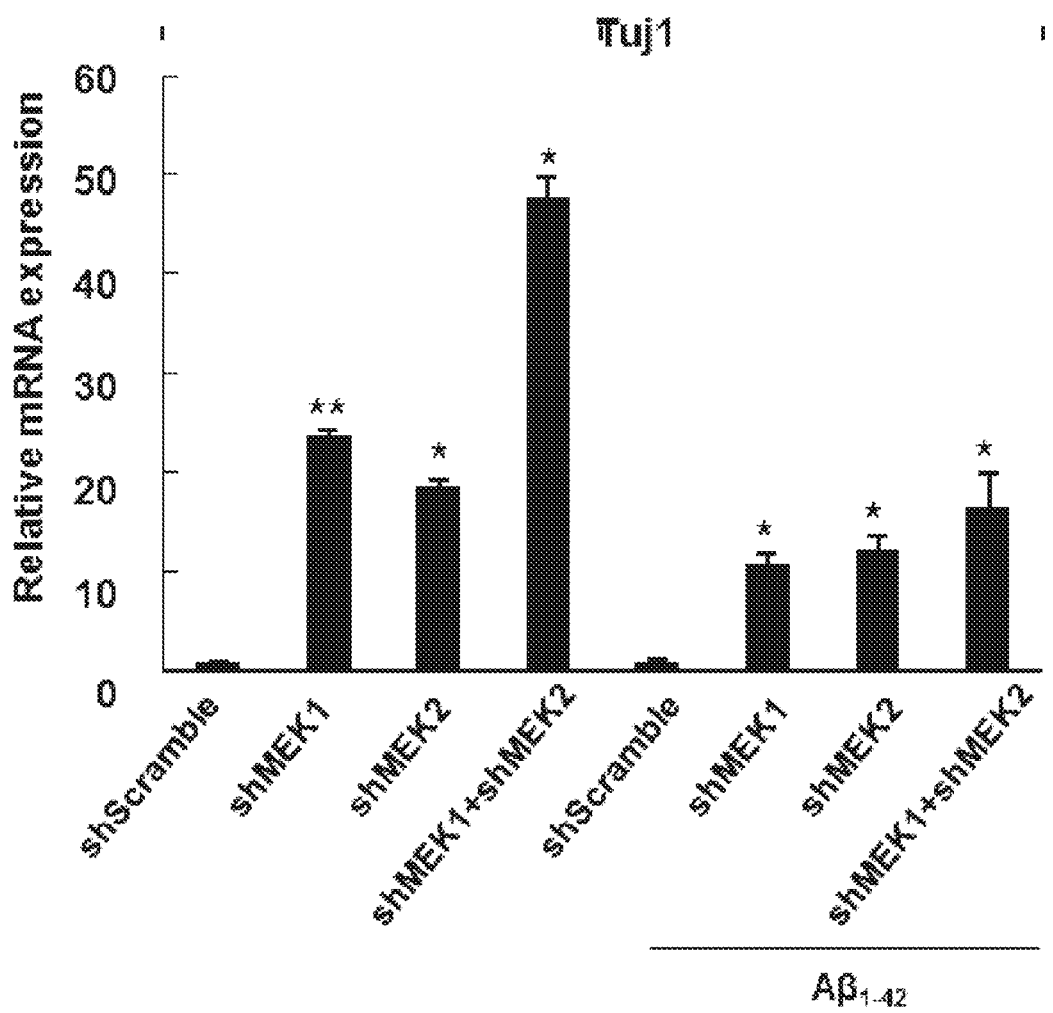

Also, as shown in FIG. 9b, expression of the neuronal marker Tuj1 was significantly increased in the NSC where both MEK1 and MEK2 expression was inhibited by the treatment of both shMEK1 and shMEK2 (shMEK1+ shMEK2). In contrast, in NSCs where the expression of either MEK1 or MEK2 was inhibited (shMEK1, shMEK2), expression of the neuron marker Tuj1 was low as was the NSC to neuron differentiation-inducing effect compared to the case where both MEK1 and MEK2 were inhibited. In the case of Aβ-treated cells, some protective and differentiation-inducing effect was seen in NSCs where either MEK1 or MEK2 was inhibited, but in the NSC where both MEK1 and MEK2 expression was inhibited, the protective and differentiation-inducing effect was significantly higher.

From these results, it is revealed that the inhibition of MEK1 and MEK2 in adult NSC not only induces the differentiation of NSC, but also demonstrates a protective effect against amyloid-beta.

Example 6

NSC Differentiation-Inducing Effect of Other MEK1/2 Inhibitors

Figure 10A:
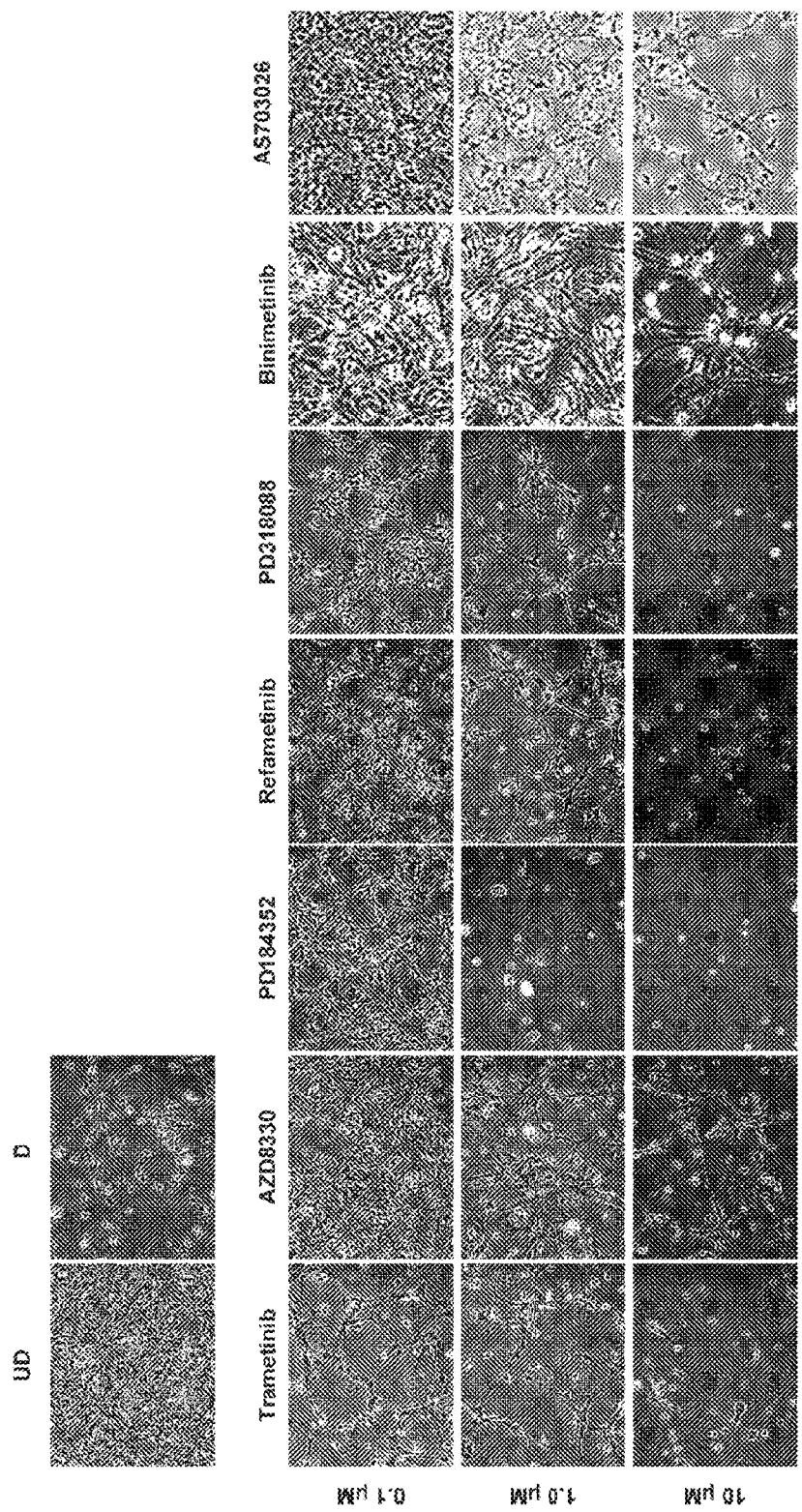
FIGS. 10a-10c are the result of Example 6 that shows cell morphology observations as seen by phase-contrast microscopy (FIG. 10a) and the relative mRNA expression level of Tuj1 (FIG. 10b) in mouse embryonic neural stem cells treated with MEK1/2 inhibitors trametinib, AZD8330, PD184352, refametinib, PD318088, binimetinib, and AS703026 in concentrations of 0.1 μM, 1.0 μM, and 10 μM.
Figure 10B:
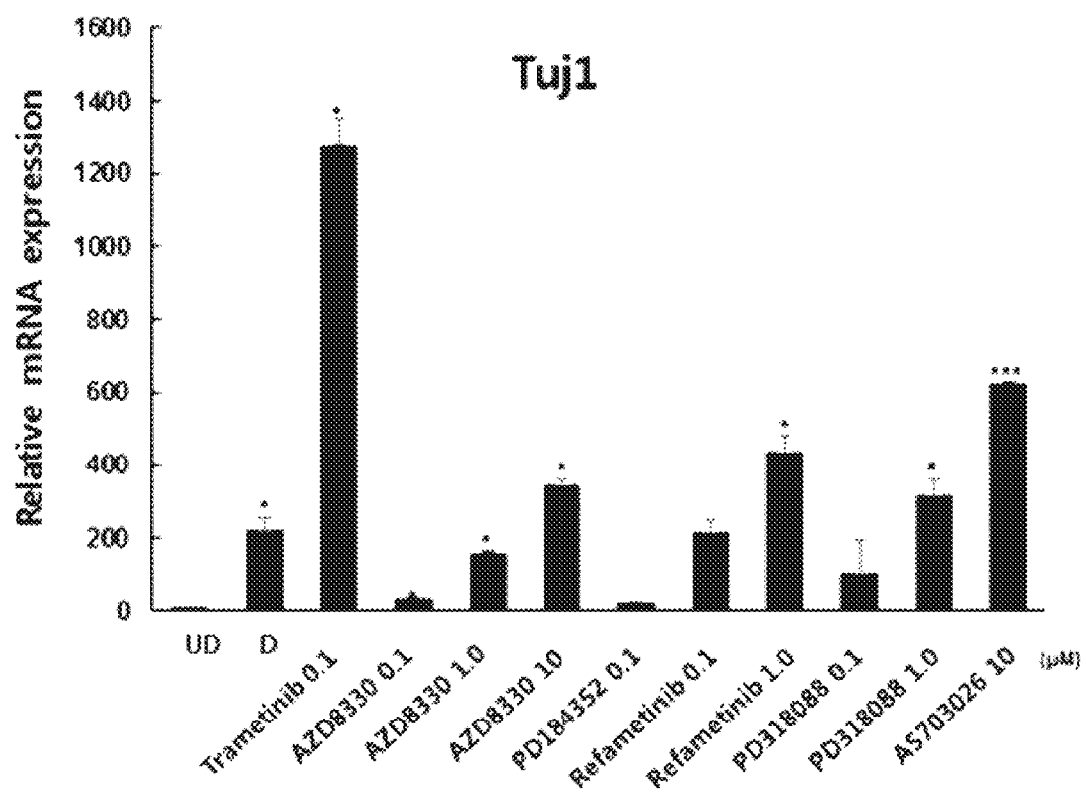

In order to test if other MEK 1/2 inhibitors besides trametinib demonstrate a NSC differentiation-inducing and protective effect, mouse embryonic NSCs were treated with each of the test material. Specifically, mouse embryonic NSCs cultured as described in Example 1, Step 1A were treated with the respective MEK1/2 inhibitors AZD8330 (Selleckchem, cat#. 2134), PD184352 (Selleckchem, cat#. S1020), refametinib (Selleckchem, cat#. S1089), PD318088 (Selleckchem, cat#. S1568), binimetinib (Selleckchem, cat#. S7007), and AS703026 at concentrations of 0.1 µM, 1.0 µM, and 10 µM and incubated. For comparison, NSCs were also treated with trametinib at the same concentrations. On day 2 of culture, cell morphology was observed by phase-contrast microscopy and the results are shown in FIG. 10a. FIG. 10b is the analysis of Tuj1 mRNA expression in the cells of each group.

As shown in FIGS. 10a and 10b, AZD8330, refametinib, PD318088, binimetinib, and AS703026 all induced differentiation, albeit starting at different concentrations.

AZD8330, refametinib, and PD318088 exhibited differentiation morphology starting at 1.0 μM, while binimetinib and AS703026 started at 10 μM. Examining the expression of the neuronal differentiation marker Tuj1 by RT-PCR also showed that they induce differentiation at the same concentrations. Trametinib showed an excellent NSC differentiation-inducing effect compared with other compounds, even at a low concentration of 0.1 μM. In contrast, PD184352 showed only a weak NSC differentiation-inducing effect at 0.1 μM, and at 1.0 μM and 10 μM, all the cells died.

Figure 10C:
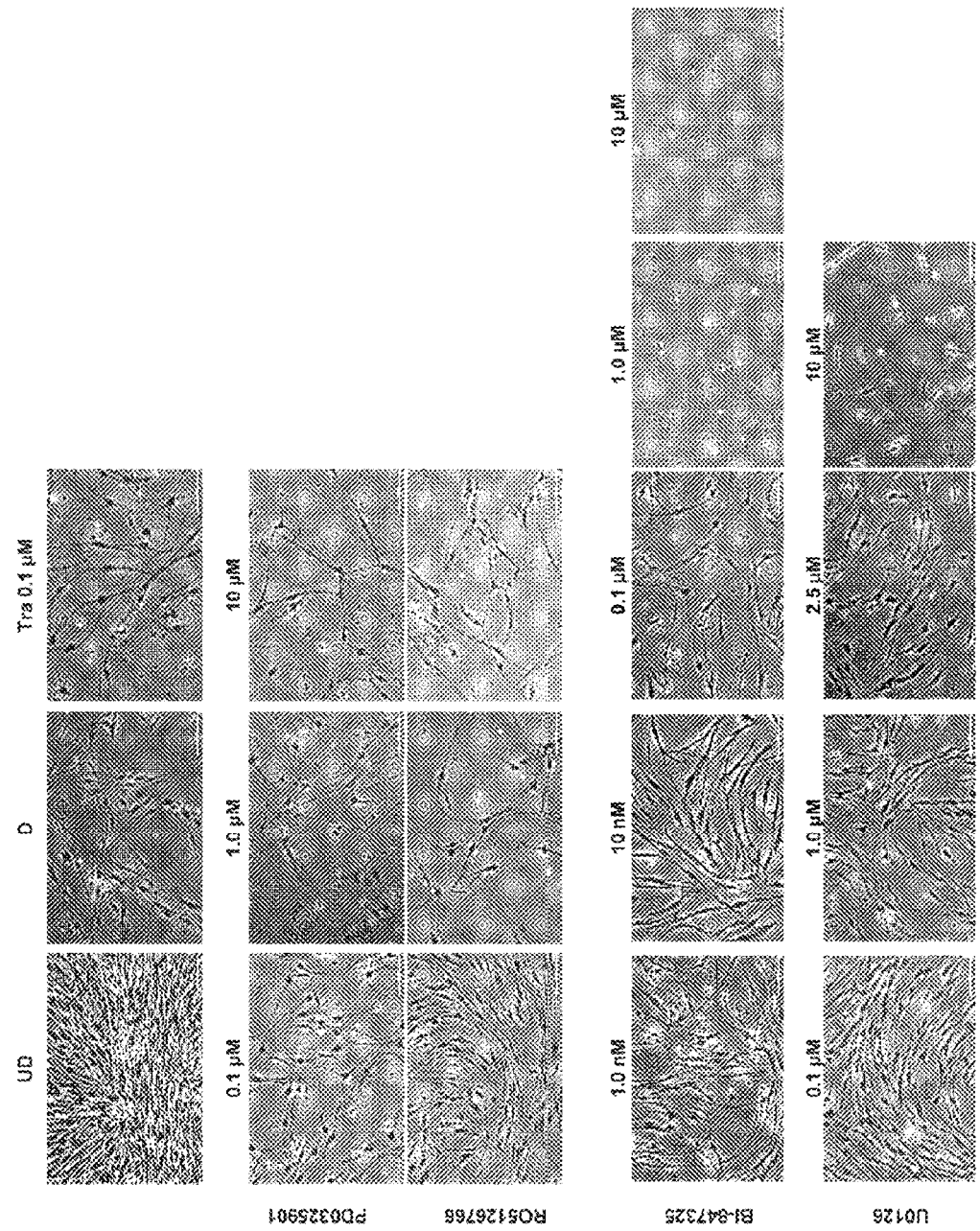

In addition, mouse adult NSCs cultured as in Example 2, Step 1A were treated with other MEK 1/2 inhibitors PD0325901 (Selleckchem, cat#. S1036), RO5126766 (Selleckchem, cat#. S7170), BI847325 (Selleckchem, cat#. S7843), and U0126 (A.G. Scientific, San Diego, Calif., cat#. U-102) at various concentrations, and their NSC differentiation-inducing effects were examined. After treatment with the test materials, cell morphology was observed by phase-contrast microscopy on day 2 of culture. The results are shown in FIG. 10c. As shown in FIG. 10c, PD0325901 showed a differentiation-inducing effect starting at 0.1 μM, RO5126766 at 1.0 μM. PD0325901, in particular, showed an excellent inducing effect as it induced differentiation over a wide range of concentrations, from 0.1 μM to 10 μM. In contrast, BI847325 showed only a weak differentiation-inducing effect at 0.1 μM, and at 1.0 μM and 10 μM, all the cells died. When treated with lower concentrations of BI847325 (1.0 nM and 10 nM), cell proliferation seemed to be somewhat inhibited and a differentiation-inducing effect was not observed. U0126 showed inhibition of cell proliferation at 0.1 μM and 1.0 μM and at 10 μM, showed cell cytotoxicity. Furthermore, U0126 did not show any clear differentiation-inducing effect at 2.5 μM and thus failed to show any NSC differentiation-inducing effect at all concentrations tested.

These results reveal that not all previously known MEK1/2 inhibitors effectively induce NSC differentiation. According to the results of Example 5, it is clear that MEK1 and MEK2 inhibition is involved in inducing the differentiation of NSC. However, it is thought that the distinct property of each MEK 1/2 inhibitor affects its NSC differentiation-inducing abilities, leading to differences seen in Example 6.

Example 7

NSC Differentiation-Inducing Effect of Other MEK1/2 Inhibitors in the Presence of Cell Cytotoxic Factors Adult NSC cultured as described in Example 2, Step 1A were treated with 10 μM amyloid-beta as described in Example 2, Step 2 to create a cytotoxic environment, after which MEK1/2 inhibitors AS703026 (10 μM), AZD8330 (1 μM), PD318088 (1 μM), binimetinib (10 μM), refametinib (1 μM), PD0325901 (10 μM), and RO5126766 (10 μM) were added at the concentration that caused the most differentiation-inducing effect in Example 6 and cultured. For comparison, 0.1 μM trametinib-treated group and 10 μM cobimetinib (known as a selective inhibitor of MEK1 compared with MEK2)-treated group, as well as amyloid-beta non-treated groups for each of the tested compound were included. Cell morphology was observed by phase-contrast microscopy on the second day of culture and the results are shown in FIG. 11.

Figure 11:
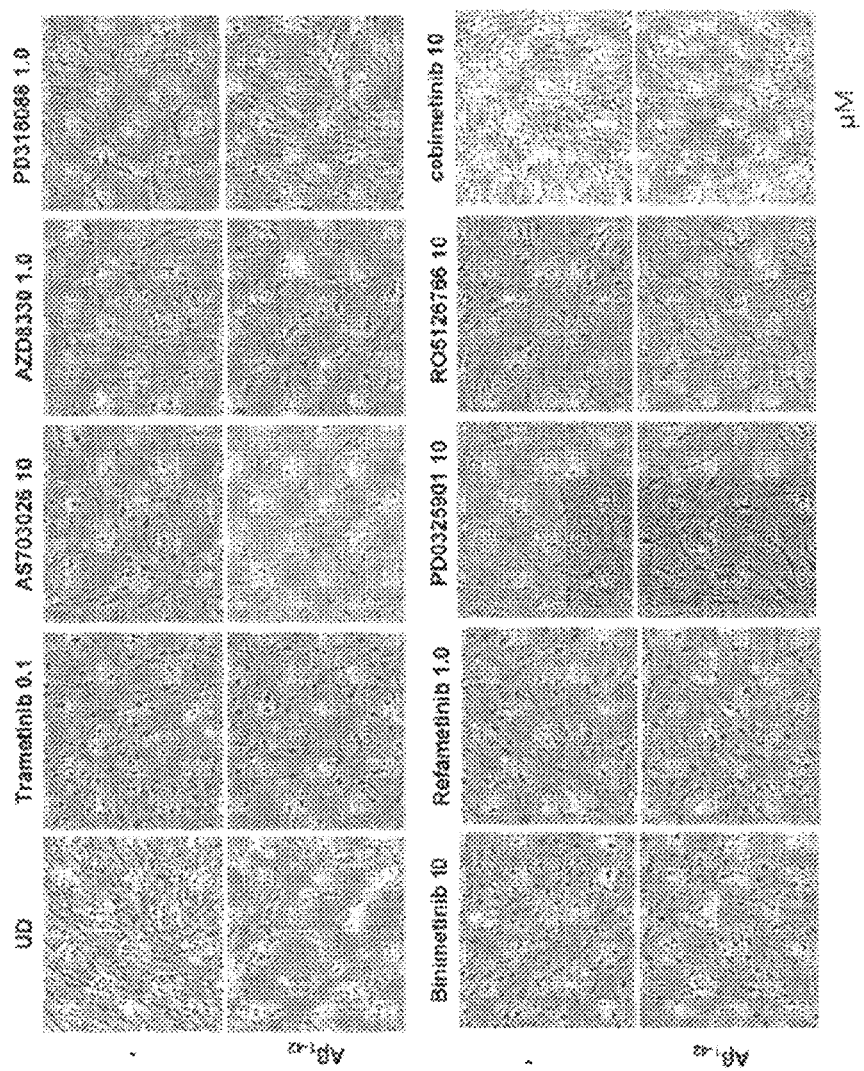
FIG. 11 is the result of Example 7 that shows cell morphology observations as seen by phase-contrast microscopy of Aβ-treated or non-treated mouse adult neural stem cells that were then subjected to treatment with MEK1/2 inhibitors trametinib (0.1 μM), AS703026 (10 μM), AZD8330 (1 μM), PD318088 (1 μM), binimetinib (10 μM), refametinib (1 μM), PD0325901 (10 μM), RO5126766 (10 μM), and cobimetinib (10 μM) which is known to be a selective inhibitor of MEK1 compared with MEK2. The rows marked with "-" are cells not treated with amyloid-beta and the ones marked with "Aβ1-42" are cells treated with 10 μM amyloid-beta.

In FIG. 11, the row marked "-" is the mouse adult NSC group that is not treated with amyloid-beta and the row marked "Aβ1-42" is the group treated with 10 μM amyloid-beta. In conditions where cytoxicity is caused by the treatment of 10 μM amyloid-beta, it was shown that the addition of AS703026, AZD8330, PD318088, binimetinib, refametinib, PD0325901, and RO5126766, at each of the optimal concentration that induces the most differentiation, provided cell protection and induced the differentiation of NSC. In contrast, the addition of cobimetinib, an inhibitor known to be more selective to MEK1 than MEK2, did not induce the differentiation of adult NSC even at a high concentration of 10 μM, regardless of whether or not amyloid-beta was added.

Example 8

Detection of an Increase in the Number of Neurons in the Alzheimer's Disease Mouse Model Through these previous experiments, it was shown that among the compounds that suppress both MEK1 and MEK2, certain compounds induce the differentiation of NSC into neurons and protect NSC and neurons against amyloid-beta, trametinib, in particular, showing a powerful effect. To confirm this finding in the neurodegenerative disease mouse model as well, the neuro-regeneration and therapeutic effect of trametinib was examined using the 5XFAD mouse, an animal model that shows symptoms of AD which is the most common form of neurodegenerative disease. The 5XFAD mouse displays neuronal pathologies, the degeneration and cell death of neurons, especially in the somatosensory cortical layer 5 and subiculum of the brain (Oakley et al. (2006) Intraneuronal beta-amyloid aggregates, neurodegeneration, and neuron loss in transgenic mice with five familial Alzheimer's disease mutations: potential factors in amyloid plaque formation. J Neurosci. 26(40):10129-10140).

Trametinib was administered orally to the 5XFAD (B6SJL-Tg (APPSwFlLon,PSEN1*M146L*L286V) 6799Vas/Mmjax) AD model mice at 12 months of age daily for 28 consecutive days at a dose of 0.1 mg/kg and 1.0 mg/kg, whereas vehicle (4% DMSO+Corn oil) was administered to the control group mice in the same method (7 mice/group). For the BrdU staining to be performed later, 50 mg/kg of BrdU (Sigma, cat#. B5002) was added to the daily dose for the last 5 days. The mouse was then anesthetized and perfused with PBS for the extraction of the brain. Of the brains extracted from 3 mice of each group, half of the brain tissue (hemispheres) was immediately stored in the deep freezer for western blotting and ELISA experiments to be performed later. The other half of the hemispheres plus another 3 extracted mice brains per group were placed in 10% formalin solution at 4° C. for 1 day, which was then followed with the proceeding steps to allow good penetration of paraffin into the brain tissue. The brain tissues were immersed sequentially in 70%, 80%, 95%, 100% alcohol for 1 hour each for dehydration, then immersed in xylene 3 times for 1 hour each for clearing, and embedded in paraffin by placing in liquid paraffin 2 times for 1 hour each. After these procedures, the paraffin-embedded brain tissue (paraffin block) was cut into 5 μm sections, mounted on slides, and stored at room temperature. Prior to immunohistochemical staining, the tissues on the slides were rehydrated by sequentially immersing in xylene, 100%, 90%, 80%, 70%, 50% alcohol,and then water for 5 minutes each. After placing in sodium citrate (10 mM, pH 6) (Sigma, S4641) buffer, antigen retrieval process was performed at 120° C. for 15 minutes, blocked with 10% BSA (Bovine serum albumin), and incubated with antibodies against the neuronal marker NeuN (Cell signaling, cat#. 24307) at 4° C. for 1 day. The next day, the slides were incubated with anti-rabbit antibodies (Vector lab, cat#. PI-1000) at room temperature for 1 hour and then stained with DAB staining for the analysis of the neuronal distribution in the brain.

Since the 5XFAD mouse is known to have extensive neuronal damage in the cerebral cortex layer 5 and hippocampal subiculum, these regions of the brain were examined first.

Figure 12A:
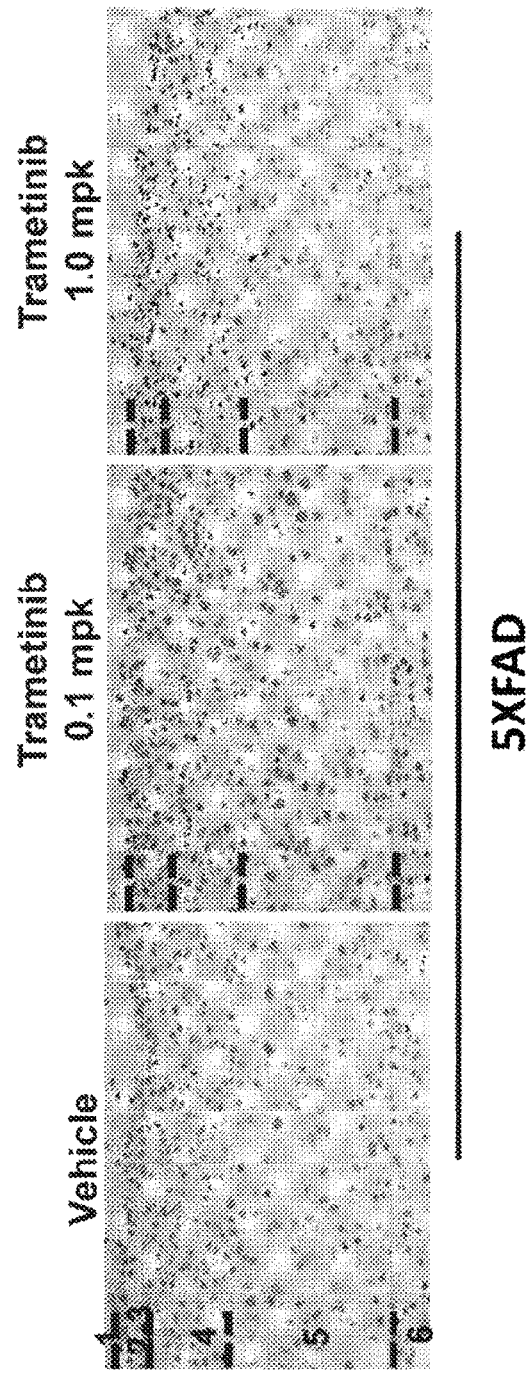
FIGS. 12a-12b are part of the result of Example 8 that shows NeuN immunohistochemical staining in slices in the somatosensory cortex of trametinib-administered 5XFAD mice (FIG. 12a).
Figure 12B:
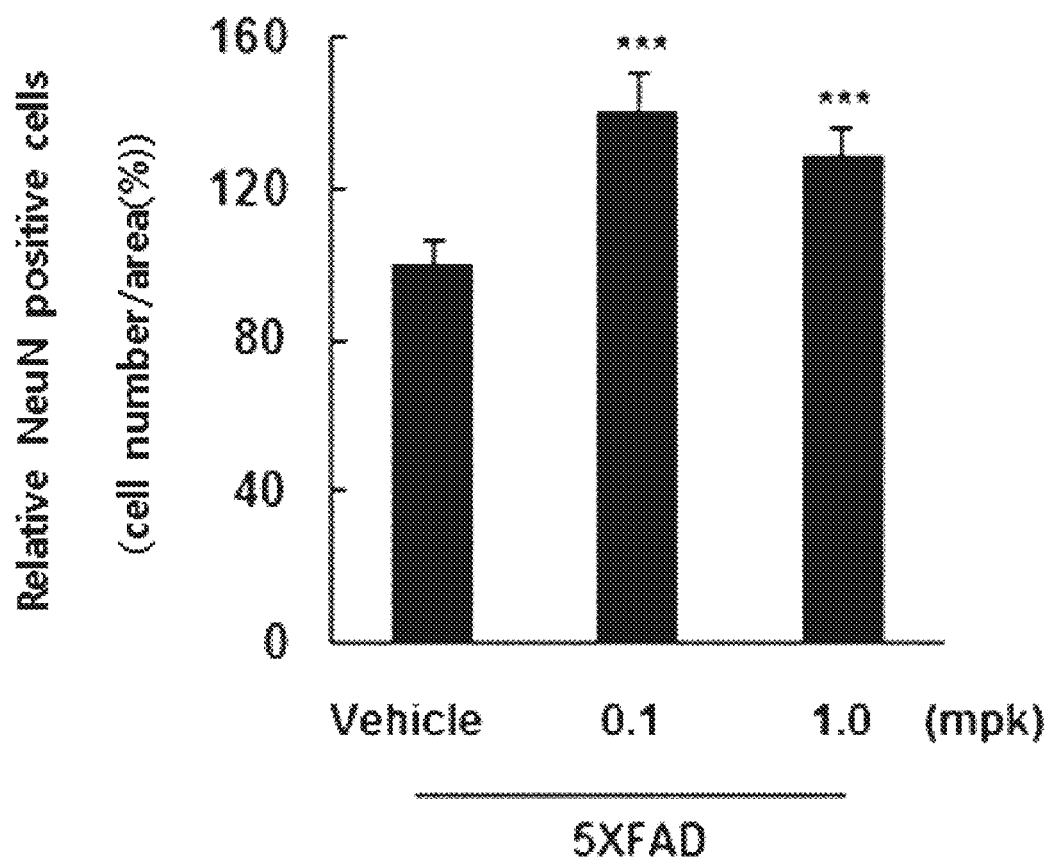

FIG. 12 is the result of the analysis of the sagittal sections of the somatosensory cortex in the cerebral cortex. As shown in FIG. 12a, in the vehicle (4% DMSO+corn oil)-administered 5XFAD mouse (control, first left picture), the number of NeuN (positive) stained cells have decreased due to considerable damage of neurons in the cerebral cortex layer 5. In comparison, 0.1 mg/kg and 1.0 mg/kg trametinib-administered 5XFAD mouse showed a significant increase in the number of neurons stained with NeuN. FIG. 12b indicates the number of NeuN stained cells counted and represented as the percentage of the number of cells per unit area in the somatosensory cortex layer 5 region. Area samples were taken from 3 areas per mouse, 3 mice per group, so the number of cells counted was from a total of 9 areas. The percentage of the number of NeuN stained cells in the trametinib-administered group compared with the vehicle-administered group was calculated and shown.

Figure 13A:
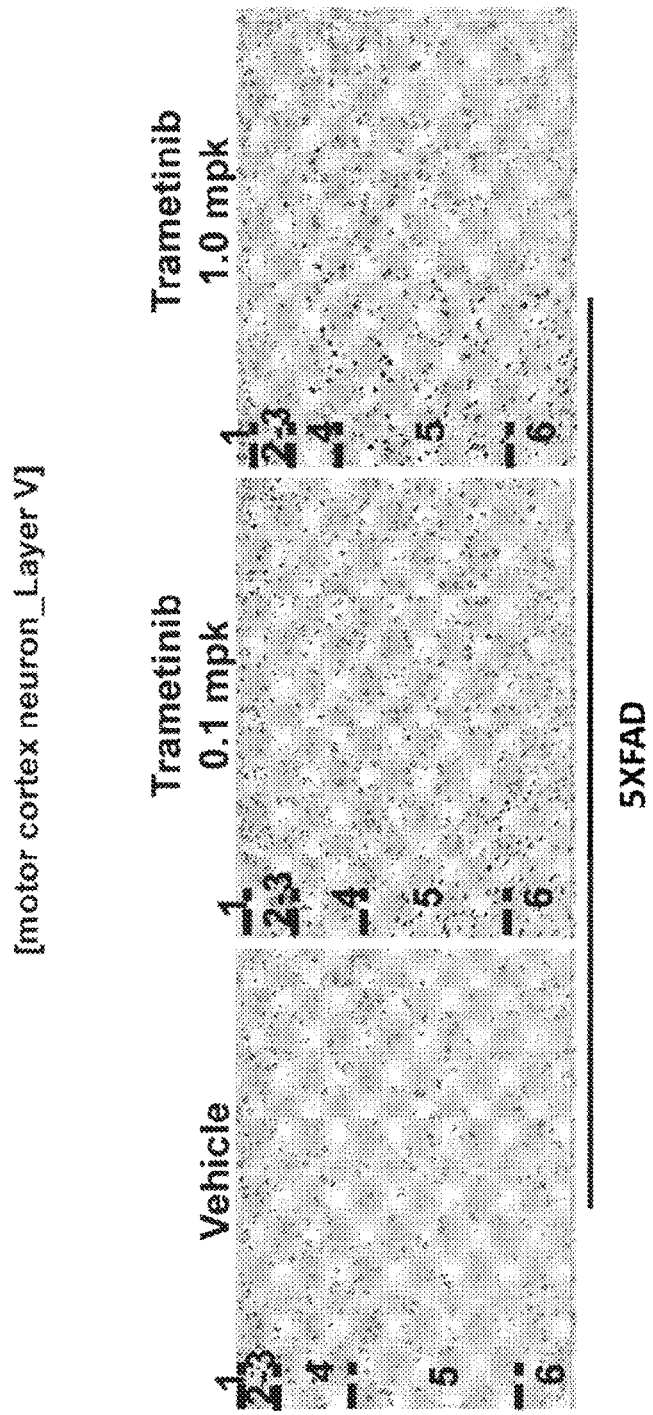
FIGS. 13a-13b are part of the result of Example 8 that shows NeuN immunohistochemical staining in slices of the motor cortex of trametinib-administered 5XFAD mice (FIG. 13a).
Figure 13B:
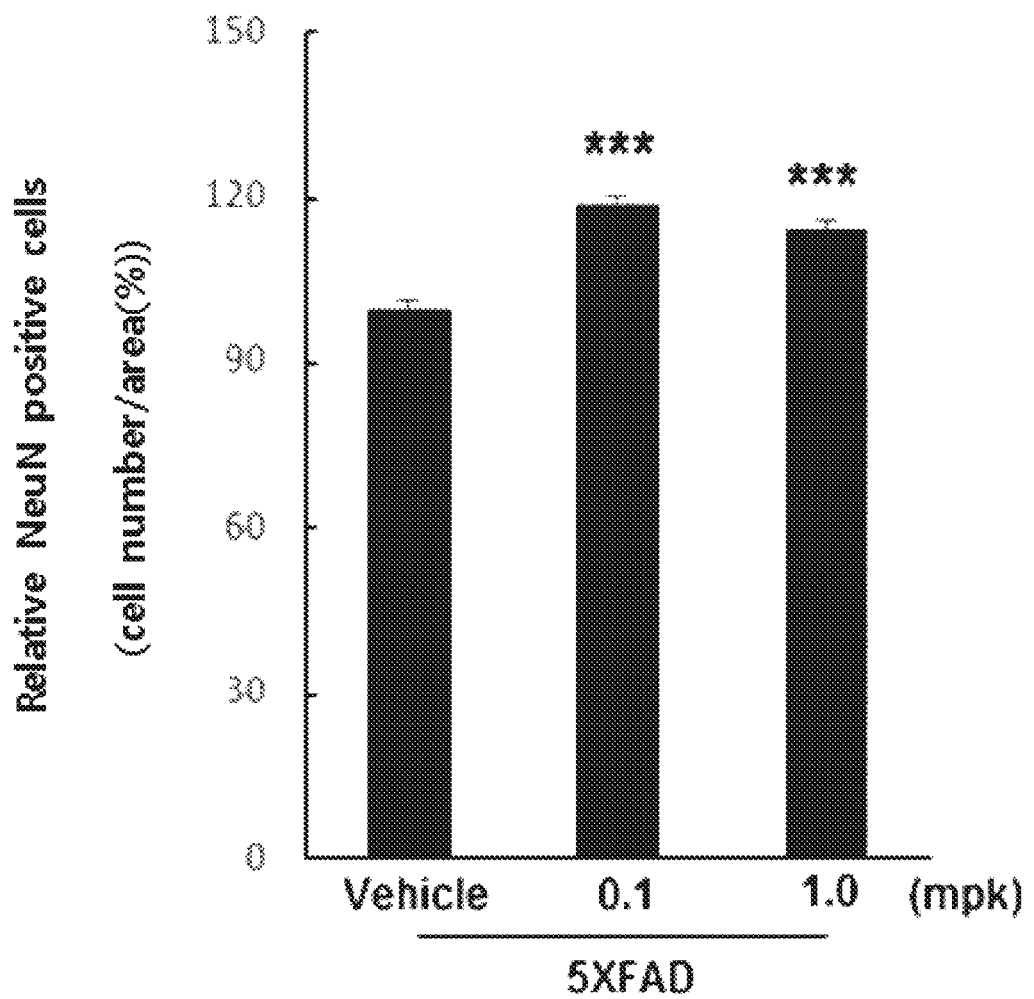

FIG. 13 is the result of the analysis of the coronal sections of the motor cortex in the mouse cerebral cortex. As shown in FIG. 13a, the vehicle-administered 5XFAD mouse (control) showed extensive neuronal damage in the motor cortex layer 5 with a decreased number of NeuN stained neurons, while the trametinib-group again showed a significant increase in the number of neurons, as with the results of the somatosensory cortex. FIG. 13b indicates the number of NeuN stained cells counted and represented as the percentage of the number of cells per unit area in the motor cortex layer 5 region. Area samples were taken from 6 areas per mouse, 3 mice per group, so the number of cells counted was from a total of 18 areas. The percentage of the number of NeuN stained cells in the trametinib-administered group compared with the vehicle-administered group was calculated and shown.

Figure 14A:
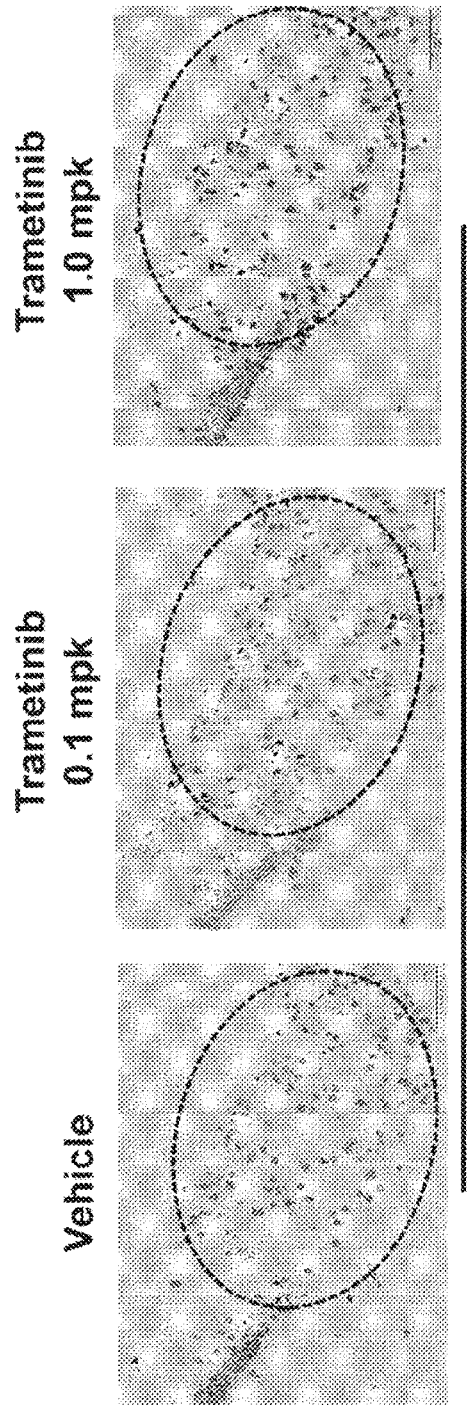
FIGS. 14a-14b are part of the result of Example 8 that shows NeuN immunohistochemical staining in slices of the hippocampal subiculum of trametinib-administered 5XFAD mice (FIG. 14a).
Figure 14B:
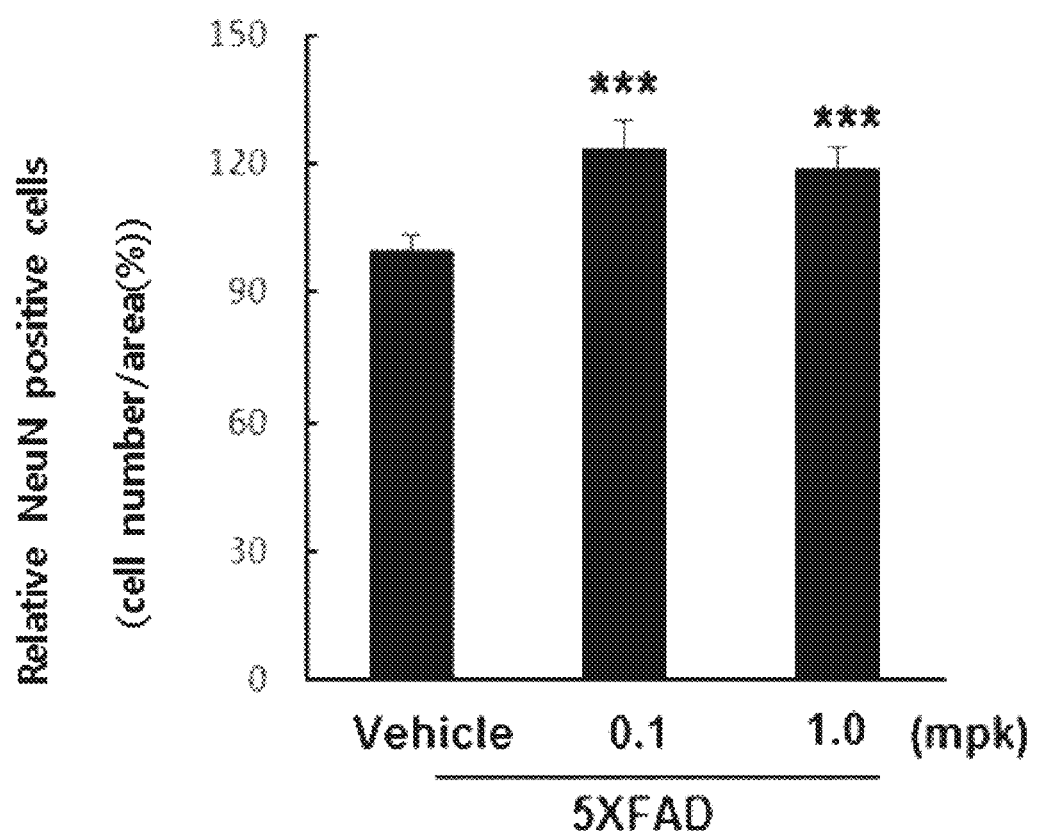

FIG. 14 is the result of the analysis of the sagittal sections of the subiculum in the mouse hippocampus. As shown in FIG. 14a, the vehicle-administered 5XFAD mouse (control) showed that a significantly small number of neurons stained with the neuronal marker NeuN in the hippocampal subiculum, while the trametinib-administered group again showed a significant increase in the number of neurons, as with the results of the cerebral cortex. FIG. 14b indicates the number of NeuN stained cells counted and represented as the percentage of the number of cells per unit area in the dotted area of the hippocampal subiculum shown in FIG. 14a. Area samples were taken from 3 areas per mouse, 3 mice per group, so the number of cells counted was from a total of 9 areas. The percentage of the number of NeuN stained cells in the trametinib-administered group compared with the vehicle-administered group was calculated and shown. Through the above experiments, it was shown that trametinib has the effect of increasing the number of neurons in the cerebral cortex layer 5 and hippocampal subiculum of the 5XFAD mouse.

Example 9

Detection of Neurogenesis in the Alzheimer's Disease Mouse Model

In order to determine if the increase in the number of neurons in the cerebral cortex layer 5 and hippocampal subiculum of the trametinib-administered 5XFAD mouse as shown in Example 8 was due to the neurogenesis effect of trametinib, immunohistochemical analysis was performed with various cell markers that appear throughout the process of NSC to neuron differentiation.

DCX (doublecortin), a protein expressed in neural precursor cells, is expressed mainly in migrating or differentiating neurons and indicates that the cell is an immature neuron in the process of neurogenesis. Tuj1 (neuron-specific class 1110 tubulin), a protein expressed in actively dividing neural precursor cells or newly generated immature postmitotic neurons, indicates that the cell is a neuron in the process of neurogenesis. Therefore, by detecting the presence of DCX or Tuj1 by immunohistochemical staining, it can be determined that neurogenesis occurs through the differentiation of NSC into neurons.

BrdU (5-Bromodeoxycytidine), an analog of the nucleobase thymidine, replaces thymidine during DNA synthesis in a diving cell, allowing the detection of dividing cells during neurogenesis by immunohistochemical staining.

Example 9-1

Detection of Tuj1 Expression in the Somatosensory Cortex of the Cerebrum

Figure 15:
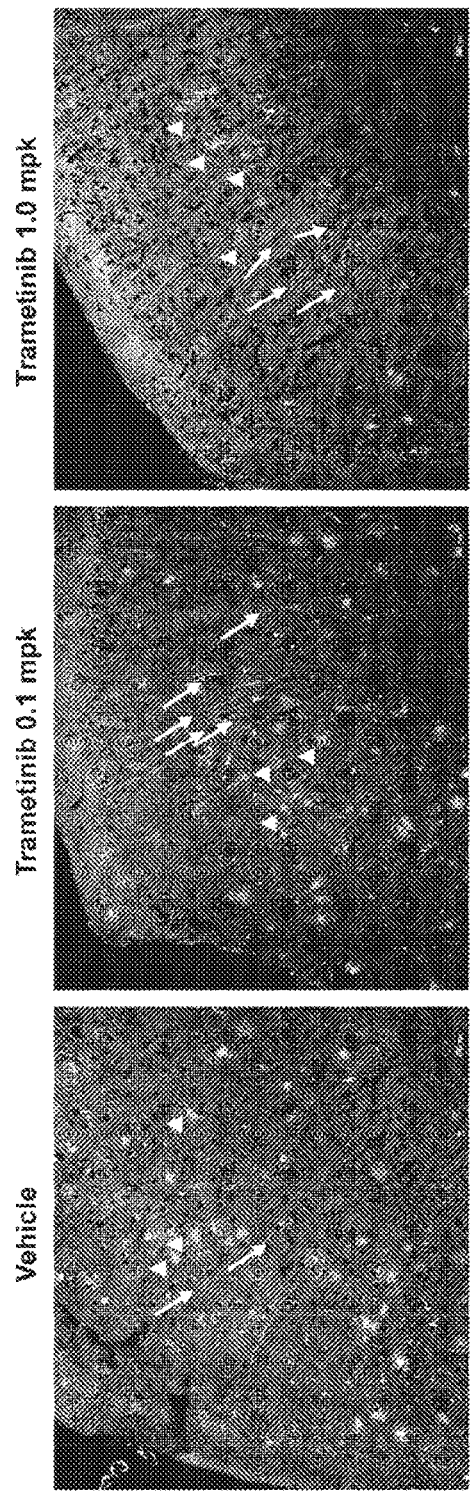
FIG. 15 is the result of Example 9-1 that shows Tuj1 immunohistochemical staining in slices of the somatosensory cortex of trametinib-administered 5XFAD mice. In the pictures, the parts marked with arrows (→) indicate cells stained with Tuj1 and the parts marked with arrowheads (▼) indicate plaques formed by amyloid-beta aggregation.

Anti-Tuj1 antibodies were added to the brain tissue slides of 5XFAD mouse in Example 8 and incubated at 4° C. for 1 day, after which the tissue slides were fluorescently stained by incubating with Fluorescein isothiocyanate (FITC)-secondary antibodies (Invitrogen, cat#. A21121) at room temperature for 1 hour. The fluorescent microscopy image of the somatosensory cortex of the cerebral cortex is shown in FIG. 15. In FIG. 15, the areas marked with arrows (→) indicate cells stained with Tuj1 and the areas marked with arrowheads (▼) indicate plaques formed by amyloid-beta aggregation. Plaques were present in both vehicle-treated and trametinib-treated groups. However, the 0.1 mg/kg trametinib-treated group, in particular, showed a significant increase in the number of cells stained with Tuj1 compared with the vehicle-treated group, despite similar levels of amyloid-beta plaques present in the samples.

Example 9-2

Detection of Niss1, NeuN, and DCX Expression in the Hippocampal Dentate Gyrus

When neurogenesis is activated in the subgranular zone (SGZ) of the dentate gyrus, asymmetric cell division takes place and as a result, Type 2 cells are generated in the very beginning. Type 2 cells have a small soma with an atypical nucleus, are short and horizontally oriented, and express nestin or Dcx. Type 3 cells are cells that have undergone further differentiation from Type 2 cells and are also called the neuroblast. Type 3 cells are cells in the early stage of differentiation in the neuronal, not glial cell lineage. Type 3 cells are situated closer towards the granular layer from the subgranular zone of the dentate gyrus and unlike Type 2 cells, have changed from the horizontally oriented to the vertically oriented shape. The fact that Type 2 and Type 3 cells are present in the subgranular zone of the dentate gyrus indicates that neurogenesis is taking place.

Niss1 staining, which stains the Niss1 body of the neuron, is a method that shows the distribution and condition of neurons in the brain. The brain tissues on the slides of Example 8 were rehydrated by sequentially immersing in xylene, 100%, 90%, 80%, 70%, 50% alcohol, and then water for 5 minutes each. After placing in 0.1% cresyl violet (Sigma, cat#. C5042) solution at room temperature for 15 minutes, they were dehydrated by sequentially immersing in 80%, 90%, 100% alcohol, and xylene. Coverslips were put on the slides and the neurons examined.

NeuN staining was performed by the same method as described in Example 8 as was DCX staining, but using anti-DCX antibodies (Santa Cruz, cat#. sc271390) instead of anti-NeuN antibodies.

Figure 16A:
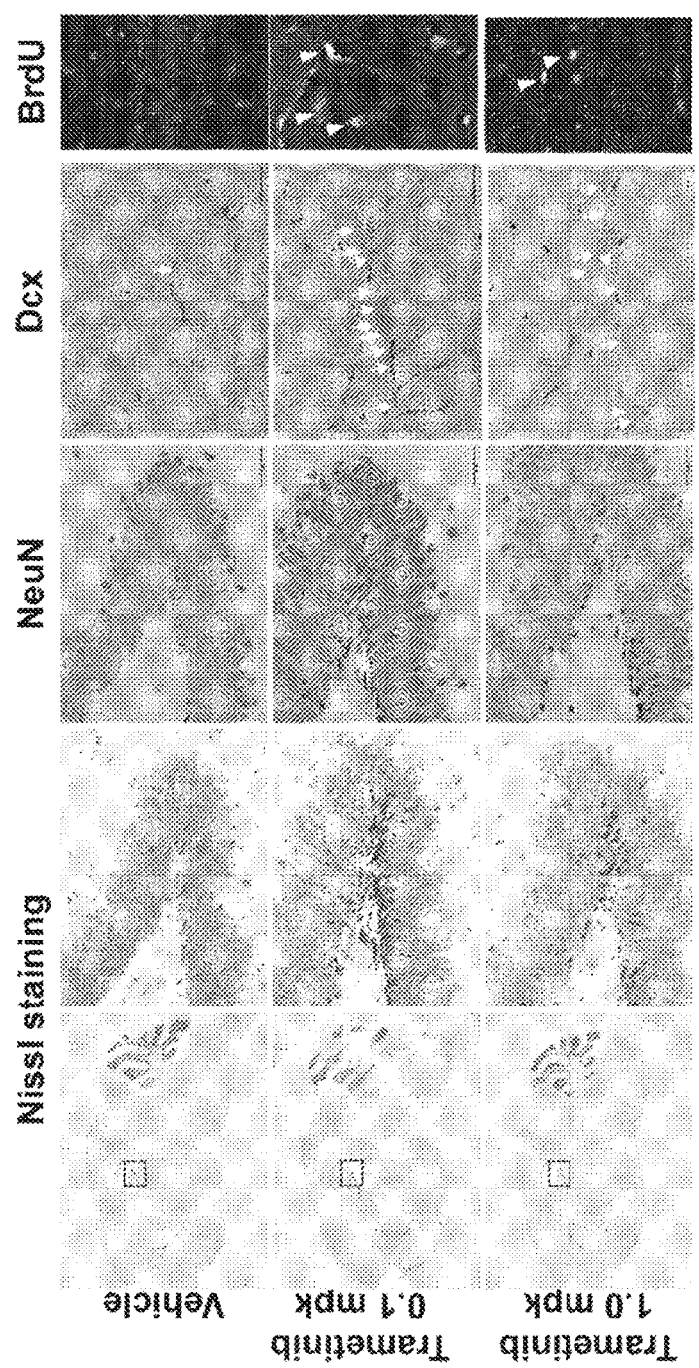
FIGS. 16a-16b are the result of Example 9-2 and 9-3 that shows Nissl, NeuN, Dcx and BrdU staining in slices of the hippocampal dentate gyrus of trametinib-administered 5XFAD mice (FIG. 16a) and the quantification of BrdU-labeled cells (FIG. 16b).

The results are shown in FIG. 16a. From the Niss1 and NeuN stainings in the trametinib-administered 5XFAD mouse, it was shown that the number of cells having the morphology of Type 2 or Type 3 cells that specifically appear during neurogenesis increased considerably in the subgranular zone (SGZ) and in an area closer to the granular zone than the SGZ in the dentate gyrus. In addition, immature neurons (marked with arrows (→) in the column labeled "Dcx" in FIG. 16) that are also stained by DCX were seen to be present, confirming that neurogenesis occurs in the hippocampal dentate gyrus in trametinib-administered mouse.

Example 9-3

BrdU Staining in the Hippocampal Dentate Gyrus Region

Asymmetric division of neural stem cells must proceed for neurogenesis to occur, and this was examined by the following experiment.

Brain tissue slides of BrdU-administered 5XFAD mouse (daily administration of 50 mg/kg BrdU for 5 consecutive days before sacrifice as described in Example 8) were rehydrated, placed in 1.5 M HCl (hydrochloric acid), and incubated at 37° C. for 30 minutes. The slides were blocked with solution containing 0.5% BSA (Bovine serum albumin), 0.3% TritonX-100, and 10% normal goat serum and incubated with anti-BrdU antibody (Cell signaling, cat#. 5292) at 4° C. for 1 day. Immunofluorescent staining was performed the next day by incubating the slides with fluorescein isothiocynate (FITC)-secondary antibody at room temperature for 1 hour, after which the staining of the hippocampal dentate gyrus region was examined with a fluorescent microscope.

Figure 16B:
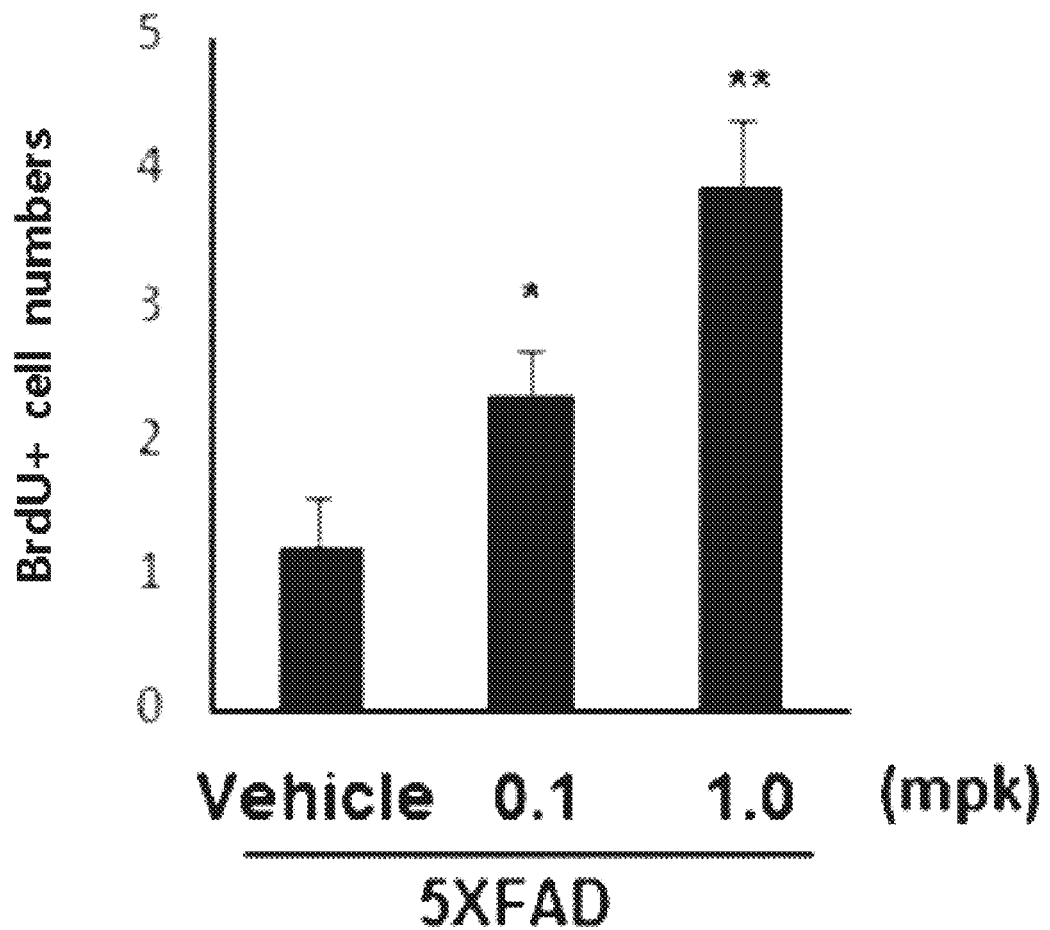

The results are shown in FIG. 16a in the column labeled "BrdU". The cells marked by arrowheads (▼) are the BrdU labeled cells. Compared with the vehicle-administered group, trametinib-administered 5XFAD mouse showed an increase in the number of cells stained with BrdU in the dentate gyrus. FIG. 16b shows the number of BrdU labeled cells, which again showed that the trametinib-administered group showed an increase in the number of cells stained with BrdU. FIG. 16b quantified the number of cells from a total of 9 areas (3 mice per group and 3 areas per mouse) and the average is shown in the graph.

From these results, it is revealed that trametinib induces neurogenesis through the differentiation of NSC in the AD mouse model. This suggests that not only can trametinib be used as a fundamental treatment for AD but also for the treatment and prevention of diseases that are caused by neuronal damage or loss in the cerebral cortex, particularly in the motor cortex.

Example 10

Neuroprotective Activity in the AD Mouse Model

In order to determine if trametinib has a neuroprotective effect in the cerebral cortex and hippocampal subiculum of the 5XFAD mouse, the immunohistochemical TUNEL (terminal deoxynucleotidyl transferase dUTP nick end labeling) assay was performed to detect cell apoptosis. The TUNEL assay stains the 3'-hydroxyl terminus of fragmented DNA, allowing the detection of cells undergoing apoptosis in the tissue.

The sagittal brain tissue slides described in Example 8 were rehydrated and stained with the TUNEL assay kit (Promega, Wis., USA, cat#. G3250). Specifically, the brain tissue slides were permeabilized with 20 μg/ml proteinase K solution for 10 minutes, incubated with equilibration buffer for 10 minutes, and then incubated with TdT solution at 37° C. for 1 hour. The staining of the somatosensory cortex and subiculum area, areas known to show significant cell death in 5XFAD mouse, were observed. TUNEL assay was also performed on the tissue slides of normal adult mouse brain (as control) to confirm that staining was properly done.

Figure 17:
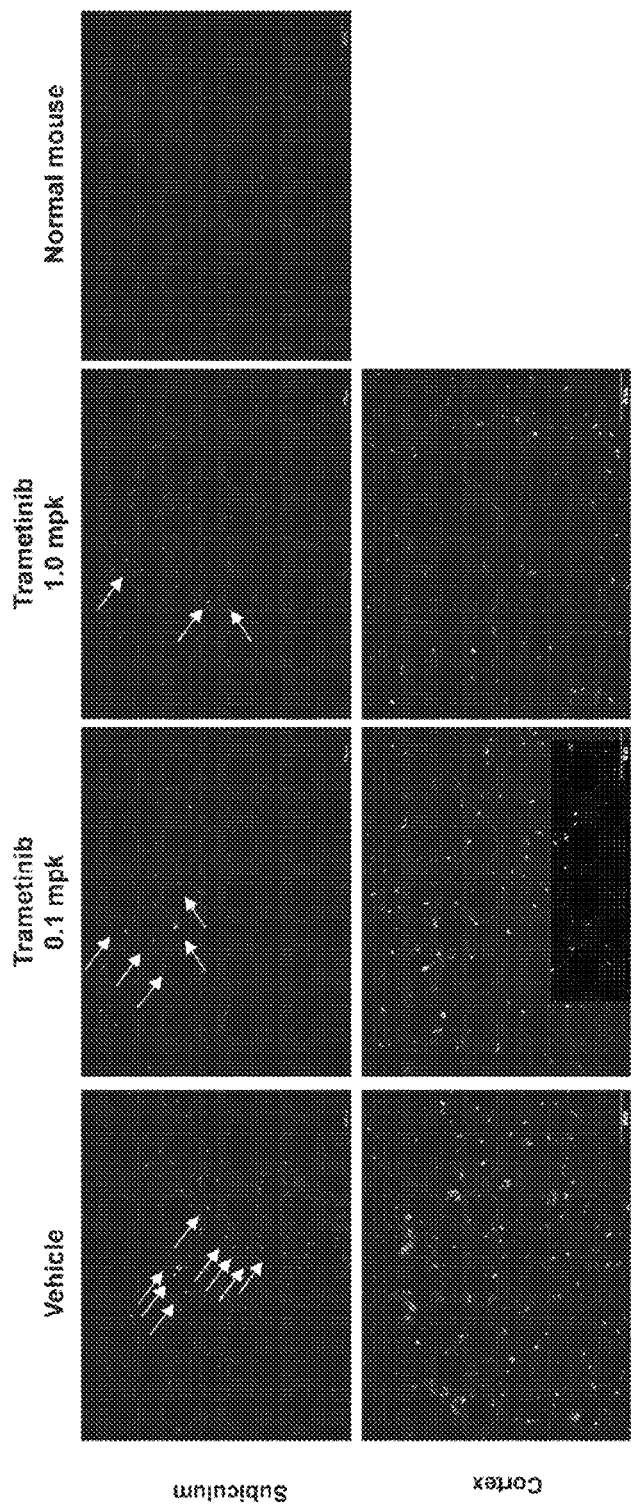
FIG. 17 is the result of Example 10 that shows TUNEL (Terminal deoxynucleotidyl transferase dUTP nick end labeling) staining, an indicator of apoptosis, in slices of the hippocampal subiculum and somatosensory cortex of trametinib-administered 5XFAD mice. Cells in the hippocampal subiculum that have undergone apoptosis and show green fluorescence are indicated with arrows (→).

The results are shown in FIG. 17. Green fluorescence staining was not observed in normal mouse (marked "Normal mouse" in FIG. 17) because apoptosis did not occur. However, green fluorescence was observed in many of the cells in the somatosensory cortex (row marked "cortex" in FIG. 17) and subiculum (row marked "subiculum" in FIG. 17) of the 5XFAD mouse. In FIG. 17, stained cells were marked with arrows (→) in the subiculum; in the somatosensory cortex, no separate marking was done due to many cells being stained. In the case of trametinib-administered 5XFAD mouse, the number of TUNEL stained cells in the somatosensory cortex and subiculum was significantly lower in comparison with the vehicle-administered group.

These results demonstrate that trametinib exerts a protective effect against neuron death in the AD mouse model.

Example 11

Cerebellar Purkinje Cell Protection in the AD Mouse Model

Brain tissue slides (of 5XFAD mouse) described in Example 8 were incubated with anti-Tuj1 and anti-calbindin antibodies (Cell signaling, cat#. 13176) at 4° C. for 1 day and were immunofluorescence stained with fluorescein isothiocyantate (FITC)-secondary antibodies or rhodamine-secondary antibodies at room temperature for 1 hour. The immunofluorescence image of the Purkinje cell layer is shown in FIG. 18. Two slides for Tuj1 staining and three for calbindin staining are shown for each treatment group.

As shown in FIG. 18, the Purkinje cells of the vehicle-treated group exhibited thin protruding axons that show a pattern of being cut off in the middle. In contrast, the trametinib-administered group, particularly the 0.1 mg/kg trametinib-treated group, exhibited Purkinje cells with increased axon arborization or at least with preserved axon structure when compared with the vehicle treated control.

The cerebellum is known to play an important role in the integration of sensory recognition and the regulation and control of motor movements. The most striking cells in the cerebellum, Purkinje cells are one of the largest cells in the brain, and through their elaborate axon arborization, they form synapses with each other and extend deep into the nucleus of the cerebellum to regulate and control motor muscle. The above experimental results indicate that trametinib protects the Purkinje cells and increases arborization of the axons in the cerebellum, possibly providing treatment to diseases such as cerebellar ataxia that are caused by the loss or damage of Purkinje cells in the cerebellum.

Example 12

Trametinib's Inhibition of MEK Activity in the AD Mouse Model

Since neurodegenerative disease treatment drugs act on the central nervous system, the question of whether or not they can cross the blood brain barrier to act on the brain is important. Among the MEK 1/2 inhibitors, compounds such as AS703026 are known to effectively cross the BBB and inhibit MEK and decrease the expression of phosphorylated ERK in the mouse brain (Shaw et al. (2012) Evaluation of brain pharmacokinetics as a potential differentiation factor for the MEK inhibitors, MSC2015103 and pimasertib. Abstract LB-456, American Association for Cancer Research Annual Meeting, Chicago, Ill.). To confirm that the MEK1/2 inhibitor trametinib enters the brain to produce the above experimental results when PO administered to 5XFAD mouse, the expression level of pERK was measured in the brain tissue.

Figure 19A:
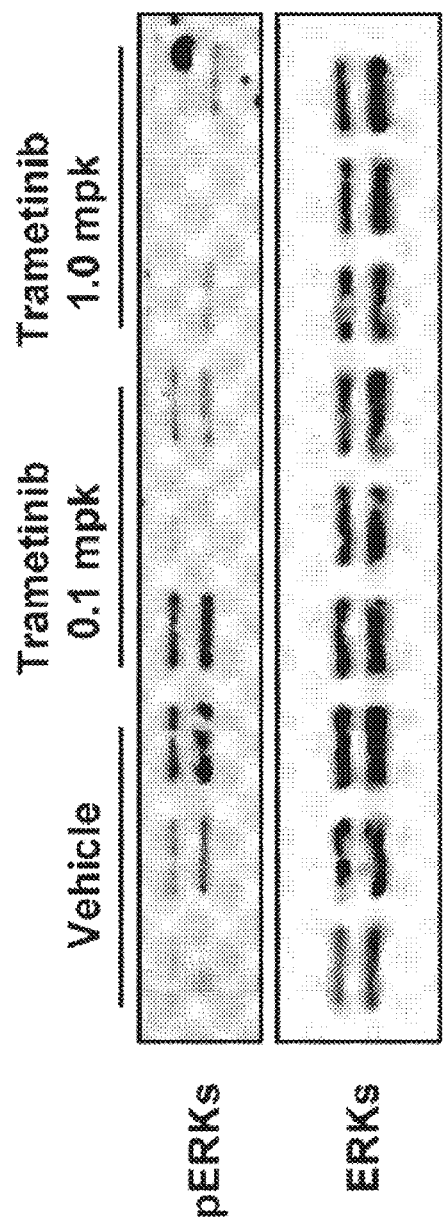
FIGS. 19a-19b are the result of Example 12 that confirms the presence or absence of the pERK protein through western blotting using the brain hemispheres of trametinib-administered 5XFAD mice (FIG. 19a)
Figure 19B:
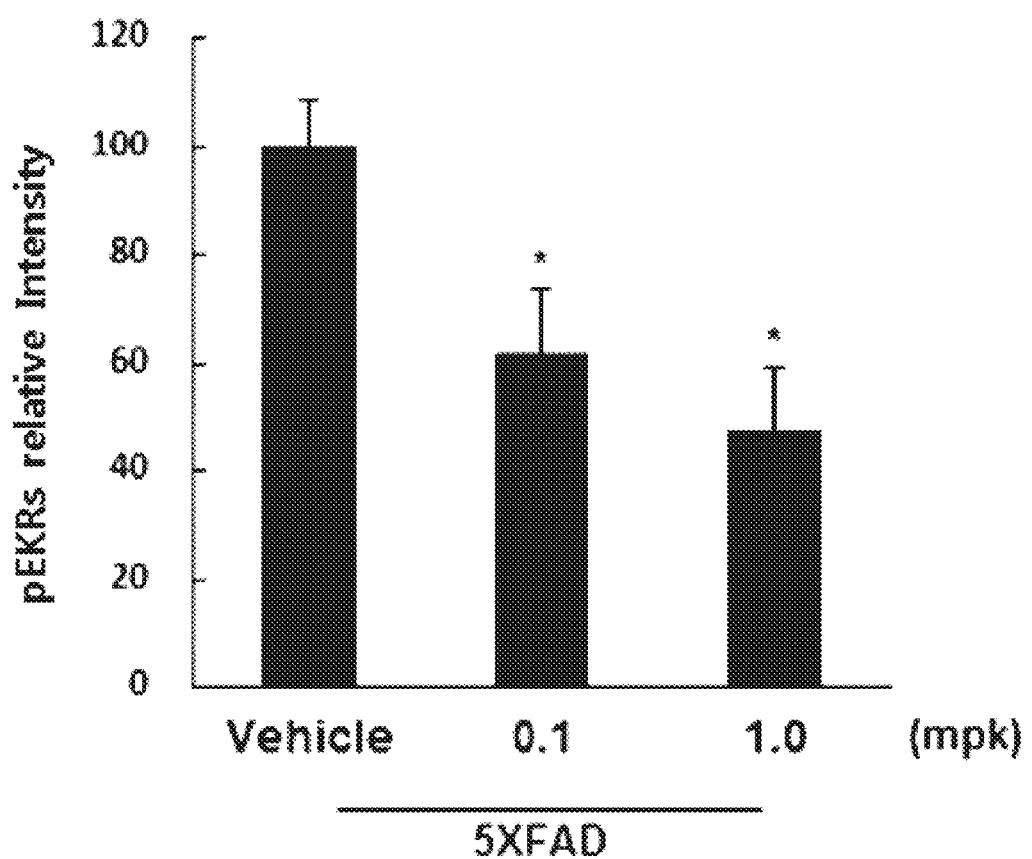

The 5XFAD mouse brain hemispheres (3 mice per group) from Example 8 stored in a deep freezer were placed in liquid nitrogen and ground in a mortar filled with liquid nitrogen. The powder was divided into 6 parts, put into new tubes, and placed back into the deep freezer. One of the tubes was taken out and used for western blotting as described in Example 5-2. The powder was carefully suspended with a pipette in RIPA buffer, incubated on ice for 10 minutes, centrifuged at 13000 rpm, 4° C., and the supernatant was collected. After measuring the protein concentration, sample buffer (0.25 M Tris-HCl pH6.8, 0.05% SDS, 50% glycerol, 0.25 M DTT, 0.5 mg/ml BPB) was added, boiled at 100° C. for 10 minutes, and stored at −20° C. 10 µg of protein sample was loaded onto a 10% SDS-PAGE gel, subjected to electrophoresis, transferred onto a nitrocellulose membrane, and blocked with 5% skim milk at room temperature for 1 hour. Western blotting was performed using anti-pERK (Cell signaling, cat#. 4370) and anti-ERK antibodies in tris buffered saline (TBS) with 0.1% Tween 20, which were incubated at room temperature for 1 hour and subsequently followed with incubation with horseradish peroxidase-conjugated secondary antibodies at room temperature for 1 hour. The protein bands were detected with a photosensitive imaging system (FIG. 19a). In order to quantify the change in pERK expression, the expression levels of pERK and ERK were measured by densitometry, and the expression level of pERK was normalized against the expression level of ERK. The normalized expression level of pERK in trametinib-treated group versus the vehicle-treated group is shown in FIG. 19b.

As shown in FIG. 19, the protein level of pERK in the brain of 0.1 mg/kg and 1.0 mg/kg trametinib-administered mouse is considerably lower than that of the vehicle group.

This finding indicates that the PO administration of trametinib results in the delivery of trametinib to the brain to subsequently inhibit MEK activity and decrease the expression of pERK, through which neurogenesis and neuroprotection appears to be manifested.

Example 13

Decrease in Amyloid-Beta Deposition in the AD Mouse Model

Since the main pathological feature of AD is the deposition of Aβ, the ability of trametinib to decrease the deposition of Aβ was examined. Using the ground powder of 5XFAD mouse brain hemispheres obtained in Example 12, the amount of Aβ(1-40) and Aβ(1-42) was quantified by ELISA (enzyme-linked immunosorbent assay). The assay was performed using an ELISA kit (Invitrogen, Mass., cat#. KHB3442) as follows: First, the mouse brain powder was carefully suspended with a pipette in 5 M guanidine-HCl solution, centrifuged at 16000×g (rpm), 4° C., and the supernatant was collected. After measuring the protein concentration, dilution buffer was added to obtain 30~50 µg of protein in 100 µl solution. 100 µl each of anti-Aβ(1-40) and Aβ(1-42) antibodies were added to the 96-well plates, incubated at room temperature for 2 hours, then removed and washed 4 times with wash buffer. 100 µl each of HRP-conjugated secondary antibodies was added and incubated at room temperature for 30 minutes. The solution was then removed and washed again 4 times with wash buffer. 100 µl of the protein prepared from the mouse brain powder was added to the wells, incubated in the dark for 30 minutes, and 100 µl of the stop solution added to terminate the reaction. Then, the chemiluminiscence reaction was measured at 450 nm with an ELISA plate reader. The absorbance was converted in reference to the standard concentration and the concentration of each protein was determined. The amount of Aβ(1-40) and Aβ(1-42) in reference to the total amount of protein (30~50 µg) was calculated, and then the amount of Aβ(1-42) in reference to the amount of Aβ(1-40) was calculated. The averages of the 3 mouse measurements for each group were obtained and are shown in FIG. 20. As shown in FIG. 20, the amount of Aβ(1-42)/Aβ(1-40) decreased in the trametinib-treated group compared with the vehicle-treated group.

This finding indicates that in the AD animal model, trametinib decreased the amount of Aβ, particularly the Aβ(1-42) form that has a strong tendency to form toxic oligomers or aggregates, and in this way, could provide protection to neurons.

What is claimed is:

1. A method of treating a neurodegenerative disease, comprising the step of: administering trametinib to a patient diagnosed with the neurodegenerative disease, wherein the neurodegenerative disease is a motor neuron disease selected from the group consisting of: amyotrophic lateral sclerosis (ALS or Lou-Gehrig's disease), primary lateral sclerosis, progressive bulbar palsy (PBP), progressive muscular atrophy (PMA), pseudobulbar palsy, and hereditary spastic paraplegia (HSP).

2. The method of claim 1, wherein the neurodegenerative disease is amyotrophic lateral sclerosis (ALS or Lou-Gehrig's disease).

3. The method of claim 1, wherein trametinib is administered in an amount sufficient to reduce a symptom associated with the neurodegenerative disease.

4. The method of claim 1, wherein trametinib is administered in an amount sufficient to induce neuro-regeneration.

5. The method of claim 4, wherein the amount is sufficient to induce differentiation of a neural stem cell into a neuron in the patient.

6. The method of claim 5, wherein the neuron differentiated from the neural stem cell is selected from the group consisting of: a dopaminergic neuron, a GABAergic neuron, a motor neuron, and a cholinergic neuron.

7. The method of claim 1, wherein trametinib is administered in an amount of between 0.1 mg and 2 mg once daily.

8. The method of claim 7, wherein trametinib is administered in an amount of not more than 1 mg once daily.

9. The method of claim 8, wherein trametinib is administered in an amount of not more than 0.5 mg once daily.

* * * * *